(12) United States Patent
Takesako et al.

(10) Patent No.: US 6,432,407 B1
(45) Date of Patent: Aug. 13, 2002

(54) ANTIGENIC PROTEIN ORIGINATING IN MALASSEZIA

(75) Inventors: Kazutoh Takesako, Otsu; Takashi Okado, Soraku-gun; Tomoko Yagihara, Hikone; Masanobu Kuroda, Otsu; Yoshimi Onishi, Kyoto; Ikunoshin Kato, Uji; Kazuo Akiyama, Kawasaki; Hiroshi Yasueda, Sagamihara; Hideyo Yamaguchi, Kawasaki, all of (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/091,097

(22) PCT Filed: Dec. 10, 1996

(86) PCT No.: PCT/JP96/03602

§ 371 (c)(1),
(2), (4) Date: Jun. 12, 1998

(87) PCT Pub. No.: WO97/21817

PCT Pub. Date: Jun. 19, 1997

(30) Foreign Application Priority Data

Dec. 12, 1995 (JP) .............................................. 7-346627
Sep. 5, 1996 (JP) .............................................. 8-257612
Sep. 5, 1996 (JP) .............................................. 8-257613

(51) Int. Cl.$^7$ ........................ A61K 39/00; A61K 38/00; C07K 2/00; C07K 1/00; C07K 7/00

(52) U.S. Cl. ................................ 424/184.1; 424/185.1; 424/191.1; 424/265.1; 424/275.1; 424/276.1; 424/278.1; 530/300; 530/324; 530/325; 530/326; 530/327; 530/328; 530/329; 530/350; 530/361; 530/858

(58) Field of Search ................................ 530/300, 350, 530/324, 325, 326, 327, 328, 329, 361, 858; 424/184.1, 185.1, 191.1, 265.1, 275.1, 276.1, 278.1

(56) References Cited

PUBLICATIONS

Savolainen and Broberg; Crossreacting IgE antibodies to *Pityrosporum ovale* and *Candida albicans* in atopic children; Clinical and Experimental allergy, vol. 22, 469–474, 1992.*
Rudinger et al ; Characteristics of the amino acids as components of a peptide hormone sequence; Peptide Hormones ; Edited byu Parsons ; University Park Press; Baltimore.Rudinger et al ; Characteristics of the amino acids as components of a peptide hormon, 1976.*
J. Allergy Clin. Immunolo. 89(1) (1992) Erika Jensen–Jarollim et al. "Atopic dermatitis of the face, scalp, and neck: Type I reaction to the yeast *Pityrosporum ovale*" pp. 44–51.
J. Exp. Med. 172(5) (1990) L. Karla Arrunda et al. "*Aspergillus fumigatus* Allergen I, a Major IgE–binding Protein, Is a Member of the Mitogillin Family of Cytotoxins" pp. 1529–1532.

J. Biol. Chem. 264(23) (1989) Lisa J. Garrard et al. "Two Genes Encode the Major Membrane–Peroxisomes from *Candida biodinii*" pp. 13929–13937.
Biochemistry 30(13) (1991) Takeshi Matsumoto et al. "Iron– and manganese–Containing Superoxide Dismutases from Methylomonas J: Identity of the Protein Moiety and Amino Acid Sequence" pp. 3210–3216.
J. Mol. Biol. 219(2) (1991) Martha I. Ludwig et al. "Manganese Superoxide Dismutase from *Thermus Thermophilus* A Structural Moel Refined at 1.8A Resolution" pp. 335–358.
J. Immunol. 149(2) (1992) Michel Moser et al. "Cloning and Expression of Recombinant Asperiguls fumigatus Allergen I/a (rAsp fI/a) with IgE Binding and Type I Skin test Activity"pp. 454–460.
IgE–binding Components in Pityrosporum orbiculare identified by an Immunoblotting Technique, Siv Johansson et al, Acta Derm Venereol (Stockh) 1991: 71: 11–16.
Allergy 1994: 49: 50–56 Identification of Alergen components of the opportunistic yeast Pityroporum orbiculare by monoclonal antibodies, A. Zargari et al.
M. Sentandreu et al., "Cloning of cDNA coding for Candida albicans cell surface proteins." Journal of Medical & Veterinary Mycology, vol. 33, No. 2, 1995, pp. 105–111, XP001022554.
L. Lindblom et al., "Cloning and sequencing of the cDNA encoding the Pityrosporum orbiculare 37 kDa major allergen."Journal of Allergy and Clinical Immunology, vol. 97, No. 1 part 3, 1996, p. 374 XP001034009.
H. Yasueda et al., "Identification and cloning of two novel allergens from the lipophilic yeast, Malassezia furfur." Biochemical and Biophysical Research Communications, vol. 248, No. 2, Jul. 20, 1998, pp. 240–244, XP002184076.

* cited by examiner

Primary Examiner—Mark Navarro
Assistant Examiner—Padma Baskar
(74) Attorney, Agent, or Firm—Birch, Stewart, Kolasch & Birch, LLP

(57) ABSTRACT

A substantially pure, isolated, antigenic protein from fungi of the genus Malassezia, characterized in that said antigenic protein has a binding ability to IgE antibodies from patients with allergoses; an antigenic fragment derived from the antigenic protein; and an antibody against the antigenic protein or fragments thereof. According to the present invention, there can be provided an isolated and purified antigenic protein having high purity from Malassezia, antigenic fragments thereof, and a specific antibody against those antigenic protein or fragments thereof. In addition, there can be provided a diagnostic agent, a therapeutic agent, or a prophylactic drug for Malassezia allergoses, wherein the agent includes, as an active ingredient, the antigenic protein or fragments thereof.

13 Claims, 37 Drawing Sheets

```
  1 GTTGAGCTCTGTGCTGAAGGCGCTCGCCGCCGGCTCTGCAGCTCTCTACTAAGGCTCTGA   50
    ||||||||||||||||||||||||||||||||||||||||||||||||||||||||||||
  1 GTTGAGCTCTGTGCTGAAGGCGCTCGCCGCCGGCTCTGCAGCTCTCTACTAAGGCTCTGA   50

51 AGCAGCCGCTTACGCCTCCCGTCGGCTCGCTCCCATTGGCGCTACGCCGCTG          100
    ||||||||||||||||||||||||||||||||||||||||||||||||||||
 51 AGCAGCCGCTTACGCCTCCCGTCGGCTCGCTCCCATTGGCGCTACGCCGCTG          100

101 GCTCGTGGCTACGCCTGAGCTCGGAGCCGTACGATGTCATTGTGATCGG            150
    |||||||||||||||||||||||||||||||||||||||||||||||||
101 GCTCGTGGCTATCCCGGAGCCGAGCCACATACGATGTCATTGTGATTGG            150

151 CGGTGGCCCCGGTAGCGTGCCGCATCAAGGCCACAGGGTGGTC                   200
    ||||||||||||||||||||||||||||||||||||||||||||
151 TGGTGGCCCCGGTAGCGTGCCGATCAAGGCCGCAGGCCAGGTGTC                 200

201 TGAAGACTGGTGTGTTGAGAAGTGCCCTTGGCGTACGTGCTTG                   250
    ||||||||||||||||||||||||||||||||||||||||||||
201 TGAAGACTGGTCATGTGTTGAGAAGTGCCGGCTTGTGCTTGTACCTGCTTG           250

251 AACGTGGCTGTATCCCGTTCCAAGTCGTTGCTCAACAACTGCACATCTA             300
    ||||||||||||||||||||||||||||||||||||||||||||||||
251 AACGTGGCTGTATCCCTTCCAAGTCGTTGCTGAACAACTGCACATCTT              300
```

FIG.17A

```
301  CCACCAGAGACGGACCAGAGACATGACCTCAAGAGAACCGGGTATTGACGTCGGCGACA   350
     ||||||||||| ||||||||| ||||||||||||||||||| |||||| ||||||
301  CCACCAGAGACGCGAGCAGAGACGCACCTCAAGAGAACCGGGTATTGACGTCAGCGAGG   350

351  TTAAGCTGAACCTGCCGCAGATGCTCAAGGCGAAGGAGAGCTCGGTTACT           400
     | ||| ||||| ||||||||||||||||||||||||||||||||| | |||
351  TCAAGTTGAACCTGCCGCAGATGCTCAAGGCGAAGGAGAGCTCGGTCACT           400

401  GCACTCACCAAGGGTGTCGAGGGTCTGTTCAAGAAGAACAAGTCGACTA             450
     |  ||| ||||||||||||||| |||||||||||||||||||||||||
401  GCGCTCACCAAGGGTGTCGAGGCCGTGTTCAAGAAGAACAAGTCGACTA             450

451  CATCAAGGACACTGCCAGCTTTGCCAGCCCCACGACGTGAAGC                   500
     || ||||||| || ||||||||| ||||| ||||||||| ||||
451  CCTCAAGGGCAGCAGCTTCGCGAGCCCTACGACGTGACGTGAAGC                 500

501  TGAACGATGGTGAGCAGATGAGGGCAAGAACATCATTGCA                       550
     ||||||||||||||||||||||||||||||||| ||||||
501  TGAACGATGGTGAACAGCAGATTGAGGCAAGAACATTATCATTGCG                 550

551  ACCGGCTCTGAGGTGACGCCCTTCCCGGGTGTTGAAATGACGAGGAGCA             600
     |||||||||||||| |||||||||||||||||||| |||||||||||||
551  ACTGGCTCTGAGGTGACGCCCTTCCCGGTGTGGAGATCGACGAGGAGCA             600
```

FIG.17B

601 GATCATCAGCTCGGTGCCGTCTCGCTTCAAGGAGGTGCCCGAGAAGA 650
    ||| ||||||||||||| |||||||||||||||||||| |||||||||
601 GATTATCAGCTCGGGTGCCGTCTCGCTTCAAGGAGGTGCCTGAGAAGA 650

651 TGGTCGTGATCGGTGGTGTGATCGGCTTGAGCTTGGCAGCTGTGG 700
    |||||||||||||||||||||||| || ||||||||| |||||||
651 TGGTCGTGATCGGTGGTGTGATCGGTGTTGAGCTTGGTCGGTAGCTGTGG 700

701 ACCCGTCTGGTGCCAAGGTGACCGTGGAGTTCCAGGAGGCGATCGG 750
    | |||||||||| |||||| |||||||||||||||||||| |||||
701 AGCCGTGGGCGCCAAGGTGTCCGTGGAGTTCCAGGACGCGATTGG 750

751 TGGTCCCGGTCTCGACAGGAGCCAACAGTTCAAGAAGCTGCTCG 800
    ||| |||||||||||| ||||||||| |||||||||||||||||
751 TGGCCCCGGTCTCGACGGTGAGCCAGCAGTTCAAGAAGCTGCTCG 800

FIG.17C

```
801  AGAAGCAGGGGCATCCACTTCAAGCTGGCACCAAGGTCAACGGCATTGAG  850
     |||||||||||||||||||||||||| |||||||||||| ||||||||||
801  AGAAGCAGGGGCATCCACTTCAAGCTTGGCACCAAGGTGAACGGGATTGAG  850

851  AAGGAGAACGGGCAAGGTGACTG-TCCGCACTGAGGGTAAGGATGGCAAGG  900
     |||||||||| ||||||||| || ||| |||||||| ||  ||| ||||||
851  AAGCAGGACTACGACGCCAAGTGATGGTCCGCACCGAGGGCAAAGACGCAAGG  900

901  AGCAGGACTACGATGCCAATGTTGTCTCGTTCCAATTGGCCGTCGCCCG  950
     ||||||||||||| ||||| |||||| ||| |||| |||| ||||||||
901  AGCAGGACTACGACGCCAACGTTGTCTCGTTCCATCGGTCGCCGCCCG  950

951  GTGACCAAGGGCCCTCAACCTCGAGGCGTCGAGCTCGACAAGAA  1000
     ||  ||||||||  |||| |||||||| |||||| ||||  ||||
951  GTGACGAAGGGCTTGAACCTCGAGGCGTTGAGCTTGATAAGAA  1000

1001 GGGCCGTGGTGTGACGAGTTCAACGACGAGTTCAAGGTGTCA  1050
     ||||||||||||||| ||||||||||| ||||||| ||||||||
1001 GGGCCGTGGTGTGACGATGAGTTCAACGACGAGTTCAAGGTGTCA  1050
```

FIG.17D

```
1051  AGTGCATTGGTGACGGCGAGCGTTCGGCCCCATGCTTGCGCACAAGGCCGAG  1100
      ||||||||||||||||||||||||||||||| ||||||| ||||||||||||
1051  AGTGCATTGGTGACGCGAGCGTTCGGCCCTATGCTTGCGCACAAGGCCGAG  1100

1101  GACGAGGGTATTGCCGTCGCCGAGATGCTTGCGACCGGTTATGCCACGT   1150
      |||||||||||||||||||||||||||||||||||||||| ||| |||||
1101  GACGAGGGTATGCCGTTGCTGAGATGCTTGCGACCGGTACGGCCACGT   1150

1151  CAACTACGACGTGATCCCTGCGGTGATCTACACGCACCCTGAGATCGCGT   1200
      ||||||||||||||||||||||||||||||||||||||||||||| ||||
1151  CAACTACGACGTGATCCCTGCGGTGATCTACACGCACCCCGAGATTGCGT   1200

1201  GGGTCGGCAAGTTCCCGAGCAGGAGCTCAAGAGAACGAGGCGTCAGTACAAG   1250
      |||||||||||||||||||||||||||||||||||||| |||||||||||
1201  GGGTCGGCAAGTTCCCGAGCAGGAGCTCAAGAGAACGATGCCGTCAGTACAAG   1250

1251  GTGGGCAAGTTCCCTGCCAACTCGGCGTGCTAAGACCAACGTCGA   1300
      ||||||||||||||||||||||||||||||||| |||||||||||
1251  GTGGGCAAGTTCCCTGCCAACTCGGCGTGCTAAGACCAACGTCGA   1300

1301  CACCGACGGCTTCGTCAAGTTCCGTGGAGAAGGAGACCGACAAGATTC   1350
      ||||||||| |||||||||||||||||||||||||||||||||||||
1301  CACCGACGGTTTGTCAAGTTCCGTGGAGAAGGACACCGACAAGATTC   1350
```

FIG.17E

```
1351 TCGGGGTGTTCATTATCGGCCCGAACGCTGGCGAGATGATCGCCGAGGCT 1400
     ||||||||||||||||||| |||||| |||||||||||||| ||||||||
1351 TCGGGGTGTTCATCATCGTCCCGAATGCCGCGAGATGATTGCCGAGGCT 1400

1401 GGCCTGGCTATGAGTACGCGAGTGTCGAGGATGTTGCGGCACCTG 1450
     ||||||||||||||||||||| ||||||||||| ||||||||||
1401 GGCCTGGCTATGAGTACGCGAGTGTCGAGGATGTCGCGGCACCTG 1450

1451 CCACGCGCACCCGAGCGCTCTCCGAGCCGTTCAAGGAGGGTGCGATGGCCG 1500
     |||| ||||||||||||||||||||||||||||||||||| |||||||||
1451 CCACGCGCACCCGAGCGCTCTCCGAGCCGTTCAAGGAGGGTGCGATGGCCG 1500

1501 CCTACTCGAAGCCCATCCAGATTTCGATTCGTAGGCTACCCCGATAGC 1550
     |||||||||||||  ||||| |||||||||||||  ||||||||||||
1501 CCTACTCGAAGCCCGATTCACTTTTGATTCGTAGTTTCCCCGATAGC 1550

1551 GCCCGATACGTTTCTCCAAAAAAAAAAAAAAAAAAAAAAAA 1600
     ||||||||||| ||| |||  ||||||||||||||||||||
1551 GCCCGATACGTCTTC-CTC-AAAAAAAAAAAAAAAAAAA 1600

1601 AAAAAAAA........................... 1650
     |||
1601 AAA............................... 1650
```

FIG.17F

```
  1  TTCTC---TCTGTTGATGAAGCTCAACCCCAAGGTCTACCGAGCTGCGCCT   50
          ||   |||||||| |||||||||||||||| ||||||||| |||||
 -1  ..CTAAGAT-TCTTGATGAAGCTGAACCCCAAGGTTACCGAGCTCCGCCT   48

51  GTACGACATCCGTCTTGCTCTCCGGTGTTGCTCGGACTTCGCACATCA    100
     ||||||||||||||| |||| ||||||||||| |||| |||||||||
 49  GTACGACATCCGCCTCGCTCTCCGGTGTTGCTGGGATCTCTGCACATCA   98

101  ACACGCCCTGCGGTGACCTTCGGGCTACGCCCAGGAC?ATCTTGAGGTGCC  150
     ||||| |||||||||| |||||| |||||||||||||   || |||||||
 99  ACACCCCGCGGTGACTTCGGGCTTCGGATGACCTCGAGGTGCC  148

151  GTTGACGCGCAAAGATTGTCCTGATCGCCCGTATGCGCAAGCC          200
     || |||| || ||||||| |||| |||| |||||||||||| ||||||
149  GTCGACGGTGCGAGATTGTCTGATCGCCCGTATGCCGCAAGCC         198

201  CGGCATGACCCGTGACGATCTGTTCAACTCGAACGCCCTCGATCGTCCGTG  250
     |||||||| |||||||| ||||||||||| ||||||||||||| ||||||
199  CGGCATGAGCCGTGACGTTCGTTCAACTGCTGACCTGAACGCCCTCGATTGTCCGTG  248

251  ACCTCGCCAAGACCGTGCCCAAGGTTGCCCCAAGGCCTACATTGGTATC   300
     ||||| ||||||| |||| ||||| ||||||||||| |||||| || ||
249  ACCTCGCCAAGGTCGTGGCTAAGGTCGCCCAAGGCTTACATTCGGGGTC   298
```

FIG.18A

```
301 ATCTCGAACCCCGTCAACTCGACGTGTCCGATCGTGCCGAGGTGTTCAA 350
    ||||||||||||||||||||||||||||||||||||||||||||||||
299 ATCTCGAACCCCGTCAACTCGACGTGTCCGATCGTGCCGAGGTGTTAAA 348

351 GAAGGGGGGTGTGTACGACCCCAAGCGCCTCTTCGGTGTGACACGCCTCG 400
    ||||||||||||||||||||||||||||||||||||||||||||||||
349 GAAGGCCGTGTGTACGACCCCAAGCGCCTCTTCGGTGTGACACGCCTCG 398

401 ACACCACGGTGCGGCCACCTTCCTGTCGGCATCACTGGCTCGGAACCG 450
    ||||||||||||||||||||||||||||||||||||||||||||||||
399 ACACCACGGGGCGGCCACCTTCCTGTCGGCATTGCTCGGAACCG 448

451 CAGACCACCAATGTCCCGTCATTGGTCGGGTCACTCGGTGTGACCATCGT 500
    ||||||||||||||||||||||||||||||||||||||||||||||||
449 CAGACCACCAACGTCTCGCAGGCCCATTGGTCCACTCGGTGTGACCATTGT 498

501 GCCTCTGTCGGCAGCCCAGGGTGACAAGTCGCAGGCCGAGC 550
    ||||||||||||||||||||||||||||||||||||||||
499 GCCCCTGATCTCGCAGCGCCCAGGGTGACAAGGTGCAGGCCGAGC 548

551 AGTACGACAAGCTCGTCCACGCCATTCAGTTCGGTGTGACGAGTCGTT 600
    ||||||||||||||||||||||||||||||||||||||||||||||||
549 AGTACGACAAGCTTGTGCACGCCATCCAGTTCGGTGTGACGAGTCGTC 598
```

FIG.18B

```
601 AAGGCCAAGGACGGTGCGGGTTCGGACGCTGTCGATGGCCTACGCCGC   650
    ||||||||||||||||||||||||||||||||||||||||||||||||
599 AAGGCCAAGGACGGTGCGGGTTCGGACGCTGTCGATGGCCTACGCCGC   648

651 CGCTGTCTTCACTGAGGCCTGACGGTCTTGACGGTCGAGGCGGTGA     700
    ||||||||||||||||||||||||||||||||||||||||||||||
649 CGCGTGTTTCACCGAGGCCTGCCCAAGGTCTCGACGCGTGAGGCGGTGA  698

701 CGCAGTGCACCTTCGTTGAGAGCCCCTGTTCAAGGACCAGGTTGACTTC  750
    ||||||||||||||||||||   |||||||||||||||||||||  |||
699 CGCAGTGCACCTTCGTCGAGAGCCCCGTTCAAGGACCAGGTCGA?TTC   748

751 TTCGCTTGCCCGTGAGTTCGCCGGTGTCGGCGAGAACATCCCTGC      800
    ||||||||||||||||||||||||||||||||||||||||||||||
749 TTCGCTTGCCCGTGAGTTCGCCGAGGGTGAAGAACATCCCTG?        798

801 CCTGCCCAAGCTCACCGCTGAGGAGCAGAAGCTG?T?GACGCCTGC     850
    ||||||||||||||||||||||||||||||||||  | ||||||||
799 TCTGCCGAAGCTCACCGCGAGGAGCAGAAGCTG?T?GACGCCTGC      848
```

FIG.18C

```
851  CCGACCTTGCCAAGAACATCAAGAAGGGTGTTGCGTTGCCGAGAAC  900
     |||||||||||||||||||||||||||| ||||||| |||||||||
849  CCGACCTTGCCAAGAACATCAAGAAGGGCGTTGCGTGGGCCGAGAAC 898

901  CCCTAAATGCGCAGAACCAGC-TTCCACGGAGCTTGCGCCAAGGAAGA 950
     || ||||||||||   ||||| ||  | |||||||||| |||| |||
899  CCGTAAATGCGCA-AAGCAAT?TATAGAGCTTGCGGAAGGAAAGGA 948

951  AACGCACATTT?TATAGAGCTTGTCCCTTTCCATTTAAAAAAA 1000
     || |  | |||  |  |||||| |||||||||| |||||||||
949  AATGTACGTTT?TATAGAACGTAGATCTGTCCCTTTCCACCTAAAAAAA 998

1001 AAAAAAAAAA...................................... 1050
     ||||||||||
999  AAAAAAAAAA...................................... 1048
```

FIG.18D

| MF-1 | 1 | GCCTGGTGATCCTACTGCTACTGCCAAGGGTAACGAGATCCCCGACACCC | 50 |
| --- | --- | --- | --- |
| MF-2 | -1 | ..C-GGAAAT--TG---GCT-C-G--A------CGA--TCCCC-A-ACGC | 48 |

| | 51 | T-CATGGGC-TACATCCCCCTGGA-CCCCGGAGCTCGA---CTCGGGTGAG | 100 |
| --- | --- | --- | --- |
| | 49 | TACGTTTGCATACGTGCCGTACAGCCCCG-AGCTCGAGGAC-CACAA-AG | 98 |

| | 101 | GTGTGTGGTATCCCCACCACCTTCAAGACCCGGACGAG-TGGAAGGGCA | 150 |
| --- | --- | --- | --- |
| | 99 | -TGTGTGGCATGCGAGCTTCCAGAGCCACGA-GCGCTGGAAGGGCA | 148 |

| | 151 | AGAAGGTTGTGATTGTCTCGAT-CCCGGGTGCCTACACCCCCATC-TGCC | 200 |
| --- | --- | --- | --- |
| | 149 | AGAAGGTGGTGATTGTGCGGTGCCCGG-TGCGTTCACGCCGA-CGTGC- | 198 |

| | 201 | ACCAGCAGCAC-ATCCCCCGCTTGTGAAGGGTGTG----GAT---G-AG | 250 |
| --- | --- | --- | --- |
| | 199 | ACC-GC-GAACCATGTGCC-GCC-GT-A--CGTG-GAAAAGATCCAGGAG | 248 |

FIG.19A

```
251 CTCAAG-GCCAAGGGTGTGTGAGCGCCGT-GTACGTCAT-TGCGTCGAACGA  300
       ||||||  |||||  ||||| |||| | ||||||||| | ||||||||||
249 CTCAAGAGC-AAGGGCGTCGACGAGTCGTG-GTGATCT-CGGCGAACGA  298

301 CCCCTTCGT-CATG-GCTGCCTGGGCA--ACTTCAA-CAACGCCAAGGA  350
       ||| |||  ||||  || || ||||   |||  | ||||  ||||||
299 CCCGTTCGTGC-TGAGC-GCATGGGGCATCAC---CGAGCA-CGCCAAGGA  348

351 CAAGGTCGTC-TTTGC-CACCGACACATTGACCTG-GCCTTCTCCAAGGCTC  400
       ||| |||    |||   |||| || ||| ||||| || |||||||| |||
349 CAACCT-GACGTTTGCCGCAG-GACGTCAAC-TGCGAGTTCTCCAAG-CAC  398

401 TCGG-CGGCGACGATCGACCTGAGCGCC-AAG--CACTTTGG--TGAGCGC  450
      | || ||| ||||| ||||  ||| ||| ||   |||| ||   || |||
399 TTTAACGCGACGCTGGACCTGT-CGTCGAAGGGCA-TG-GGCCTG--CGC  448

451 ACGGCCCGCTACGCTCTGATCATTGA-CGACAACAAGATTGTCGA---CT  500
    ||||| ||||||||| |||||   |||   || |||||||   |||
449 ACCGCGCGCTACGCTGATCGC-GAACGACCTCAAG---GTCGAGTACT  498
```

FIG.19B

```
501 TTG-CTTCGGACGAGGGCGA-CACTGGCAAGCTCCAGAACGCGTCGATCG  550
     ||| ||| ||||||||| || ||||||||||   |||    |||  ||||
499 TTGGCATCG-ACGAGGGCGAGC-C-G--AAGC----AGT-CG---TCGGCCG  548

551 AC-ACGATCCTCACCAAGGTCTAAAATGGGCCATGTGCCGT--TGT-GTGA  600
    || |||  |||    |||||||       || || ||||   ||  ||||
549 -CGACGGGTGCTGAGCAAGCTGTAG---TGCCG---T-T-C-TACT-TAGTCA  598

601 CCACTACCTAAAGGGTCCGTAGAGT-TCCAAGTCGTCAAGTCGTATATTTTT  650
     | || ||  || ||  ||| |||| | |||| ||||    | |||
599 ---A---AC---AA----TC-G-G--G-GTAT--A-GTC--G--CGTA-A----  648

651 TTTTAAAAAAAAA..............................  700
    ||||||||||
649 ----AAAAAAA................................  698
```

FIG.19C

```
MF-3    1 GG-GA--ACG-T--C-A-------TGACTGA-G------TA-C-A-C       50
          ||  ||  ||| |  | |      ||| || |      || | | |
MF-4    1 GATGTTCACGCTTGCTACGGCGCTGCTGCCGCGGCTG-CTGCCCCCTGCGAAC    50

51 TCT-CCC---T-----C-C----T-C---TGCC-CTAC-GCC-TA           100
          | | |||   |     | |    | |   |||| |||| ||| ||
       51 GCCGCCCAGATGGGTGTGCCACCAAGTACACGCTGCCCTGCGCCCCGCTGTA    100

101 CGA-T--G-CGC---TGGAGCCGTTTATCTCTAAG-GAGATCATG-ACGGT     150
          ||| |  | |||   |||||||| ||||| |||| |||||||| | |||
      101 CGACTACGGGCGCTCGAGCCGGCTCGAGCCGTTATCTCTAAGGGAGATCATGAGA-  150

151 C-CACCACGAGACAAGCACCACCAG-ACCTACGTGAACCTGAACAACCCCGC      200
          | |||||||||||||||||||||| |||||||||||||||||||| |||||
      151 CGCACTACGAGAAGCACCACC-GCACCTAGTCAACCTGAACAACCCCGC        200

201 CGAGAAGG-CGTACGCTGAGGCGACG-GC-CGCGAA-C-GA-CGTGCTTA       250
          |||||||| |||  |||| ||||| | |  ||||| |  | |||||||
      201 -G-GA-GGACA-A-GCTGAT-CGACGCTCCCGGCTCCCGAGAGCCCGCTCG      250

251 AGC-AGAT--C-CAGCTGCAGAGTGCGATCAAGTTCAAGGGCGTGGCCA        300
          |||||| |  |  |||||||||||||||||||||||||||||||||||
      251 -GCGAGATTGCCAGCTG-A-AC-GCGATCAAGTTCAAGGGCGTGGCCA        300
```

FIG.20A

```
301  CATCAACCACTGCTGTTCTGGAAGAACCTGGCCCC---C----CAGAGCGA    350
         ||||||||||||||| ||||||||||||||||    |    |||||| |
301  CATCAACCACTGCTGCTCTGGAAGAACCTGCCGCGAGAACA--AG-G--    350

351  G-GGTGGTG-GC-CAACT-GAACGA---TGGCCCTCTCAAGCAGGCCATCG    400
       |||| || ||  ||| ||| ||    |||| |||||||||||| ||||
351  GCGGCGGGCGAGCTGACTCGGGCGAGCTG-CGCTC-C--GC-G---ATCG    400

401  AGCAG-GAGTT----C---GG-CGACTTTG---A-GAAGTTCAAGACGACCTT    450
       |||| ||||     |   || ||||  |   | ||| ||||    ||
401  ACC--GCGACTTTGGCCTCGGTGAC----GCCATGAAGG---A-GAAG----TT    450

451  CAACACGAAG-GCG-GCCGGGCATCCAGGGTTC-G-GGCTGGCTG--TGGCT    500
     ||| |||    |||  ||| ||||||||||   | |||||| |  |||||
451  CAACGCG---GCGCTCGCGGGCATCCAGG---CAGCGGCTGGG--GCTGGCT    500

501  CGG---TGTTGCCC--CGACGG-GCAACCTGACCTGGTCGTTG--CCAAG-G    550
             | ||||   ||| || |||||||||| ||||| |||  ||||| |
501  CGGCCTGAACCCTGAACCCCAG-AAGCTGACATCATCAC-GACC--GCG    550

551  A--CCAGGACCCGCTCAC--GAGCCACCCCG-TCATTGGC-TGGATGG    600
      |  |||||||||||||   |||||||||| |||||||| |||||| 
551  AACCAGGACCCGCTC--CTGTCGCACAAGCC-CTGATTGGCATCG-ATG--    600
```

FIG.20B

```
601  C-TGGGAGCACGCCCTGGTACCTGCAGTACAAGAACGACAAGGCTTC---CT  650
        | ||||||||| ||||||||||||||||||||||| |||||||| |   ||
601  CGTGGGAGCACGGTTCTACCTGCAGTACAAGAACGTCAAGGC---CGACT  650

651  ACCTT-AAGGCC-TGGTGGAACGTGGTGAACTG-G-GCCGAGGCCGAGAA  700
     ||||| |||||| |||||| ||||||||||||| | | ||||||||||||
651  AC-TTCAAGGCGATC--TGGACCGTGATCAACTTTGAG--GAGGCCGAGAA  700

701  GCGCTTCCTCGAGGGTAAGAAGAAGGC-C-CAGCT--GTAA-TGG-CACG  750
     ||| |   |  | |||  |  ||  |  |  |||   |      ||  | 
701  GCG-T-C-TC-A---A-G--GA-GGCGCTC-GCCAAG-AACTAGACACG  750

751  TTTGTAGATGATGAACGACACGATTTTAGGT-CGCACGG-CC-G---A  800
     |||  |    ||  | | |       |     | ||||  || ||   |
751  TTCG--GTTTTTTT-CTC-CG-T---AGCTTCGCAATGACCTGCCCA  800

801  GGCTACTAAAAAAAAAAAAAAAAAAAAAAAAAAAAAAAAAAAAAAAAAAAAA  850
     ||||| ||||||||||||||||||||||||||||||||||||||||||||
801  CGCTAAAAAAAAAAAAAAAAAAAAAAAAAAAAAAAAAAAAAAAAAAAA  850

851  AAAAAA.............................................  900
     ||||||
851  AAAAAAAAAAAAAAAAAAAA..............................  900
```

FIG.20C

| No. | Amino Acid Sequence | Number of Residual Group | HPLC Retention Time (min) |
|---|---|---|---|
| 1 | PGDPTATAKGNEIPDT | 16 | 23.5 |
| 2 | ATAKGNEIPDTLMGY | 15 | 32.4 |
| 3 | NEIPDTLMGYIPWTPEL | 17 | 44.0 |
| 4 | TLMGYIPWTPELDSG | 15 | 40.8 |
| 5 | IPWTPELDSGEVCGI | 15 | 39.4 |
| 6 | ELDSGEVCGIPTTFK | 15 | 33.0 |
| 7 | EVCGIPTTFKTRDEW | 15 | 42.1 |
| 8 | PTTFKTRDEWKGKKV | 15 | 22.9 |
| 9 | TRDEWKGKKVVIVSI | 15 | 29.9 |
| 10 | KGKKVVIVSIPGAYT | 15 | 29.9 |
| 11 | VIVSIPGAYTPICHQ | 15 | 34.0 |
| 12 | PGAYTPICHQQHIPPLV | 17 | 44.6 |
| 13 | PICHQQHIPPLVKRV | 15 | 27.7 |
| 14 | QHIPPLVKRVDELKA | 15 | 29.9 |
| 15 | LVKRVDELKAKGVDA | 15 | 23.3 |
| 16 | DELKAKGVDAVYVIA | 15 | 31.3 |
| 17 | KGVDAVYVIASNDPFVM | 17 | 39.8 |
| 18 | VYVIASNDPFVMAAW | 15 | 43.2 |
| 19 | SNDPFVMAAWGNFNNA | 16 | 39.1 |
| 20 | VMAAWGNFNNAKDKV | 15 | 30.4 |
| 21 | GNFNNAKDKVVFATD | 15 | 26.8 |
| 22 | AKDKVVFATDIDLAF | 15 | 37.4 |
| 23 | VFATDIDLAFSKALG | 15 | 39.6 |
| 24 | IDLAFSKALGATIDL | 15 | 40.3 |
| 25 | SKALGATIDLSAKHF | 15 | 29.8 |
| 26 | ATIDLSAKHFGERTA | 15 | 26.3 |
| 27 | SAKHFGERTARYALI | 15 | 28.4 |
| 28 | GERTARYALIIDDNK | 15 | 27.5 |
| 29 | RYALIIDDNKIVDFA | 15 | 35.7 |
| 30 | IDDNKIVDFASDEGD | 15 | 29.3 |
| 31 | IVDFASDEGDTGKLQ | 15 | 28.1 |
| 32 | SDEGDTGKLQNASID | 15 | 22.6 |
| 33 | TGKLQNASIDTILYKV | 16 | 34.8 |

HPLC Analysis Conditions:
   TSK-gel ODS 4.6 φ × 250 mm: UV 210 nm: 0-60% of
   60-minute linear gradient elution with acetonitrile
   containing 0.05% TFA: 1.0 ml/min: 40°C

FIG.21

```
Genomic
DNA    1  AGACAGGAGGGACATGGTTTAGAAGCACAATTCGGGTAGCCTGGGCGCTGAAGGGATACTC    60
cDNA   1                                                                1

61  GCTGAGAAATTCACTTTCCCCCGCTGACGCCCAGACTGTCCCGAATTACCA           120
       1                                                                1

121  AGCAAATGCACGTGACGTTGTGGAGCCTCGGGGATTATCAGGCCACGTATCAGTGAGCC   180
       1                                                                1

181  GAGCACCGCGTGGCTTCGGCGTCATATAAAGCCGGGTGCCGTGCTCACAGCTTC       240
       1                                                                1

241  ATCTTCCACGACAATCATTATGCCTGGTGTAGGTACCGCGAAGTGACACGCATGCTGACC  300
       1                                        M  P  G

301  ATCAGGATCCTACTGCTACTGCCAAGGGTAACGAGATCCCCGACACCCTCATGGGCTACA  360
       1   D  P  T  A  T  A  K  G  N  E  I  P  D  T  L  M  G  Y        18

361  TCCCCTGGACCCCGGAGCTGGACTCGGGTGAGTGTGTGGTATCCCCACCTTCAAGA      420
      19   I  P  W  T  P  E  L  D  S  G  E  V  C  G  I  P  T  F  K     38

421  CCCGGCGACGAGTGGAAGGGCAAGAAGTTGATTGTCTCGATCCCGGTGCCTACACCC     480
      39   T  R  D  E  W  K  G  K  K  V  I  V  S  I  P  G  A  Y  T     58
```

FIG.23A

```
481 CCATCTGCCACCAGCAGCACATCCCCCGCTTGTGAAGCGTGTGGATGAGCTCAAGGCCA 540
 59  P  I  C  H  Q  Q  H  I  P  P  L  V  K  R  V  D  E  L  K  A   78

541 AGGGTGTGACGCCGTGTACGTCGTGTAGTTGCGTCATTGCGAACGACCCCTTGTCATGGGTATGTACT 600
 79  K  G  V  D  A  V  Y  V  V  I  A  S  N  D  P  F  V  M          95

601 GCTCTGTCATTCTTTATGCTAACCGACAGCTGCCTGGGGCAACTTCAACAACGCCAAGG 660
 95           A  A  W  G  N  F  N  N  A  K                        110

661 ACAAGGTCGTCGTCTTTGCCACCGACATTGACCTGGCCTTCTCCAAGGCTCTCGGCGACGA 720
111  D  K  V  V  F  A  T  D  I  D  L  A  F  S  K  A  L  G  A  T  130

721 TCGACCTGAGCGCCAAGCACTTTGGTGAGCGCACGGCCCGCTACGCTCTGATCATTGACG 780
131  I  D  L  S  A  K  H  F  G  E  R  T  A  R  Y  A  L  I  I  D  150

781 ACAACAAGATTGTCGACTTCGCTTCGGACGAGGGGGACACTGGCAAGCTCCAGAACGCGT 840
151  D  N  K  I  V  D  F  A  S  D  E  G  D  T  G  K  L  Q  N  A  170

841 CGATCGACACGATCCTCACCAAGGTCATGTGCGTTGTGTGACCACTACC 900
171  S  I  D  T  I  L  T  K  V  *                                  180

901 TAAAAGGGTCCGTAGAGTTCAAGTCGTATATTTTTTTTTACAGGATGGTGTGTA 960
                                                                    180

961 CTGCCACCTGCCTTTGAGCAAGGCGTGCCAG 991
                                                                    180
```

FIG.23B

ANTIGENIC PROTEIN ORIGINATING IN MALASSEZIA

This application is the national phase under 35 U.S.C. §371 of prior PCT International Application No., PCT/JP96/03602, which has an International filing date of Dec. 10, 1996, which designated the United States of America, the entire contents of which are hereby incorporated by reference.

TECHNICAL FIELD

The present invention relates to a novel antigenic protein which is isolated and purified from Malassezia fungi, useful for diagnosis, treatment, and prophylaxis for allergoses and infectious diseases of which causative microorganisms are Malassezia fungi, and to antigenic fragments thereof, an antibody against the antigenic protein or antigenic fragments thereof, and the like.

Further, the present invention relates to a recombinant Malassezia antigenic protein, a gene encoding the antigenic protein, and also to an epitope of the protein, and the like.

BACKGROUND ART

As a result of sensitization by the causative antigen for the diseases, in many of the allergoses, an antigen (allergen)-specific IgE antibody (reagin antibody) is produced in sera and tissue. Upon re-exposure to the same antigen, IgE bound to the mast cells or basophiles and the specific allergen become coupled together to cause IgE crosslink on the cell surface, resulting in physiological effects due to the IgE-antigen interaction. Such physiological effects include the release of histamine, serotonin, heparin, eosinophilic chemotactic factor, or various leukotrienes, whereby persisting constriction of bronchial smooth muscle is caused. These released substances act as chemical mediators to induce allergic symptoms due to a coupling of IgE and a particular allergen. The effects of an allergen manifest themselves via these symptoms, and such effects can occur systemically or locally, depending on the route of antigen invasion in the body and the pattern of IgE sedimentation on mast cells or basophiles. Local symptoms generally occur on the epithelial surface at the position of allergen invasion in the body. Systemic effects are consequences of IgE-basophile response to the antigen in the blood vessels, which are typically exemplified by anaphylactic shock. The helper T (Th) cell plays a key role in the series of reactions. Among the various cytokines produced by Th cells activated by antigen stimulation, IL4 promotes IgE production.

A wide variety of substances induce allergic symptoms in humans. To date, allergens have been viewed as an assembly of a large number of substances represented by pollens or house dusts. As a result of recent advances in separation and purification techniques and methods for evaluating allergen activity, it has been clearly obvious that the allergen comprises a single substance or several kinds of principal substances. In particular, a rapid progress in research into allergens of *Cryptomeria japonica* (Japanese cedar) pollen, ticks, cats, and the like has been made, and major allergens, such as Cry j 1 and Cry j 2 have been isolated from *Cryptomeria japonica* pollen; Der f 1, Der f 2, and Der f 3 have been isolated from ticks; and Fel d 1 has been isolated from cats. Furthermore, genes encoding these allergenic proteins have also been isolated, thereby making it possible to prepare pure allergenic proteins in large amounts by genetic engineering techniques.

In the diagnosis of allergoses, it is necessary to first identify the antigen of which the microorganisms are causative, and in order to accomplish this purpose, over 100 kinds of commercially available antigen extracts, and in some cases, those prepared in-house, are first subjected to intracutaneous tests using suspected antigen extracts. In the case where an antigen of which is a very likelihood of being the causative antigen is found, the antigen can be specifically identified by assaying serum IgE antibody titration by RAST method and the like, provocative tests, or histamine release tests using whole blood or lymphocytes. Because these antigen extracts do not have their potency well titrated, however, attention should be marked to the risk of anaphylactogenesis upon use. Usable therapies for allergoses include antihistaminics, steroidal anti-inflammatory drugs, and mediator release suppressors, and the therapy of hyposensitization using a diagnostically specified antigen serves excellently. It should be noted, however, that the currently available method of therapy of hyposensitization requires an antigen solution to be intracutaneously administered little by little once or twice each week for three to four months over which period the starting dose is escalated to a maintenance dose, which is then maintained for one to three years. If dose escalation is easy, it can be expected that excellent therapeutic effects can be obtained. However, grave side reactions can occur because of the above uncertain potency of the antigen used, and because of the presence of various impurity substances therein, thereby greatly limiting its use of the antigen.

Fungi belonging to the genus Malassezia (hereinafter abbreviated as M.) are known to include *M. furfur* (also known as *Pityrosporum ovale* or *Pityrosporum orbiculare*), *M. pachydermatis, M. sympodialis*, and the like. Malassezia is reportedly commonly present on the body surfaces of various animals and on those of humans. Its pathogenicity and role in allergoses have long been studied. Regarding pathogenicity, Malassezia is suspected of being causative microorganisms for dermatitis, tinea versicolor, folliculitis, dandruff, and other conditions. It is also suspected of being associated with allergoses, such as atopic dermatitis, and there is a great chance that it is involved in these diseases as a causative microorganism.

Currently, antigen extracts from Malassezia are commercially available. These extracts are unpurified or partially purified products obtained from cultures of *M. furfur*, and are thus considered complex mixtures comprising proteins, sugars, and lipids.

Conventionally, a large number of allergenic proteins from Malassezia have been reported to be contained in such antigen extracts, including 87, 76, 67, 45, 37, 28, 25, 14, 13 kDa IgE-binding proteins, which are detected by immunoblotting using IgE antibodies in sera of patients after a crude extract from a Malassezia fungus is separated by SDS-polyacrylamide gel electrophoresis (PAGE) (Siv Johansson et al., *Acta Derm. Venereol.*, 71, 11–16, 1991; E. Jensen-Jarolim et al., *J. Allergy Clin. Immunol.*, 89, 44–51, 1992; Zargari et al., *Allergy*, 49, 50–56, 1994). Thus, since the proteins produced by the Malassezia fungi are beyond a wide variety of proteins, simple separation by SDS-PAGE alone is unsatisfactory, and it cannot be thought that a single protein band in SDS-PAGE which is conventionally reported represents a homogenous protein. In other words, because a plurality of proteins sharing the same protein band in SDS-PAGE are usually present, an IgE-binding protein, even if a single protein band is shown, must be separated from many other proteins contained in the band, which in turn necessitates combining with another effective separation method. Furthermore, in order to be useful for a diagnostic or therapeutic purpose, it is necessary to isolate an antigenic protein and clarify its antigenicity using a number of sera from patients, to identify it as the major allergen, and to establish a method for producing it for supplying the desired produce with demonstrated protein chemical quality. For these reasons, a homogenous and single antigenic protein must be isolated by repeating separation by various chromatographies and assay of the antigen activity. The protein finally obtained needs to be confirmed as having homogeneity in ion exchange chromatography and homogeneity in isoelectric electrophoresis, as well as that in SDS-PAGE.

According to the above-mentioned various reports, however, such substances observed in SDS-PAGE are dealt with as if they each represent a single IgE-binding protein. Actually, however, no one have yet been successful to isolate and purify them, and there have never been discussed on the identity of the band as a mixture of many mutually unrelated proteins. Accordingly, as a matter of course, no attempts have been yet made to isolate IgE-binding proteins from the complicated mixture and confirm the antigenicity thereof as isolated proteins using sera of patients with allergy. Further, no reports have been yet made regarding the properties of protein chemistry or amino acid sequences thereof. For this reason, it remains unknown as to the mutual identity or relevancy (for example, one is a decomposition product by protease of the other protein), and other aspects of IgE-binding proteins discussed in the above reports.

Even though the Malassezia fungi have been remarked as causative microorganisms for allergoses, including atopic dermatitis, as described above, no one have yet succeeded in isolating and purifying an IgE-binding protein from a crude extract comprising a complicated protein mixture. As a matter of course, the antigenicity of such an isolated protein has not been confirmed using sera of patients with allergy. Moreover, there have been no reports of the properties of protein chemistry or amino acid sequences thereof, and there are no reported cases on isolation of the gene encoding the above protein.

DISCLOSURE OF THE INVENTION

In order to assess the likelihood of being a causative microorganism, skin tests using crude antigens, Malassezia cell extracts as described above, provocative tests, quantitative assay tests for various IgE antibodies by RAST method, assay for histamine release, and the like, and other approaches are performed, in addition to microbiological cultivation tests. Because these crude antigens contain a large number of different impurity substances, however, accurate diagnosis cannot be made. In addition, when used for skin tests and provocative tests, the crude antigen can pose a risk of development of adverse reactions, and the like. Moreover, when using the crude antigen for therapy of hyposensitization, there is a risk of anaphylactogenesis associated therewith, posing extreme limitation on the dose of the crude antigen, so that therapeutic effects cannot be expected. In addition, it is also difficult to use the crude antigen as a vaccine for preventing infections. To date, there have been no successful cases on isolation of such purified pure antigen from Malassezia, and there is, therefore, a major set back on the infections caused by Malassezia fungi and the diagnosis and therapy of allergoses.

Accordingly, in consideration of the present situation, the following objects are achieved by the present invention.

(1) A first object of the present invention is to provide a substantially pure, isolated, antigenic protein from fungi of the genus Malassezia, namely a purified Malassezia allergen, preferably a main allergen for patients with Malassezia allergoses, and to provide their properties of protein chemistry. Further, the object is also to provide a functionally equivalent antigenic protein having properties immunologically equivalent to those of the antigenic protein.

(2) A second object of the present invention is to provide an antigenic fragment having an antigenic epitope contained in these purified antigenic proteins.

(3) A third object of the present invention is to provide an antibody or fragments thereof against the above antigenic protein or antigenic fragments.

(4) A fourth object of the present invention is to provide a diagnostic agent for diseases, such as allergoses of which causative microorganisms are Malassezia fungi, the diagnostic agent including, as an active ingredient, the above antigenic protein or antigenic fragments.

(5) A fifth object of the present invention is to provide a therapeutic agent for diseases, such as allergoses of which causative microorganisms are Malassezia fungi, the therapeutic agent including, as an active ingredient, the above antigenic protein or antigenic fragments.

(6) A sixth object of the present invention is to provide a method for immunological, quantitative assay of the Malassezia allergen.

(7) A seventh object of the present invention is to provide a novel recombinant Malassezia antigenic protein having immunological properties equivalent to those of the purified antigenic protein of item (1).

(8) A eighth object of the present invention is to provide a polynucleotide encoding a novel recombinant Malassezia antigenic protein.

(9) A ninth object of the present invention is to provide an antigenic fragment having an epitope contained in the recombinant Malassezia antigenic protein.

(10) A tenth object of the present invention is to provide an antibody or fragments thereof which specifically bind to the above recombinant Malassezla antigenic protein or antigenic fragments thereof.

(11) An eleventh object of the present invention is to provide a synthesized oligonucleotide probe or a synthesized oligonucleotide primer which hybridizes to the above polynucleotide.

(12) A twelveth object of the present invention is to provide a diagnostic agent for Malassezia allergoses or Malassezia infectious diseases, including, as an active ingredient, the above recombinant Malassezia antigenic protein or antigenic fragments thereof.

(13) A thirteenth object of the present invention is to provide a therapeutic agent for Malassezia allergoses or Malassezia infectious diseases, including, as an active ingredient, the above recombinant Malassezia antigenic protein or antigenic fragments thereof.

For the purpose of isolating Malassezia allergens useful for the diagnosis and therapy of patients with allergy with the cell components of M. furfur TIMM2782, a fungal strain belonging to the genus Malassezia, the present inventors have screened sera of patients with RAST-positive and positive skin tests for antigenic proteins, using cell extract crude antigens. As a result, the present inventors have succeeded in isolating 13 kinds of antigenic proteins designated as MF-1 to -13, respectively, and also succeeded in determination of the partial amino acid sequences of some of the antigenic proteins. Moreover, the present inventors have synthesized a polynucleotide to be used for primers on the basis of the information for the partial amino acid sequences of the Malassezia antigenic proteins thus isolated, and carried out polymerase chain reaction (PCR) with a cDNA derived from M. furfur cell mRNA as the starting material, using the polynucleotide as a primer, to give a portion of the gene encoding the desired Malassezia antigenic protein. Next, the desired gene has been isolated from an M. furfur cell cDNA library using the entire or partial fragment of this PCR fragment as a probe. Also, an overlapping peptide has been synthesized on the basis of the amino acid sequence of MF-1. The present inventors have clarified that an epitope for T cell and an epitope for B cell can be found by carrying out search for an epitope against the patient serum IgE antibody and search for another epitope against the MF-1 monoclonal antibody, using the above peptide. The present invention has been completed based on the above finding.

In other words, one embodiment of the present invention relates to a substantially pure, isolated, antigenic protein or antigenic fragments thereof from fungi of the genus Malassezia, characterized by having a binding ability to an IgE antibody from patients with allergoses.

Another embodiment of the present invention relates to a recombinant Malassezia antigenic protein or antigenic fragments thereof, characterized by having immunological properties functionally equivalent to those of the isolated and purified antigenic protein.

Another embodiment of the present invention relates to a polynucleotide encoding the recombinant Malassezia antigenic protein or antigenic fragments thereof of the present invention.

Another embodiment of the present invention relates to an antibody or fragments thereof against the isolated and purified antigenic protein or antigenic fragments thereof of the present invention, or against the recombinant Malassezia antigenic protein or antigenic fragments thereof of the present invention.

Another embodiment of the present invention relates to a synthesized oligonucleotide probe or a synthesized oligonucleotide primer which hybridizes to the polynucleotide of the present invention.

Another embodiment of the present invention relates to a diagnostic agent for Malassezia allergoses or Malassezia infectious diseases, characterized in that the diagnostic agent includes, as an active ingredient, the isolated and purified antigenic protein or antigenic fragments thereof of the present invention, or the recombinant Malassezia antigenic protein or antigenic fragments thereof of the present invention.

Another embodiment of the present invention relates to a therapeutic agent for Malassezia allergoses or Malassezia infectious diseases, characterized in that the therapeutic agent includes, as an active ingredient, the isolated and purified, antigenic protein or antigenic fragments thereof of the present invention, or the recombinant Malassezia antigenic protein or antigenic fragments thereof of the present invention.

Another embodiment of the present invention relates to a method for quantitative assay of Malassezia allergen, characterized in that the immunological, quantitative assay of the Malassezia allergen is conducted by using the isolated and purified antigenic protein of the present invention, or the recombinant Malassezia antigenic protein of the present invention as a standard and antibodies against the above antigenic protein.

BRIEF DESCRIPTION OF THE DRAWINGS

FIG. 17 is comparative figures of two nucleotide sequences of MF-5 cDNA (SEQ ID NOs:9 and 33 respectivally).

FIG. 18 is comparative figures of two nucleotide sequences of MF-6 PCR fragment (SEQ ID NOs:37 and 38 respectivally).

FIG. 19 is comparative figures of nucleotide sequences of MF-1 cDNA and MF-2 cDNA.

FIG. 20 is comparative figures of nucleotide sequences of MF-3 cDNA and MF-4 cDNA.

FIG. 21 shows amino acid sequences of MF-1 overlapping peptides.

FIG. 23 is comparative figures of MF-1 cDNA and MF-1 genomic DNA (SEQ ID NOs:18 and 19 respectivally).

BEST MODE FOR CARRYING OUT THE INVENTION

Figure 1:
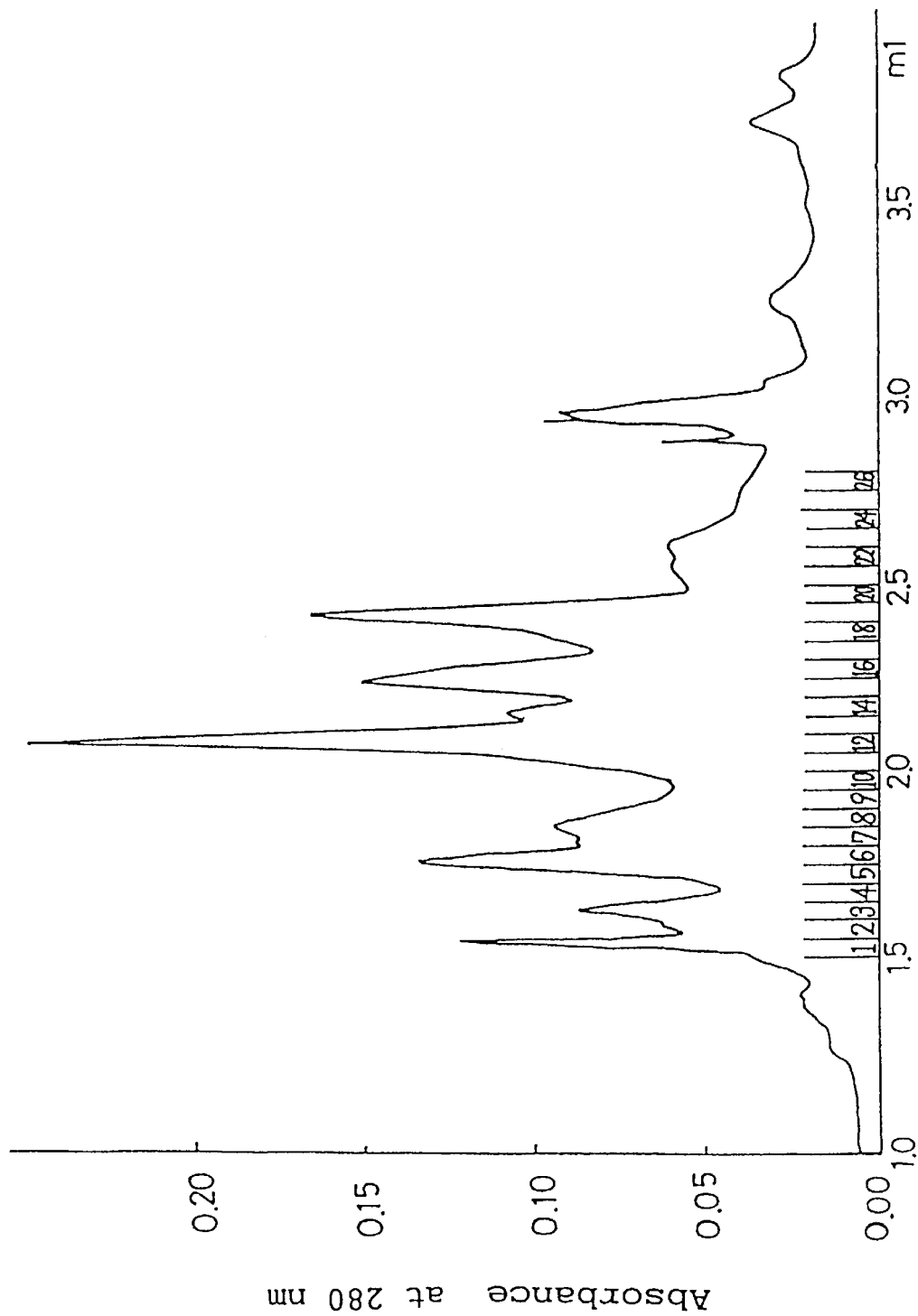
FIG. 1 is a graph showing chromatographic analysis by Mono Q of a partially purified, crude antigen 2782 of Malassezia.

The present invention is hereinafter described in detail.

(1) Purified Antigenic Protein of Present Invention and Functionally Equivalent Antigenic Proteins Thereof The antigenic protein of the present invention is a substantially pure, isolated, antigenic protein from fungi of the genus Malassezia, which is, in some cases, hereinafter simply referred to as "isolated and purified antigenic protein from Malassezia" or more simply "purified, antigenic protein", characterized in that the antigenic protein has a binding ability to IgE antibodies from patients with allergoses. Here, the phrase "substantially pure, isolated" as used herein means that the protein of interest is substantially homogenous as a protein, wherein the protein does not substantially contain other impurity proteins, and wherein the isolated protein is recognized as a single substance as determined by SDS-PAGE and isoelectric electrophoresis.

In addition, the purified, antigenic protein of the present invention is characterized in that the antigenic protein is a major allergen from Malassezia reactive to patients with allergoses showing a positive reaction in a skin test to a crude antigen of Malassezia.

Also, the purified, antigenic protein of the present invention is an antigenic protein present in the fungal cells of the genus Malassezia.

Additionally, the purified, antigenic protein of the present invention is characterized in that the antigenic protein has an epitope therein recognized by IgE antibodies from patients with allergoses, especially IgE antibodies from patients with Malassezia allergoses.

The strain which can be used in order to obtain the purified, antigenic protein of the present invention may be any strain, as long as the strain belongs to the genus Malassezia, and is exemplified, for instance, by *M. furfur* (*Malassezia furfur*) TIMM2782. The above strain is identified as *Malassezia furfur* TIMM2782 and deposited with an accession number FERM BP-5611 with National Institute of Bioscience and Human-Technology, Agency of Industrial Science and Technology, which is addressed at 1–3, Higashi 1-chome, Tsukuba-shi, Ibaraki-ken, Japan, zip code: 305; date of original deposit: Sep. 12, 1995; and date of transfer request to the International Deposit: Jul. 29, 1996.

The term "major allergen from Malassezia" referred in the present specification is defined as a purified, antigenic protein which is recognized by IgE antibodies, and reactive to not less than 50% of the patients with Malassezia allergoses, i.e. patients with allergoses with positive skin reaction to commercially available crude antigen extracts of Malassezia.

The phrase "binding ability to IgE antibodies from patients with allergoses" referred in the present specification means that significantly enhanced binding, in comparison with standard sera, can be obtained, as determined by RAST method using a $^{125}$I-labeled anti-IgE serum, or direct-RAST RIA method or ELISA method using an enzyme-labeled anti-IgE serum.

The isolated and purified, antigenic protein from Malassezia of the present invention has a molecular weight of from 10,000 to 100,000, as determined by SDS-PAGE, under reduced conditions or non-reduced conditions, and an isoelectric point of from 4 to 10 in a native state or in a denatured state with 8 M urea, and the isolated and purified, antigenic protein from Malassezia is present in the fungal cells of the genus Malassezia. Concrete examples thereof include MF-1, MF-2, MF-3, MF-4, MF-5, MF-6, MF-7, MF-8, MF-9, MF-10, MF-11, MF-12, MF-13, and the like.

The molecular weights, the isoelectric points, and the partial amino acid sequences of these purified, antigenic proteins will be described hereinbelow.

(I) MF-1 has a molecular weight, as determined by SDS-PAGE, of about 21 kDa under reduced conditions and about 40 kDa under non-reduced conditions, an isoelectric point of about 4.8 in a native state, and an isoelectric point of about 5.3 in a denatured state with 8 M urea, and contains an amino acid sequence as shown by SEQ ID NO:45 in Sequence Listing.

(II) MF-2 has a molecular weight, as determined by SDS-PAGE, of about 20 kDa under reduced conditions and about 40 kDa under non-reduced conditions, an isoelectric point of about 4.8 in a native state, and an isoelectric point of about 5.8 in a denatured state with 8 M urea, and contains amino acid sequences as shown by SEQ ID NO:46, SEQ ID NO:47, and SEQ ID NO:48, and its N-terminus is blocked.

(III) MF-3 has a molecular weight, as determined by SDS-PAGE, of about 27 kDa under reduced conditions and also about 27 kDa under non-reduced conditions, an isoelectric point of about 5.2 in a native state, and an isoelectric point of about 6.5 in a denatured state with 8 M urea, and contains amino acid sequences as shown by SEQ ID NO:49, SEQ ID NO:50, and SEQ ID NO:51, and its N-terminus is blocked.

(IV) MF-4 has a molecular weight, as determined by SDS-PAGE, of about 26 kDa under reduced conditions and also about 26 kDa under non-reduced conditions, an isoelectric point of about 5.2 in a native state, and an isoelectric point of about 6.3 in a denatured state with 8 M urea, and contains an amino acid sequence as shown by SEQ ID NO:52.

(V) MF-5 has a molecular weight, as determined by SDS-PAGE, of about 66 kDa under reduced conditions, and an isoelectric point of about 6.1 in a denatured state with 8 M urea, and contains an amino acid sequence as shown by SEQ ID NO:53.

(VI) MF-6 has a molecular weight, as determined by SDS-PAGE, of about 43 kDa under reduced conditions, and an isoelectric point of about 6.2 in a denatured state with 8 M urea, and contains an amino acid sequence as shown by SEQ ID NO:54.

(VII) MF-7 has a molecular weight, as determined by SDS-PAGE, of about 15 kDa under reduced conditions, and an isoelectric point of about 6.0 in a denatured state with 8 M urea, and contains an amino acid sequence as shown by SEQ ID NO:55.

(VIII) MF-8 has a molecular weight, as determined by SDS-PAGE, of about 30 kDa under reduced conditions, and an isoelectric point of about 5.4 in a denatured state with 8 M urea, and its N-terminus is blocked.

(IX) MF-9 has a molecular weight, as determined by SDS-PAGE, of about 40 kDa under reduced conditions, and an isoelectric point of about 5.3 in a denatured state with 8 M urea.

(X) MF-10 has a molecular weight, as determined by SDS-PAGE, of about 44 kDa under reduced conditions, and an isoelectric point of about 6.2 in a denatured state with 8 M urea, and contains an amino acid sequence as shown by SEQ ID NO:56.

(XI) MF-11 has a molecular weight, as determined by SDS-PAGE, of about 45 kDa under reduced conditions, and an isoelectric point of about 6.4 in a denatured state with 8 M urea, and its N-terminus is blocked.

(XII) MF-12 has a molecular weight, as determined by SDS-PAGE, of about 100 kDa under reduced conditions, and an isoelectric point of about 5.0 in a denatured state with 8 M urea.

(XIII) MF-13 has a molecular weight, as determined by SDS-PAGE, of about 16 kDa under reduced conditions, and an isoelectric point of about 8.1 in a native state, and contains an amino acid sequence as shown by SEQ ID NO:57.

The isolated and purified, antigenic protein from Malassezia of the present invention may be any protein, as long as the antigenic protein is from Malassezia and recognized as an antigen of mammals, including humans, and the antigenic protein is not limited to the 13 kinds of purified, antigenic proteins exemplified above.

Furthermore, diagnoses using these purified, antigenic proteins yield results correlating to those of diagnoses based on skin tests and RAST method using extracts of crude conventional antigen of Malassezia. Specifically, many of the patients showing positive reaction in a skin test using crude antigens also show positive reaction for IgE antibody titer against the crude antigens of Malassezia. Not less than 50% of the patients with positive reaction for IgE antibody titer against crude antigens have high IgE antibody titers against the above-described isolated and purified, antigenic protein of the present invention (see Tables 2 and 3 in Examples set forth below).

Also, when administered to patients with Malassezia allergoses, the purified, antigenic protein of the present invention is capable of lowering the allergic response to Malassezia fungi in patients with Malassezia allergoses administered therewith.

Moreover, the present invention provides functionally equivalent antigenic proteins having properties immunologically equivalent to those of the above-described purified, antigenic protein. For example, as functional equivalents having properties immunologically equivalent to those of the above-described 13 kinds of purified, antigenic proteins, functional equivalents of various strains of *M. furfur*, and functional equivalents of fungal species of the genus Malassezia other than *M. furfur*, are also encompassed in the scope of the present invention. Specifically, MF-2 is homologous to a peroxisome membrane protein PMP-20 [L. Garrard et al., *J. Biol. Chem.*, 23, 13929–13937 (1989)], and proteins from Malassezia having similar immunological properties are encompassed in the scope of the present invention. Also, MF-3 and MF-4, which are different proteins, are both homologous to iron/manganese-superoxide dismutase [T. Matsumoto et al., *Biochemistry*, 30, 3210–3216 (1991); M. L. Ludwig et al., *J. Mol. Biol.*, 219, 335–358 (1991)]; and MF-5, MF-6, and MF-13 are homologous to dihydrolipoamide dehydrogenase (DLDH), malate dehydrogenase (MDH), and cyclophilin, respectively, and proteins from Malassezia having similar immunological properties are encompassed in the scope of the present invention.

Incidentally, the purified, antigenic protein of the present invention can be modified, derivatized, or bound to polyethylene glycol (PEG) by the PEG method [Wie et al., *Int. Arch. Allergy Appl. Immunol.*, 64, 84–99 (1981)], in order to enhance stability and/or desired reactivity, i.e. to enhance antigen-antibody specific binding for diagnostic purposes, or to attenuate allergic reaction or eliminate enzymatic activity for therapeutic purposes. Protein modifications include pyridylethylation, reduction, alkylation, acylation, chemical coupling to suitable carriers, gentle formalin treatment, and guanidine hydrochloride treatment.

(2) Antigenic Fragment of Present Invention

The antigenic fragment of the present invention is an antigenic fragment derived from the purified, antigenic protein, characterized in that the antigenic protein has an antigenic epitope contained in the above-described purified, antigenic protein. The antigenic fragments are exemplified by, for instance, antigenic fragments derived from purified, antigenic protein containing at least one antigenic epitope contained in MF-1, MF-2, MF-3, MF-4, MF-5, MF-6, MF-7, MF-8, MF-9, MF-10, MF-11, MF-12, MF-13, and the like, among which preference is given to those containing at least one T cell epitope or B cell epitope. The antigenic fragments of the present invention include fragments derived from the purified, antigenic protein of Malassezia. The fragments cause immune responses in mammals, especially in humans, for instance, minimum levels of stimulation of IgE production, IgE binding, induction of IgG and IgM antibody production, and T cell proliferation, and/or lymphokine secretion, and/or induction of T cell anergy.

When using the antigenic fragment of the present invention for therapeutic purposes, it is desired that the antigenic fragment is weak in activation of T cell response, or induces T cell anergy. Also, it is preferred that the antigenic fragment of the present invention does not substantially have a binding ability to IgE antibodies specific to Malassezia fungi, or even when the antigenic fragment is bound to the IgE antibody, the binding is at a level where no mediators, such as histamine, are released from mast cells or basophiles. In other words, it is preferred that even when binding to IgE antibodies occurs, the antigenic fragment binds to IgE antibodies at levels substantially lower than those for the purified, antigenic proteins from Malassezia. As described above, the antigenic fragment of the present invention preferably has a lower activity of activation in IgE-mediated immune response than that of the purified, antigenic proteins when used for therapeutic purposes. Therefore, when administered to patients with Malassezia allergoses, it is made possible to reduce allergic responses to Malassezia fungi in patients with Malassezia allergoses administered therewith.

The antigenicity of the antigenic fragment of the present invention can also be assessed in in vitro tests, such as RAST method, ELISA method, and histamine release tests, as well as in skin tests and intracutaneous tests to human volunteers.

The term "epitope" is a basic element or minimum unit recognized by receptors, especially antibodies, such as immunoglobulins, histocompatibility antigens, and T cell receptors, and contains amino acid sequences essential for receptor recognition. Other peptides resembling the amino acid sequence of an epitope, which can lower the allergic response to a Malassezia allergen, can also be used as epitopes. It is possible to design a Malassezia allergen peptide which is likely to change the allergic response to Malassezia fungi in patients with Malassezia allergoses when administered in sufficient amounts to the patients by currently available information on protein structures. It is also possible to design reagents or drugs which inhibit induction of allergic reaction in patients with Malassezia allergoses. For example, such drugs can be designed to bind to IgE antibodies against Malassezia allergens, and to thereby interfere with IgE-allergen binding and subsequent degranulation from mast cells.

Also, selection of peptides containing a T cell epitope can be carried out by culturing T lymphocytes obtained from an individual sensitive to a Malassezia allergen, i.e. individuals with IgE-mediated immune response, with a peptide from allergen, and then measuring stimulating activity for human T cell, i.e. blast formation activity, for instance, by means of determining whether or not T cell proliferation occurs in response to the addition of the peptide by measuring incorporation of tritiated thymidine into cells. Peptides containing a B cell epitope can be selected by reacting sera obtained from an individual sensitive to a Malassezia allergen with each peptide derived from the allergen, and measuring the amount of bound IgE to the peptide.

Peptides having immunological cross-reactivity to the fragment of the purified, antigenic proteins from Malassezia, including Malassezia allergens, for instance, those recognized by specific antibodies or T cells against the fragment thereof are encompassed in the antigenic fragment of the present invention.

In order to prepare the antigenic fragment of the present invention, an isolated and purified, antigenic protein, a starting material, is enzymatically digested with a protease, such as lysylendopeptidase or trypsin, or cleaved by chemical treatment with agents such as cyanogen bromide, after which a fragment having a desired antigenicity is isolated and purified by known methods of protein purification. It is also possible to express and prepare the desired antigenic fragment using a portion of the gene encoding an antigenic protein derived from Malassezia. Further, it can be also prepared by chemical synthesis utilizing peptide synthesis technology based on information on the chemical structure of the antigenic fragment.

In addition, amino acid substitution, insertion and deletion can be carried out using genetic engineering techniques and chemical synthesis techniques. For example, to enhance stability and/or enhance the desired reactivity, the antigenic fragment of the present invention may be derivatized, or modified by deletion, insertion, substitution or addition of at least one amino acid. The modified protein or peptide of the present invention can also be modified by replacing an amino acid with a D-amino acid, a non-natural amino acid, or a non-natural amino acid analogue, or by adding these amino acids or analogues. The antigenic fragment of the present invention can also be chemically modified by binding with polyethylene glycol. Modifications of the antigenic fragment include reduction, alkylation, acylation, and chemical coupling to suitable carriers.

The antigenic fragment thus obtained can be determined and isolated by measuring the induction of immune responses, including activation of T cell response, induction of T cell anergy, binding with antibody, and the like.

Next, the method for producing the purified, antigenic protein of the present invention will be described below. Conventionally used crude antigens have been lyophilized products of culture filtrates, or purified products obtained from cultured cells by very limited means of purification, such as disrupting the cells by a suitable method to obtain an extract, and then subjected to precipitation with ammonium sulfate and lyophilizing. The present inventors have also attempted purification using such crude antigens as starting materials by commonly used methods of protein purification, e.g., gel filtration, ion exchange and other chromatographies, but they have not succeeded in isolation of a single pure, antigenic protein using these techniques only.

The isolated and purified, antigenic protein from Malassezia of the present invention can be isolated by fractionating a crude antigen prepared from Malassezia cells as a starting material by an appropriate combination of effective separation methods using ion exchange chromatography, chelate resin chromatography, hydrophobic chromatography, gel filtration chromatography, and the like, then measuring the binding of each fraction with an IgE antibody of patient sera by RAST method, immunoblotting, and the like, to search for a protein that binds to the IgE antibody in the allergic patient sera, or to search for a protein that induces immune responses, including activation of T cell response, T cell anergy, and the like, by various methods using patient lymphocytes.

Specifically, a fungus of the genus Malassezia, such as *M. furfur*, is cultured under appropriate temperature, aeration and other conditions using a medium containing nutrients suitable for the growth of Malassezia fungi, supplemented with olive oil or Tween 40 or Tween 60, such as Dixon medium. The obtained cells are disrupted by a suitable method to yield an extract. From this extract, the antigenic protein can be purified using separation means, including ion exchange chromatography, chelate resin chromatography, and hydrophobic chromatography. In other words, the antigenic protein can be isolated as a high-purity protein using an appropriate combination of various known methods of peptide and protein purification, such as ion exchange chromatography, hydrophobic chromatography, gel filtration chromatography, chelate resin chromatography, electrophoresis, and affinity chromatography using a resin coupled with an antibody specific to an antigenic protein derived from Malassezia or an antigenic fragment thereof. The antigenic protein contained in the culture filtrate can be isolated in the same manner.

Specifically, as shown in Examples below, a group of a large number of well-resembled proteins that are inseparable on the basis of molecular weight can be separated from each other by combining ion exchange chromatography, utilizing the differences in isoelectric points; hydrophobic chromatography, utilizing differences in hydrophobicity; chelate resin chromatography, utilizing differences in chelating abilities with metals; gel filtration chromatography, utilizing the molecular weight differences, and the like. These findings have been unexpected from the findings concerning differences of the antigenic proteins on the basis of the molecular weight shown by conventional SDS-PAGE immunoblotting. For example, MF-1 and MF-2 are almost identical in terms of molecular weight, and they are mutually inseparable by conventional SDS-PAGE. It is also impossible to mutually separate MF-3 and MF-4 on the basis of molecular weight.

Concrete examples of the combinations of various separation means are given below, as exemplified by the following steps:

Step a: Centrifuging a cell disruption extract of a cultured Malassezia fungus, lyophilizing the resulting supernatant, and thereafter subjecting the lyophilized product to anionic exchange chromatography (for instance, DEAE-cellulose column chromatography, manufactured by Wako Pure Chemical Industries) to obtain a fraction eluted with 0.1 M NaCl;

Step b: Concentrating the eluted fraction obtainable in Step a using an ultrafiltration membrane (MW 10,000), and thereafter subjecting the resulting concentrate to gel filtration chromatography (for instance, Sephacryl S-200HR column chromatography, manufactured by Pharmacia) to obtain a fraction eluted at molecular weights of 30,000 to 50,000;

Step c: Concentrating the eluted fraction obtainable in Step b using an ultrafiltration membrane (MW 10,000), and thereafter subjecting the concentrate to gel filtration chromatography (for instance, Sephadex G-75 Superfine column chromatography, manufactured by Pharmacia) to obtain a fraction eluted at a molecular weight of about 40,000;

Step d: Subjecting the eluted fraction obtainable in Step c to zinc chelating chromatography (for instance, Zinc Chelating Sepharose fast flow column chromatography, manufactured by Pharmacia), and further subjecting the resulting effluent fraction to copper chelate chromatography to obtain an effluent fraction or a fraction eluted at pH about 4;

Step e: Concentrating the effluent fraction or the fraction eluted at pH about 4 obtainable in Step d, and thereafter purifying the resulting concentrate by gel filtration chromatography (for instance, Sephadex G-75 Superfine column chromatography, manufactured by Pharmacia) to obtain a fraction eluted at a molecular weight of about 40,000; and Step f: Further purifying the eluted fraction obtainable in Step e by ion exchange chromatography of Mono Q.

Alternatively, there may be included the following steps as one example.

Step a: Centrifuging a cell disruption extract of a cultured Malassezia fungus; lyophilizing the resulting supernatant, and thereafter subjecting the lyophilized product to anionic exchange chromatography (for instance, DEAE-cellulose column chromatography) to obtain a fraction eluted with 0.1 M NaCl;

Step b: Concentrating the eluted fraction obtainable in Step a using an ultrafiltration membrane (MW 10,000), and thereafter subjecting the resulting concentrate to gel filtration chromatography (for instance, Sephacryl S-200HR column chromatography) to obtain a fraction eluted at molecular weights of 30,000 to 50,000;

Step c: Concentrating the eluted fraction obtainable in Step b using an ultrafiltration membrane (MW 10,000), and thereafter subjecting the resulting concentrate to gel filtration chromatography (for instance, Sephadex G-75 Superfine column chromatography) to obtain a fraction eluted at a molecular weight of about 40,000;

Step d: Subjecting the eluted fraction obtainable in Step c to zinc chelating chromatography (for instance, Zinc Chelating Sepharose fast flow column chromatography) to obtain a fraction eluted at pH about 5; and Step g: Concentrating the eluted fraction obtainable in Step d, and thereafter purifying the resulting concentrate by subjecting the concentrate to gel filtration chromatography (for instance, Sephadex G-75 Superfine column chromatography).

Next, the method of the present invention will be explained in further detail by taking, as examples, the production methods for purified, antigenic proteins (MF-1, MF-2, MF-3, MF-4, and MF-13) of the present invention. However, the following steps are simply examples, without intending to limit the scope of the present invention thereto.

1. Production Example of MF-1

This method comprises centrifuging a cell disruption extract of cultured *M. furfur* (*Malassezia furfur*) TIMM 2782 cells, lyophilizing the resulting supernatant, and thereafter subjecting the lyophilized product to anionic exchange chromatography (for instance, DEAE-cellulose column chromatography) to obtain a fraction eluted with 0.1 M NaCl; concentrating the resulting eluted fraction using an ultrafiltration membrane (MW 10,000), and thereafter subjecting the resulting concentrate to gel filtration chromatography (for instance, Sephacryl S-200HR column chromatography) to obtain a fraction eluted at molecular weights of 30,000 to 50,000; concentrating the resulting eluted fraction using an ultrafiltration membrane (MW 10,000), and thereafter subjecting the resulting concentrate to gel filtration chromatography (for instance, Sephadex G-75 Superfine column chromatography) to obtain a fraction eluted at a molecular weight of about 40,000; subjecting the resulting eluted fraction to zinc chelating chromatography (for instance, Zinc Chelating Sepharose fast flow column chromatography), and further subjecting the resulting effluent fraction to copper chelate chromatography to obtain a fraction eluted at a pH of about 4; and concentrating the resulting eluted fraction, and thereafter purifying the concentrate by gel filtration chromatography (for instance, Sephadex G-75 Superfine column chromatography) to obtain a fraction eluted at a molecular weight of about 40,000.

2. Production Example MF-2

This method comprises centrifuging a cell disruption extract of cultured *M. furfur* (*Malassezia furfur*) TIMM 2782 cells, lyophilizing the resulting supernatant, and thereafter subjecting the lyophilized product to anionic exchange chromatography (for instance, DEAE-cellulose column chromatography) to obtain a fraction eluted with 0.1 M NaCl; concentrating the resulting eluted fraction using an ultrafiltration membrane (MW 10,000), and thereafter subjecting the resulting concentrate to gel filtration chromatography (for instance, Sephacryl S-200HR column chromatography) to obtain a fraction eluted at molecular weights of 30,000 to 50,000; concentrating the resulting eluted fraction using an ultrafiltration membrane (MW 10,000), and thereafter subjecting the resulting concentrate to gel filtration chromatography (for instance, Sephadex G-75 Superfine column chromatography) to obtain a fraction eluted at a molecular weight of about 40,000; subjecting the resulting eluted fraction to zinc chelating chromatography (for instance, Zinc Chelating Sepharose fast flow column chromatography) to obtain a fraction eluted at a pH of about 5; and concentrating the resulting eluted fraction, and thereafter purifying the resulting concentrate by gel filtration chromatography (for instance, Sephadex G-75 Superfine column chromatography).

3. Production Example MF-3

This method comprises centrifuging a cell disruption extract of cultured *M. furfur* (*Malassezia furfur*) TIMM 2782 cells, lyophilizing the resulting supernatant, and thereafter subjecting the lyophilized product to anionic exchange chromatography (for instance, DEAE-cellulose column chromatography) to obtain a fraction eluted with 0.1 M NaCl; concentrating the resulting eluted fraction using an ultrafiltration membrane (MW 10,000), and thereafter subjecting the resulting concentrate to gel filtration chromatography (for instance, Sephacryl S-200HR column chromatography) to obtain a fraction eluted at molecular weights of 30,000 to 50,000; concentrating the resulting eluted fraction using an ultrafiltration membrane (MW 10,000), and thereafter subjecting the resulting concentrate to gel filtration chromatography (for instance, Sephadex G-75 Superfine column chromatography) to obtain a fraction eluted at a molecular weight of about 40,000; subjecting the resulting eluted fraction to zinc chelating chromatography (for instance, Zinc Chelating Sepharose fast flow column chromatography) to obtain an effluent fraction, and further subjecting the effluent fraction to copper chelate chromatography; concentrating the resulting effluent fraction, and thereafter purifying the resulting concentrate by gel filtration chromatography (for instance, Sephadex G-75 Superfine column chromatography) to obtain a fraction eluted at a molecular weight of about 40,000; and further purifying the resulting fraction by anionic exchange chromatography of Mono Q.

4. Production Example MF-4

This method comprises centrifuging a cell disruption extract of cultured *M. furfur* (*Malassezia furfur*) TIMM 2782 cells, lyophilizing the resulting supernatant, and thereafter subjecting the lyophilized product to anionic exchange chromatography (for instance, DEAE-cellulose column chromatography) to obtain a fraction eluted with 0.1 M NaCl; concentrating the resulting eluted fraction using an ultrafiltration membrane (MW 10,000), and thereafter subjecting the resulting concentrate to gel filtration chromatography (for instance, Sephacryl S-200HR column chromatography) to obtain a fraction eluted at molecular weights of 30,000 to 50,000; concentrating the resulting eluted fraction using an ultrafiltration membrane (MW 10,000), and thereafter subjecting the resulting concentrate to gel filtration chromatography (for instance, Sephadex G-75 Superfine column chromatography) to obtain a fraction eluted at a molecular weight of about 40,000; subjecting the resulting eluted fraction to zinc chelating chromatography (for instance, Zinc Chelating Sepharose fast flow column chromatography) to obtain an effluent fraction, and further subjecting the effluent fraction to copper chelate chromatography; concentrating the resulting effluent fraction, and thereafter purifying the resulting concentrate by gel filtration chromatography (for instance; Sephadex G-75 Superfine column chromatography) to obtain a fraction eluted at a molecular weight of about 40,000; and further purifying the resulting fraction by anionic exchange chromatography of Mono Q.

5. Product Example MF-13

This method comprises centrifuging a cell disruption extract of cultured *M. furfur* (*Malassezia furfur*) TIMM 2782 cells, lyophilizing the resulting supernatant, and thereafter subjecting the lyophilized product to anionic exchange chromatography (for instance, DEAE-cellulose column chromatography) to collect a non-adsorbing fraction; subjecting the fraction to gel filtration chromatography (for instance, Superdex 75 pg) to obtain an eluted fraction with a molecular weight of not more than 20,000; subjecting the resulting fraction to SP cationic exchange chromatography to obtain a fraction eluted with 0.2 M NaCl; and further purifying the eluted fraction by gel filtration chromatography (for instance, Superdex 75 pg).

In addition, the antigenic protein derived from Malassezia of the present invention can be prepared as a recombinant protein by a method comprising isolating a gene encoding the protein by such methods as PCR based on the information on the amino acid sequence mentioned above, and inserting the genes into a vector by genetic engineering techniques so as to be expressed in *E. coil*, yeasts, molds, mammalian cells, and the like.

(3) Antibody or Antibody Fragment of Present Invention Against Purified, Antigenic Protein or Antigenic Fragment Thereof The antibody of the present invention against an isolated and purified, antigenic protein from Malassezia or an antigenic fragment thereof can be prepared by using as an antigen the purified, antigenic protein from Malassezia of the present invention, an antigenic fragment obtainable by enzymatic or chemical treatment of the above protein, or an antigenic peptide obtained by chemical synthesis. The antibody can be prepared by a conventional method including, e.g., a method comprising immunizing an animal, such as a rabbit, with the above-described protein or a fragment thereof together with an adjuvant to obtain an antiserum. Also, a monoclonal antibody can be prepared by fusing an antibody-producing B cell obtainable by immunizing an antigen and a myeloma cell, selecting a hybridoma for producing the desired antibody, and culturing this cell.

These antibodies can be used for production of an antigenic protein, measurement of titration of antigen extract of Malassezia allergen, and other purposes, as described later. As hybridomas mentioned above, a hybridoma for producing an M-40 monoclonal antibody against the antigenic protein MF-1 is named and identified as 5B4; a hybridoma for producing an M-3 monoclonal antibody against the antigenic protein MF-2 is named and identified as 8G11; and hybridoma for producing an M-1 monoclonal antibody against the against the antigenic protein MF-3 is named and identified as 10C1, and these hybridomas are deposited as FERM BP-5608, FERM BP-5609, and FERM BP-5610, respectively, with National Institute of Bioscience and Human-Technology, Agency of Industrial Science and Technology, addressed at 1–3, Higashi 1-chome, Tsukubashi, Ibaraki-ken, Japan (zip code: 305; date of original deposit: Sep. 12, 1995; date of transfer request to the International Deposit: Jul. 29, 1996.

(4) Diagnostic Agent of Present Invention Containing as Active Ingredient Purified, Antigenic Protein or Antigenic Fragment Thereof The present invention provides a diagnostic agent for allergoses or infectious diseases of which causative microorganisms are Malassezia fungi, using an isolated and purified, antigenic protein from Malassezia or an antigenic fragment having at least one antigenic epitope derived from the antigenic protein.

The term "allergoses of which causative microorganisms are Malassezia fungi" as used herein is defined as any allergoses of which causative microorganisms are Malassezia fungi, exemplified by atopic bronchial asthma, allergic rhinitis, allergic conjunctivitis, and atopic dermatitis. The term "infectious disease of which causative microorganisms are Malassezia fungi" is defined as any infectious disease of which causative microorganisms are Malassezia fungi, exemplified by tinea versicolor, Malassezia folliculitis, and dandruff.

The diagnostic agent for allergoses of the present invention is used as an intracutaneous reaction diagnostic agent and titration reagent for allergy diagnosis in allergoses caused by Malassezia fungi. When used as an intracutaneous reaction diagnostic agent, the isolated and purified, antigenic protein of the present invention or the antigenic fragment of the present invention is dissolved in a buffer and diluted in phenol-containing physiological saline by a conventional method.

Also, when used as a titration reagent for allergy diagnosis, it can be prepared by a conventional method. For example, the isolated and purified, antigenic protein of the present invention or the antigenic fragment of the present invention may be suitably dissolved and diluted in a Hanks' buffer to be used as a histamine release titration reagent. The method can be usually carried out by the following procedures. Specifically, a given volume of blood of a patient with allergoses or a given number of blood cells prepared by suspending a fraction of blood cells obtained by centrifugation is titrated with a solution of the mentioned purified, antigenic protein as a titration reagent by measuring the amount of histamine, which is released from basophiles, upon allergen stimulation by HPLC.

The isolated and purified, antigenic protein of the present invention or the antigenic fragment of the present invention can also be used for detection and diagnosis of Malassezia allergoses. For example, the diagnosis can be carried out by incubating blood or a blood component sampled from a patient whose sensitivity to Malassezia fungi is to assessed, together with the isolated and purified, antigenic protein of the present invention, and the like under appropriate conditions, and determining the degree of binding of the purified, antigenic protein with a blood component, including, for instance, antibody, T cell, B cell, or the like.

(5) Therapeutic Drug of Present Invention Containing as Active Ingredient Purified, Antigenic Protein or Antigenic Fragment Thereof The present invention provides a therapeutic drug for allergoses of which causative microorganisms are Malassezia fungi, including, as an active ingredient, an isolated and purified, antigenic protein from Malassezia or an antigenic fragment having at least one antigenic epitope.

The therapeutic drug of the present invention for allergoses can be administered via ordinary pathways, including, for instance, oral, intracutaneous, subcutaneous, intramuscular, and intraperitoneal pathways. Further, it can be used as percutaneous or transmucosal drugs, such as troches, sublingual tablets, eyedrops, intranasal sprays, poultices, creams, and lotions. Regarding the dosage and administration frequency of the therapeutic drug of the present invention for allergoses, the therapeutic drug can be suitably administered at a selected dose in a range of about not more than 20 mg per administration for an adult, depending on administration pathways, symptoms, and the like, and about once every week. Also, the therapeutic drug of the present invention for allergoses is useful not only as a therapeutic drug but also as a prophylactic drug for allergoses caused by Malassezia fungi. This is because it exhibits little or no anaphylaxis-inducing action and thus can be used safely in humans.

The therapeutic drug of the present invention for Malassezia allergoses contains as an active ingredient the above-described purified, antigenic protein or an antigenic fragment thereof, and is used as a therapeutic drug and prophylactic drug for various allergoses caused by Malassezia fungi.

The method of preparing the therapeutic drug of the present invention for allergoses is not particularly limited. For example, the purified, antigenic protein of the present invention or an antigenic fragment thereof having an epitope may be dried to a powder form and used as a hyposensitization therapeutic drug for allergoses caused by Malassezia fungi. In this case, it can be used alone, or in the form of a combination drug containing commonly used adjuvants and various additives, such as stabilizers, excipients, dissolution aids, emulsifiers, buffers, soothing agents, preservatives, and coloring agents, which are added by conventional methods as occasion demands. For example, a purified, antigenic protein in the powder form is dissolved in a phenol-supplemented physiological saline and used for a stock solution of an antigen for hyposensitization treatment.

In order to use it as a hyposensitization therapeutic drug, it is particularly advantageous that the therapeutic agent has an epitope that does not bind to IgE specific to Malassezia fungi, or even when the antigenic fragment is bound to the IgE, the binding is at a level where no histamine is released from mast cells or basophiles.

(6) Method for Quantitative Assay of Malassezia allergen

The present invention also provides a method for quantitative assay of the Malassezia allergen. The antibody against the purified, antigenic protein from Malassezia can be used for an immunological quantitative analysis of the Malassezia allergen usable in diagnoses of allergoses or infectious diseases of which causative microorganisms are Malassezia fungi.

It is easy to establish a method for quantitative assay by such methods as ELISA, using, the isolated and purified, antigenic protein of the present invention or the recombinant antigenic protein described later as a standard allergen and the antibody against the antigenic protein. Some Malassezia antigen extracts are commercially available, as described above. Also, because Malassezia fungi are commonly present on skins, including the human scalp, it is thought that commercially available house dust samples contain Malassezia allergens. It is extremely useful from diagnostic and therapeutic viewpoints to make known the Malassezia allergen contents in these commercially available antigen extracts.

(7) Recombinant Malassezia Antigenic Protein

The present invention provides a recombinant Malassezia antigenic protein (hereinafter, simply abbreviated as "recombinant antigenic protein" in some cases) having immunological properties equivalent to those of the pure, isolated and purified antigenic protein from Malassezia of Item (1) above, the purified, antigenic protein having a binding ability to an IgE antibody from patients with allergoses. Examples thereof include, for instance, a group of peptides comprising rMF-1 to -7 having amino acid sequences as shown by any one of SEQ ID NOs:2, 4, 6, 8, 10, or 14(here, the term "rMF-1 to -7" means MF-1 to -7 obtained by means of a genetic recombination method), and having immunological properties equivalent to those of the above peptides. Specifically, there are included in the present invention peptides having an entire or partial amino acid sequence as shown by any one of SEQ ID NOs:2, 4, 6, 8, 10, or 14; peptides including the above peptides having immunological properties equivalent to those of each of MF-1 to -7 corresponding to rMF-1 to -7; and peptides comprising amino acid sequences, wherein the antigenic protein results from at least one of deletion, addition, insertion or substitution of one or more amino acid residues in the amino acid sequence as shown by any one of SEQ ID NOs:2, 4, 6, 8, 10, or 14, or a partial sequence thereof, wherein the antigenic protein has immunological properties equivalent to those of each of MF-1 to -7 corresponding to rMF-1 to -7.

For instance, in a case where rMF-l is taken as an example, rMF-2 includes peptides which are antigenic proteins having immunological properties equivalent to those of MF-1, and having an entire or partial amino acid sequence as shown by SEQ ID NO:2 in Sequence Listing, or recombinant Malassezia antigenic proteins including the above peptide. Further, rMF-1 includes recombinant Malassezia antigenic proteins wherein the antigenic protein results from at least one of deletion, addition, insertion or substitution of one or more amino acid residues in the amino acid sequence as shown by SEQ ID NO:2 in Sequence Listing, or a partial sequence thereof, wherein the antigenic protein has immunological properties equivalent to those of each of MF-1 corresponding to rMF-1. The same can be said for rMF-2 to -7.

Here, the phrase "immunological properties equivalent" refers to those having equivalent Malassezia allergen activity, and the term "Malassezia allergen activity" refers to a binding ability to IgE antibodies from patients with allergoses, especially those with Malassezia allergoses.

The recombinant Malassezia antigenic protein of the present invention is obtained by, as a recombinant protein, selecting an appropriate vector so as to express the protein in bacteria, such as *Escherichia coli*, yeasts, such as budding yeasts, fungi, such as Aspergillus, insect cells, mammalian cells, and the like, by genetic engineering techniques using the gene of the present invention described later, preparing an expression vector, and introducing it into the above cells.

The recombinant Malassezia antigenic protein is, therefore, essentially free of other proteins from Malassezia.

Functional equivalents to the recombinant antigenic protein of the present invention may be obtained by modifying the recombinant antigenic protein by known methods using mutagenesis in a specific site of the DNA encoding the recombinant antigenic protein of the present invention. For example, substitution, insertion, deletion or addition of one or more bases on the polynucleotide described later enables to make substitution, insertion, deletion or addition of an amino acid residue. It is also possible to select a mutant retaining the biological activity.

Known methods of preparing the above mutants include a gapped duplex method [Nucleic Acids Research, 12, 24, 9441–9456 (1984)], a deletion method [Gene, 33, 103–119 (1985)], a PCR method [Gene, 102, 67–70 (1991)], uracil DNA methods [Methods in Enzymology, 154, 367–382 (1987); Proc. Natl. Acad. Sci. USA, 79, 7258–7262 (1982)], and a cassette mutation method [Gene, 24, 315–323 (1985)].

A tag group may be added to the peptide chain to facilitate the purification of the recombinant antigenic protein of the present invention or to increase its solubility. An example of the tag group includes polyhistidine, which can be purified by metal affinity chromatography. Additionally, if necessary, an endoprotease-specific recognition site may be introduced between the tag group and the desired peptide, and the resulting peptide is then treated with the protease, to facilitate the isolation of the peptide free of undesirable sequences.

In order to succeed in desensitization of a patient to a peptide antigen, it is necessary to increase the solubility of the peptide by adding a functional group to the peptide; or by not including a hydrophobic T cell epitope, a hydrophobic epitope, or a hydrophobic region in the peptide. Also, in order to aid appropriate antigen processing of the T cell epitope in the peptide antigen, an endoprotease recognition site may be prepared between two regions each containing at least one T cell epitope by the above-described recombination technique or synthesis. For example, a charged amino acid pair, such as LysLys or ArgArg, may be introduced between such regions within the peptide, and the resulting peptide is sensitive to cleavage with cathepsin and/or other trypsin-like enzymes, permitting production of a peptide fragment containing 1 or more T cell epitopes. In the addition, the charged amino acid residues as described above are also capable of increasing peptide solubility.

(8) Polynucleotide Encoding Recombinant Malassezia Antigenic Protein of Present Invention The present invention provides a polynucleotide encoding the recombinant Malassezia antigenic protein, or a polynucleotide encoding antigenic fragments thereof. The polynucleotides include polynucleotides each having an entire or partial sequence of the base sequence as shown N by any one of SEQ ID NOs:1, 3, 5, 7, 9, 11, or 13 in Sequence Listing, or a polynucleotide containing the polynucleotide, wherein each of the polynucleotide encoding rMF-1 to -7 or an antigenic protein having immunological properties equivalent to these proteins. In addition, there are also included polynucleotides encoding the recombinant Malassezia antigenic protein, wherein the polynucleotide results from at least one of deletion, addition, insertion or substitution of one or more bases in the base sequence having an entire or partial sequence of the base sequence as shown by any one of SEQ ID NOs:1, 3, 5, 7, 9, 11, or 13 in Sequence Listing. Further, there are included polynucleotides capable of hybridizing to the polynucleotide, wherein the polynucleotides each encodes an antigenic protein having Malassezia allergen activity.

For instance, in a case where rMF-1 is taken as an example, there are encompassed in the present invention polynucleotides each having an entire sequence of the base sequence as shown by SEQ ID NO:1 in Sequence Listing, or a partial sequence thereof, or a polynucleotide containing the polynucleotide, wherein each of the polynucleotide encoding rMF-1 or an antigenic protein having immunological properties equivalent to the protein. In addition, there are also encompassed in the present invention polynucleotides encoding the recombinant Malassezia antigenic protein, wherein the antigenic protein results from at least one of deletion, addition, insertion or substitution of one or more bases in a base sequence comprising an entire sequence as shown by SEQ ID NO:1 in Sequence Listing, or a partial sequence thereof. Further, there are included polynucleotides capable of hybridizing to the polynucleotide, wherein the polynucleotides each encodes an antigenic protein having Malassezia allergen activity. The same can be said for rMF-2 to -7.

The polynucleotide encoding a recombinant Malassezia antigenic protein can be obtained by a method as described below. It is possible to determine the N-terminal amino acid sequence or internal amino acid sequence of a Malassezia antigenic protein purified by a combination of various ordinary chromatographies, or that of a Malassezia antigenic protein purified by one-dimensional or two-dimensional electrophoresis. An oligonucleotide capable of encoding these amino acid sequences is synthesized and purified. Since one kind of amino acid is usually encoded by a number of codons, this oligonucleotide is a mixture prepared in consideration of all these codons. PCR is carried out to yield a polynucleotide of the present invention encoding the Malassezia antigenic protein, using this oligonucleotide and oligo(dT) as primers, and a cDNA synthesized from a total RNA or a genomic DNA extracted and purified from Malassezia fungi as a template. Oligonucleotides corresponding to two portions of an amino acid sequence for the antigenic protein may be used as primers for PCR, and PCR may be repeated in cases when the cDNA is not amplified by carrying out PCR once.

A polynucleotide containing the entire sequence or a polynucleotide capable of hybridizing to a polynucleotide encoding antigenic protein can easily be obtained by screening a cDNA library or genomic DNA;library prepared from the poly(A)$^+$ RNA or genomic DNA of Malassezia fungi, using the cDNA fragment obtained by the PCR reaction as a probe for DNA hybridization. The vector used for library preparation may be of phage origin or plasmid origin.

As another method, a cDNA clone encoding a Malassezia antigenic protein possessing Malassezia allergen activity can be obtained by preparing a cDNA expression library prepared from a poly(A)$^+$ RNA of Malassezia fungi, and screening a clone producing the proteins that binds to the IgE antibody derived from a patient with allergoses. The protein expressed by this cDNA clone is a Malassezia antigenic protein.

The genes encoding the epitopes from Malassezia described below are also encompassed in the present invention, having sequences with a less number of bases than those in the base sequence encoding the entire amino acid sequence of a Malassezia allergen. Generally, although the base sequence encoding an epitope is selected from base sequences encoding mature proteins, in some cases, it is desired that a base sequence is selected to contain the leader sequence portion of the present invention. The gene of the present invention may contain a linker sequence containing a restriction endonuclease recognition site and/or a sequence useful for the cloning, expression, or purification of the desired gene. Specifically, there are encompassed in the present invention polynucleotides encoding at least one B cell epitope and having a partial sequence of any one of the base sequences shown by SEQ ID NOs:1, 3, 5, 7, 9, 11, or 13 or polynucleotides resulting from partial modifications thereof by chemical or physical methods. For example, there are also encompassed in the present invention the corresponding polynucleotides possessed by M. furfur strains other than the strain used in the present invention or other fungi of the genus Malassezia, for example, M. pachydermatis and M. sympodialis. Specifically, M. furfur can be classified into five groups according to physiological properties ("Japanese Journal of Medical Mycology," Katsuhisa Uchida), each having a corresponding gene, and these genes are also encompassed in the present invention.

Moreover, the present invention includes polynucleotides capable of hybridizing to a polynucleotide having a base sequences shown by any one of SEQ ID NOs: 1, 3, 5, 7, 9, 11, or 13 or a base sequence encoding at least one B cell epitope. In the present invention, the term "capable of hybridizing" refers to a polynucleotide capable of hybridizing to another polynucleotide under the conditions shown below. A membrane on which DNA is immobilized is incubated with a probe at 50° C. for 12 to 20 hours in 6×SSC (1×SSC showing 0.15 M NaCl and 0.015 M sodium citrate, pH 7.0) containing 0.5% SDS, 0.1% bovine serum albumin (BSA), 0.1% polyvinylpyrrolidone, 0.1% Ficol 400, and 0.01% denatured salmon sperm DNA. After termination of the incubation, the membrane is washed until the signal from the immobilized DNA becomes distinguishable from the background firstly at 37° C. in 2×SSC containing 0.5% SDS, wherein the SSC concentration is changed to 0.1 fold the starting level, and wherein the temperature is changed to 50° C., and then the detection with a probe is carried out. By examining the activity owned by the protein encoded by the new DNA thus obtained in the same manner as above, whether or not the resulting DNA is the desired product can be confirmed.

Examples of polynucleotides capable of hybridizing to the gene of the present invention are shown below. The M. furfur TIMM2782 strain used herein has the MF-5 gene, as shown by SEQ ID N:9, and also a gene having the putative base sequence shown in FIG. 17, which has 90% or more homology to the MF-5 gene base sequence. The proteins encoded by the two genes each has homology to dihydrolipoamide dehydrogenase (DLDH) in the known protein. This strain also has the MF-6 gene as shown by SEQ ID NO:11; and also a gene having the putative base sequence as shown in FIG. 18, which has 90% or more homology to the MF-6 gene base sequence. The proteins encoded by the two genes each has homology to malate dehydrogenase (MDH) in the known protein. Moreover, the MF-1 gene (SEQ ID NO:1) and MF-2 gene (SEQ ID NO:3) of the present invention each has 60% or more homology in terms of base sequence (FIG. 19) and are mutually capable of hybridizing. The proteins encoded by the two genes each has homology to the peroxisome membrane protein PMP-20 from Candida boidinil. Also, the MF-3 gene (SEQ ID NO:5) and MF-4 gene (SEQ ID NO:7) of the present invention each has 60% or more homology in terms of base sequence (FIG. 20) and are mutually capable of hybridizing. The proteins encoded by the two genes each has homology to superoxide dismutase, and actually possess its enzyme activity. Accordingly, there are also encompassed in the present invention genes capable of hybridizing to the base sequences of the present invention encoding the recombinant antigenic protein, the genes being possessed by other fungi being a causative of allergy.

The gene of the present invention is not particularly limited, and it may be DNA or RNA, natural occurring or synthetic. Useful expression vectors containing promoters, enhancers and other expression regulatory elements suited for the expression of the gene of the present invention include, for example, application of those described in "Molecular Cloning, A Laboratory Manual, 2nd edition, J. Sambrook et al., published 1989 by Cold Spring Harbor Laboratory." Recombinant proteins expressed in mammalian, yeast, fungal or insect cells can undergo modifications, such as glycosylation and appropriate disulfide bonding. Available vectors suitable for expression in yeast cells include pYES2, YepSec, and the like, which are made available. For those expressed in insect cells, the baculovirus vector is commercially available (manufactured by Pharmingen, San Diego, Calif.), and for those expressed in mammalian cells, the pMSG vector is available (manufactured by Pharmacia).

In the case of those expressed in E. coli, the pTV118 vector, and the like may be used. Also, when pMAL, pSEM, or pGEX is used, the gene of the present invention can be expressed as a fusion protein with maltose-binding protein, with β-galactosidase, or with glutathione S-transferase, respectively. In the case of those expressed as a fusion protein, it is especially advantageous to introduce an enzyme recognition site at the location of the fusion joint between the carrier protein and the antigenic protein from Malassezia or a fragment thereof. After isolating and purifying as a fusion protein, the desired antigenic protein or fragment thereof can be selectively recovered by cleavage at the enzyme recognition site and by subsequent biochemical purification using conventional methods. The enzyme recognition sites include recognition sites of blood coagulation factor Xa or thrombin, and commercial products may be used as these enzymes. It is also possible to use vectors capable of inducing expression by IPTG, temperature, or the like.

Methods for introducing an expression vector into host cells are carried out by conventional methods, such as the calcium phosphate or calcium chloride co-precipitation method, the DEAE-dextran method, or the electroporation method.

(9) Antigenic Fragment of Present Invention

The present invention provides an antigenic fragment containing at least one antigen epitope, and there are also included functional equivalent derivatives thereof. Specifically, the antigenic fragment of the present invention contains an antigen epitope contained in a recombinant Malassezia antigenic protein comprising an amino acid sequence as shown by any one of SEQ ID NOs:2, 4, 6, 8, 10, or 14 in Sequence Listing. The antigenic fragment of the present invention is characterized in that the antigenic fragment does not have a binding ability to IgE antibody specific to Malassezia fungi, or even when the antigenic fragment binds to the IgE antibody, such binding is at a level where no histamine is released from mast cells or basophiles. The antigenic fragment of the present invention is also characterized in that the antigenic fragment binds to the IgE antibody at a substantially low level as compared to an antigenic protein from Malassezia. The antigenic fragment of the present invention is still also characterized in that the antigenic fragment has a lower activity of activation of IgE-mediated immune response than that of the antigenic protein.

The antigenic fragments of the present invention include antigenic fragments containing at least one T cell epitope.

Alternatively, there may be included antigenic fragments containing at least one B cell epitope, including, for instance, the antigenic fragments wherein the above B cell epitope is selected from the amino acid sequences as shown by one of SEQ ID NOs:42 to 44 in Sequence Listing. These antigenic fragments may be chemically synthesized by means of peptide synthesis techniques, or they may be obtained as recombinant Malassezia allergens from host cells transformed a plasmid having a part of the gene and expressing the desired epitope. For example, an antigenic protein may be prepared by optionally dividing the antigenic protein into non-overlapping fragments of a desired length, preferably overlapping peptide fragments of a desired length. The antigenicities of these peptide fragments are determined by assaying the binding of these peptide fragments to antibodies, or by assaying the effect on immune response, including activation of T cell responses, induction of T cell anergy, and the like.

(10) Antibody or Fragments Thereof Against Recombinant Malassezia Antigenic Protein of Present Invention or Antigenic Fragment Thereof The present invention provides an antibody or fragments thereof which specifically binds to the above recombinant Malassezia antigenic protein or antigenic fragments thereof. The antibody of the present invention can be obtained by a conventional method, and it may be polyclonal antibodies or monoclonal antibodies. The antibody fragment is not particularly limited, as long as it specifically binds to the above recombinant Malassezia antigenic protein or fragments thereof.

(11) Synthetic Oligonucleotide Probe or Synthetic Oligonucleotide Primer of Present Invention The present invention provides a synthetic oligonucleotide probe and a synthetic oligonucleotide primer capable of hybridizing to the polynucleotide of the present invention. For example, there are encompassed in the present invention probes or primers containing an entire or partial sequence of the base sequences as shown by any one of SEQ ID NOs:1, 3, 5, 7, 9, 11 or 13. The gene encoding proteins having equivalent functions can be isolated by hybridization method using the probe. This probe is prepared by, for instance, inserting the above gene or fragments thereof into an appropriate vector; introducing the vector into *E. coli* to replicate it; subsequently, extracting the replicated product from the disrupted cell solution with phenol or the like; cleaving it with a restriction endonuclease that recognizes the insertion site; carrying out electrophoresis, and cutting the desired product from the gel. The probe can also be prepared on the basis of the base sequences as shown by SEQ ID NOs:1, 3, 5, 7, 9, 11 or 13 by chemical synthesis using DNA synthesizers or by gene amplification technique using PCR. The above probe may be labeled with a radioisotope or fluorescent substance to increase its detection sensitivity upon use.

(12) Diagnostic Agent of Present Invention Containing as Active Ingredient Recombinant Malassezia Antigenic Protein or Antigenic Fragment Thereof The present invention provides a diagnostic agent for Malassezia allergoses or Malassezia infections, including, as an active ingredient, the recombinant Malassezia antigenic protein of the present invention or the antigenic fragments thereof. The term "Malassezia allergoses" as used herein is defined as any allergoses of which causative microorganisms are Malassezia fungi, exemplified by atopic bronchial asthma, allergic rhinitis, allergic conjunctivitis, and atopic dermatitis. The term "Malassezia infections" is defined as any infectious disease of which causative microorganisms are Malassezia fungi, exemplified by tinea versicolor, Malassezia folliculitis, and dandruff.

The diagnostic agent for allergoses of the present invention is used as an intracutaneous diagnostic agent and titration reagent for allergy diagnosis in allergoses caused by Malassezia fungi. When used as an intracutaneous diagnostic agent, the recombinant antigenic protein of the present invention or the antigenic fragment of the present invention is dissolved and diluted in phenol-containing physiological saline by a conventional method.

Also, when used as a titration reagent for allergy diagnosis, it can be prepared by a conventional method. For example, the recombinant antigenic protein of the present invention or the antigenic fragment of the present invention may be suitably dissolved and diluted in a Hanks' buffer to be used as a histamine release titration reagent. The method can be usually carried out by the following procedures. Specifically, a given volume of blood of a patient with allergoses or a given number of blood cells prepared by suspending a fraction of blood cells obtained by centrifugation is titrated with a solution of the mentioned recombinant antigenic protein as a titration reagent by measuring the amount of histamine, which is released from basophiles, upon allergen stimulation by HPLC.

The recombinant antigenic protein of the present invention or the antigenic fragment of the present invention can also be used for detection and diagnosis of Malassezia allergoses. For example, the diagnosis can be carried out by incubating blood or a blood component sampled from a patient whose sensitivity to Malassezia fungi is to assessed, together with the isolated and purified, antigenic protein of the present invention, and the like under appropriate conditions, and determining the degree of binding of the purified, antigenic protein with a blood component, including, for instance, antibody, T cell, B cell, or the like.

(13) Therapeutic Drug Containing Recombinant Malassezia Antigenic Protein or Antigenic Fragments of Present Invention as Active Ingredient The present invention provides a therapeutic drug for Malassezia allergoses or Malassezia infections including, as an active ingredient, the recombinant Malassezia antigenic protein or its antigenic fragments of the present invention. When the antigenic fragment from Malassezia is used for therapeutic purposes, it is preferred that the antigenic fragment binds to its IgE at concentrations substantially lower than the naturally occurring Malassezia allergen, and that mediators are not released from mast cells or basophiles upon binding. More preferably, the antigenic fragment exhibits activity to activate T cell response and/or is capable of inducing T cell anergy. A recombinant Malassezia antigenic protein or antigenic fragments thereof can be assessed in in vitro tests, such as RAST method, ELISA method, and histamine release tests, as well as in skin tests and intracutaneous tests in laboratory animals or human volunteers.

The recombinant antigenic protein of the present invention and the gene therefor can be utilized for therapeutic drugs for Malassezia allergoses. The therapeutic drug includes, as an active ingredient, the above-described recombinant Malassezia antigenic protein, antigenic fragments thereof, or a peptide having an epitope, so that it can be utilized for therapeutic drugs for various allergoses caused by Malassezia fungi. Moreover, the above-described gene can also be utilized for a therapeutic drug, in which case the gene is inserted into a vector expressible in a mammal and administered in the form of a DNA molecule or viral particles having the gene in a suitable viral vector. By this administration, tolerance can be induced to treat diseases.

The method of preparing the therapeutic drug of the present invention for allergoses is not particularly limited. For example, the recombinant Malassezia antigenic protein prepared by the above method, or antigenic fragments thereof, or a peptide having an epitope, or a DNA molecule having a vector to which the above gene is inserted may be dried to a powder form and used as a hyposensitization therapeutic drug for allergoses caused by Malassezia fungi. When the therapeutic drug of the present invention for allergoses is used as a hyposensitization therapeutic drug, it can be used alone, or in the form of a combination drug containing commonly used adjuvants and various additives, such as stabilizers, excipients, dissolution aids, emulsifiers, buffers, soothing agents, preservatives, and coloring agents, which are added by conventional methods as occasion demands. For example, a purified, recombinant antigenic protein in the powder form is dissolved in a phenol-supplemented physiological saline and used for a stock solution of an antigen for hyposensitization treatment.

The therapeutic drug of the present invention for allergoses can be administered via ordinary pathways, including, for instance, oral, intracutaneous, subcutaneous, intramuscular, and intraperitoneal pathways. Further, it can be used as percutaneous or transmucosal drugs, such as troches, sublingual tablets, eyedrops, intranasal sprays, poultices, creams, and lotions. Regarding the dosage and administration frequency of the therapeutic drug of the present invention for allergoses, the administration of the therapeutic drug can be suitably selected so that the therapeutic drug is administered at a dose of about not more than 20 mg per administration for an adult, depending on administration pathways, symptoms, and the like, and about once every week. Also, the therapeutic drug of the present invention for allergoses is useful not only as a therapeutic drug but also as a prophylactic drug for Malassezia allergoses. This is because it exhibits little or no anaphylaxis-inducing action and thus can be used safely in humans.

The therapeutic drug of the present invention for Malassezia allergoses contains as an active ingredient the above-described recombinant, antigenic protein or antigenic fragments thereof, and is used as a therapeutic drug and prophylactic drug for various Malassezia allergoses. In order to use it as a hyposensitization therapeutic drug, it is particularly advantageous that the therapeutic agent has an epitope that does not bind to IgE specific to Malassezia fungi, or even when the antigenic fragment binds to the IgE, the binding is at a level where no histamine is released from mast cells or basophiles.

The present invention is hereinafter described in more detail by means of the following working examples and comparative examples, without intending to limit the scope of the present invention thereto.

EXAMPLE 1

Isolation and Physicochemical Properties of Antigenic Protein from Malassezia 1-1) Preparation of Malassezia Partially Purified Crude Antigen 2782

The culture was obtained by subjecting the *M. furfur* TIMM2782 strain (FERM BP-5611) to shaking culture at 27° C. for 5 days in fifty (50) 500 ml conical flasks each containing 150 ml of Dixon medium (6.0% bacto malt extract broth, 2.0% Bacto Oxgall, 1.0% Tween 40, 0.25% glycerol α-monooleic acid). From the resulting culture, cells were harvested by centrifugation. The cells-were washed with a phosphate-buffered saline (PBS) five times, and the cells were then suspended in PBS in an amount double the wet weight of the cells, and disrupted and extracted by adding an equal amount of glass beads 0.5 mm in diameter, and using the MSK cell homogenizer (manufactured by B. Brown). The cell disruption extract obtained was centrifuged (18,000 rpm, 30 min), and the supernatant was obtained. The resulting supernatant was dialyzed against purified water and sterilized by filtration through a 0.45 $\mu$m membrane filter, followed by freeze-drying, to give about 900 mg of the Malassezia crude antigen 2782.

About 800 mg of the above Malassezia crude antigen 2782 was dissolved in a 0.05 M Tris-HCl buffer (pH 8.0) and subjected to ammonium sulfate salting-out. The fraction precipitated on ammonium sulfate from 50% to 90% saturation was collected by centrifugation, and the collected fraction was dissolved in a 0.05 M Tris-HCl buffer (pH 8.0), and the solution was subsequently dialyzed against the same buffer to give the Malassezia partially purified crude antigen 2782.

1-2) Screening for Antigenic Proteins from Malassezia

After freeze-drying, the Malassezia partially purified crude antigen 2782 was dissolved in a 0.1 M potassium phosphate buffer (pH 7.0) containing 2 M ammonium sulfate so as to give a 4 mg/ml solution. Thereafter, 100 $\mu$l of the solution was applied to a column of Phenyl Superose PC 1.6/5 (column volume: 0.1 ml, manufactured by Pharmacia), previously equilibrated with the same buffer (pH 7.0) containing 2 M ammonium sulfate, and the elution was carried out with the same 0.1 M buffer on a linear gradient from 2 M to 0 M ammonium sulfate. The antigenic protein-containing fraction obtained was dialyzed against a Bis-Tris buffer (pH 6.5), and the dialyzed fraction was then applied to a column of Mono Q PC 1.6/5 (column volume: 0.1 ml, manufactured by Pharmacia), and the elution was carried out with the same buffer on a linear gradient from 0 M to 0.3 M sodium chloride (FIG. 1, flow rate: 100 $\mu$l/min, detection: 280 nm). The eluate was divided into 26 fractions of 50 $\mu$l each, and the binding ability of IgE antibody was then examined for Fractions 1 through 20 by the Direct RAST (EIA) method using sera from patients.

Figure 2:
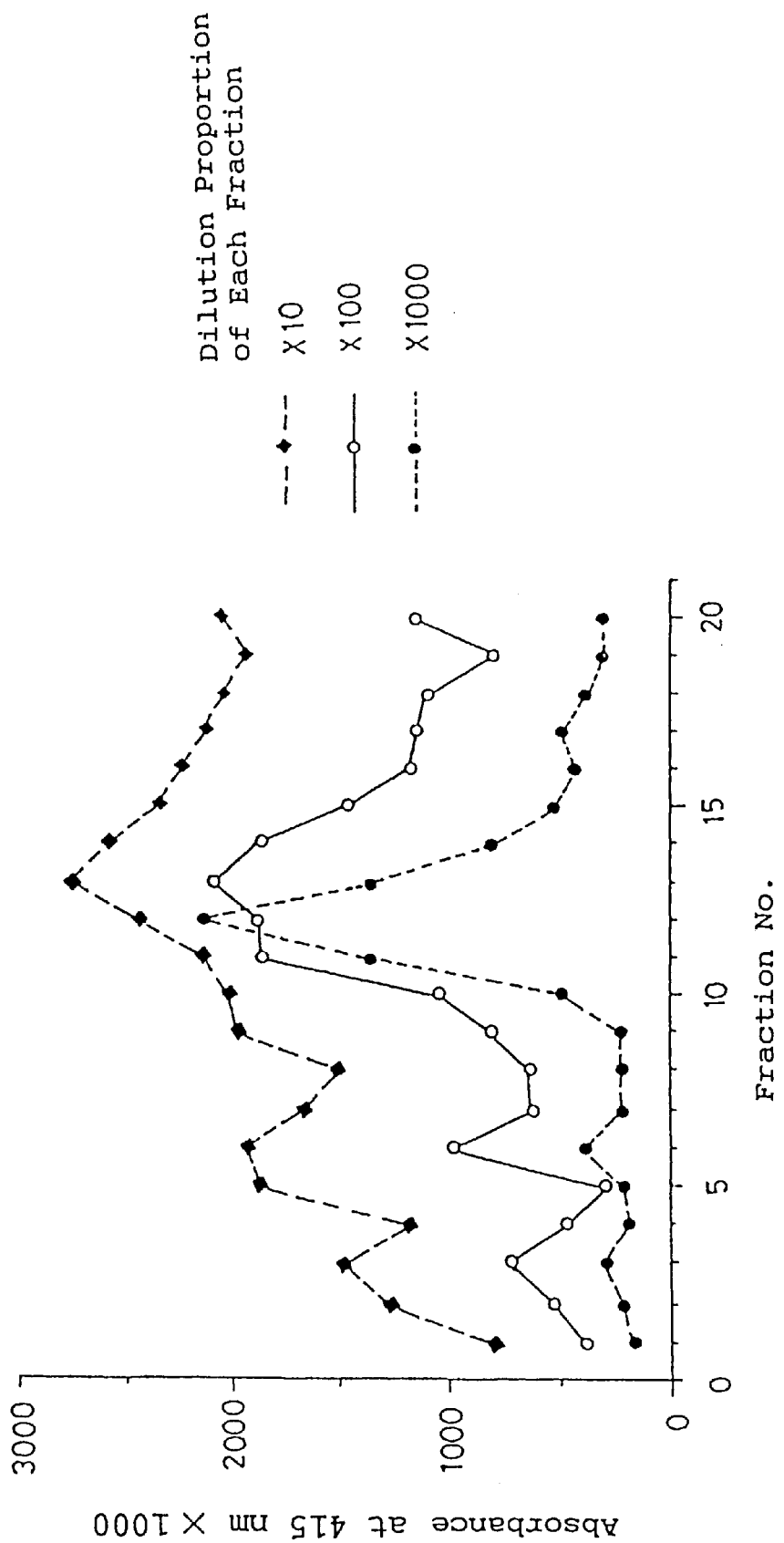
FIG. 2 is a graph showing the binding ability of Mono Q fractions of a partially purified, crude antigen 2782 of Malassezia with an IgE antibody in a patient serum.

Specifically, each fraction was diluted 10 folds, 100 folds, and 1,000 folds with a 0.1 M borate buffer (pH 8.0) containing 0.01% Tween 20, and 45 $\mu$l of each dilution was coupled to a paper disc activated with cyanogen bromide and subsequently blocked with ethanolamine. Thereafter, each disc was supplemented with 50 $\mu$l of a 5-fold dilution of pooled sera (collection of sera from 10 patients showing high values in RAST method), followed by reaction with a diluted β-galactosidase-labeled goat anti-human IgE antiserum. Thereafter, an enzyme substrate was added thereto, followed by absorbance measurement at 415 nm. The results are shown in FIG. 2. It is clear from FIG. 2 that there are a plurality of allergenic proteins. For example, a protein that binds to patient IgE is present in the neighborhoods of Fraction 6, and Fractions 12 and 13.

Figure 3:
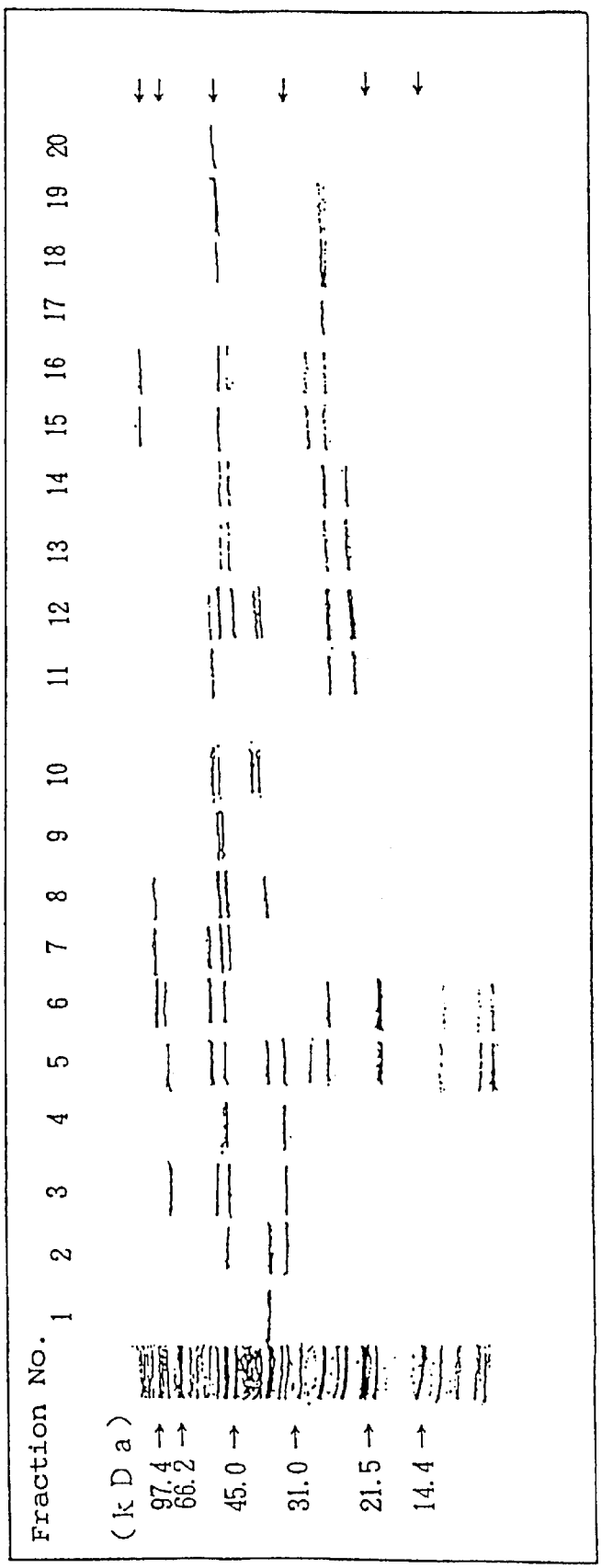
FIG. 3 is an electrophoretic analysis obtained by subjecting Mono Q fractions of a partially purified, crude antigen 2782 of Malassezia to SDS-PAGE, and then staining with CBB.

Separately, each fraction was subjected to SDS-PAGE, and it was stained with Coomassie Brilliant Blue (CBB) to detect proteins (FIG. 3), and the representative fractions were subjected to immunoblotting as described below.

Figure 4:
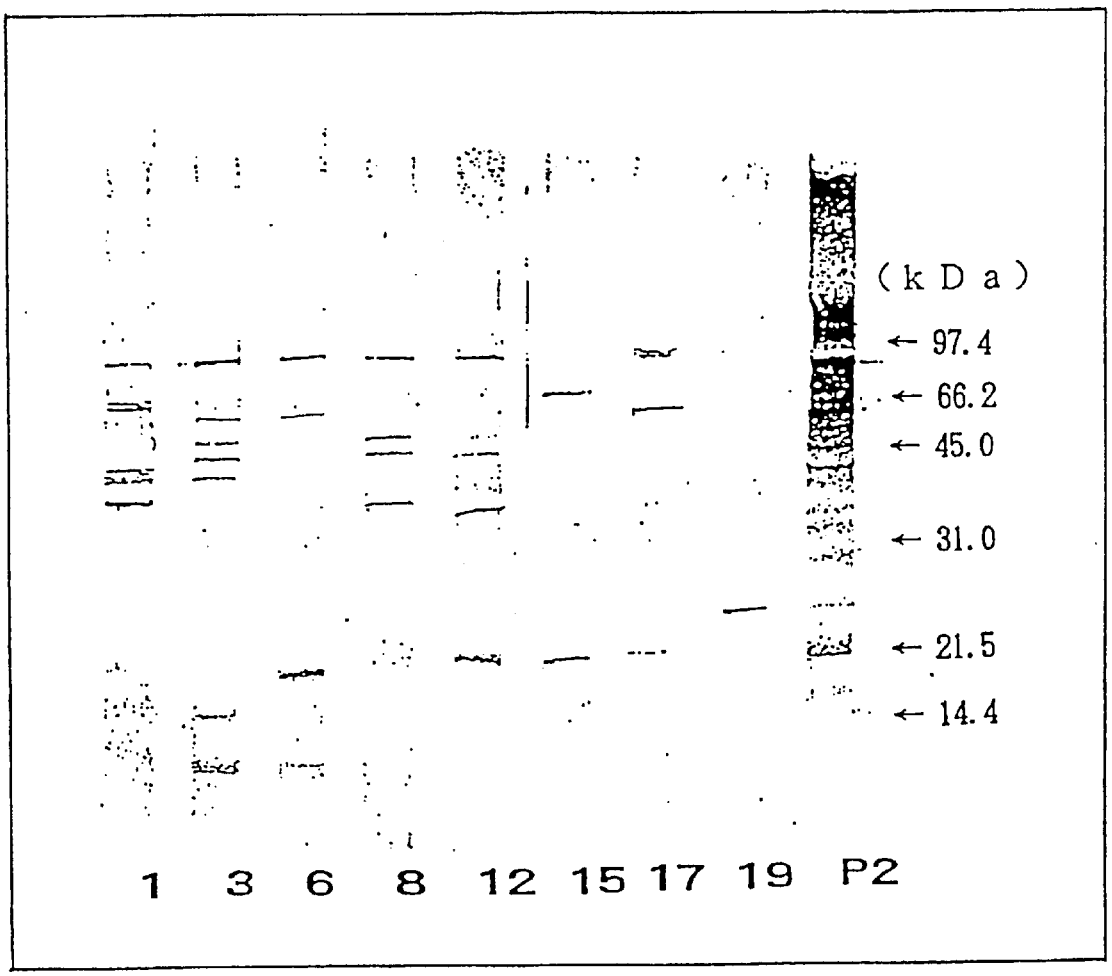
FIG. 4 is an electrophoretic analysis obtained by subjecting Mono Q fractions of a partially purified, crude antigen 2782 of Malassezia to SDS-PAGE, and then conducting immunoblotting.

Specifically, each fraction was subjected to SDS-PAGE, and it was then transferred onto a nitrocellulose membrane, blocked with 3% bovine serum albumin (BSA), and treated with pooled sera from patients. Thereafter, the fraction was reacted with a diluted alkaline phosphatase-labeled goat anti-human IgE antiserum, and an enzyme substrate was then added, followed by detection of allergenic protein. As a result, it is made clear from FIG. 4 that there are a plurality of allergenic proteins. For example, it is evident that Fraction 12 contains a protein detected in the neighborhood of 20 kDa on SDS-PAGE (isolated as an allergen MF-1), and the like, as allergenic proteins. It is also evident that Fraction 6 contains; an allergenic protein having a molecular weight of 20 kDa, nearly equal to that of Fraction 12 (isolated as an allergen MF-2), and another protein detected in the neighborhood of 80 kDa, and the like.

1-3) Isolation of Purified Antigenic Proteins MF-1, MF-2, MF-3, MF-4, and MF-13

After 0.25 mg of a freeze-dried product of the above-described Malassezia partially purified crude antigen 2782 was dissolved in 1 ml of a Bis-Tris buffer (pH 6.5) solution, the resulting solution was applied to a column of Mono Q HR 5/5 (column volume: 1 ml, manufactured by Pharmacia) in the same manner as the Mono Q chromatography described under Item 1-2) above, resulting in four peaks, namely Peak 1 (corresponding to Fractions 5 and 6 in FIG. 1), Peak 2 (corresponding to Fractions 10, 11, and 12 in FIG. 1), Peak 3 (corresponding to Fractions 15 and 16 in FIG. 1), and Peak 4 (corresponding to Fractions 18, 19, and 20 in FIG. 1). Each peak was subjected to gel filtration chromatography, hydrophobic chromatography, and finally ion exchange chromatography by Mono Q, to isolate pure antigenic proteins, wherein the protein named MF-2 was isolated from Peak 1, that named MF-1 isolated from Peak 2, that named MF-3 isolated from Peak 3, and that named MF-4 isolated from Peak 4. Separately, the Mono Q, non-adsorbed fraction of the Malassezia partially purified antigen 2782 was subjected to hydrophobic chromatography to isolate a pure antigenic protein named MF-13. It was confirmed that the five isolated proteins were Malassezia allergen proteins by examining their binding ability of IgE antibody by EIA method using the above-described pooled sera from patients.

Figure 5:
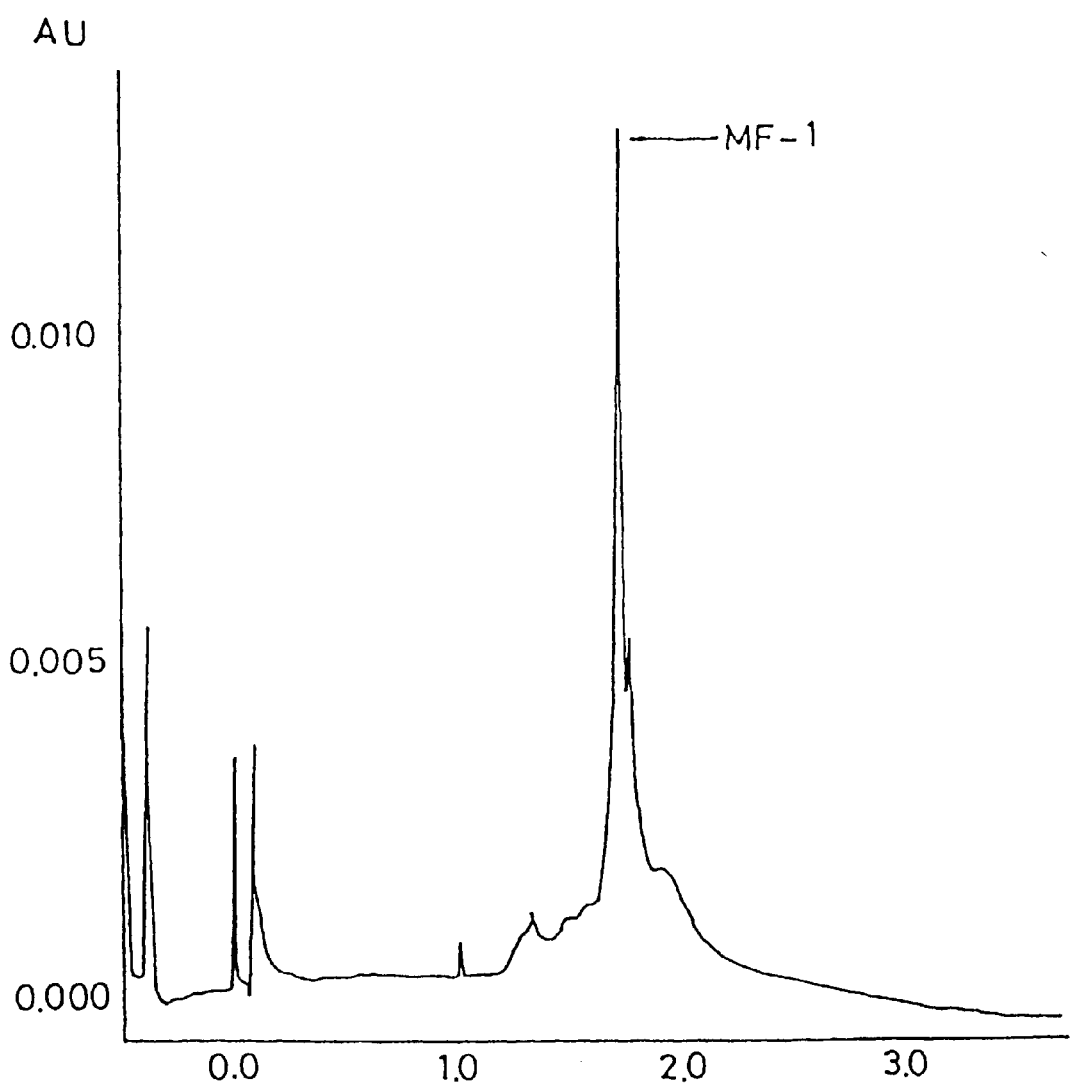
FIG. 5 is a chart showing an MF-1 peak by Mono Q chromatography.
Figure 6:
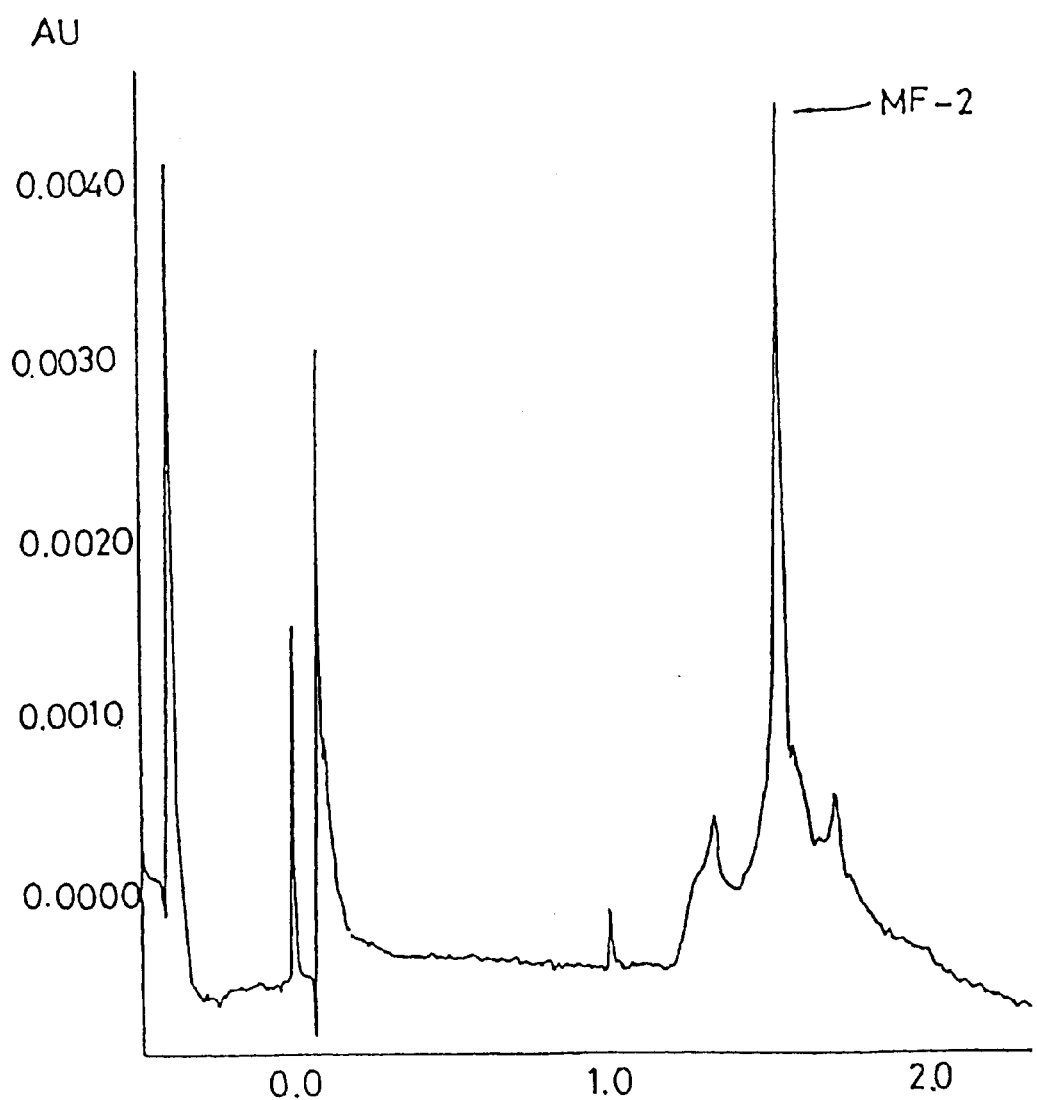
FIG. 6 is a chart showing an MF-2 peak by Mono Q chromatography.
Figure 7:
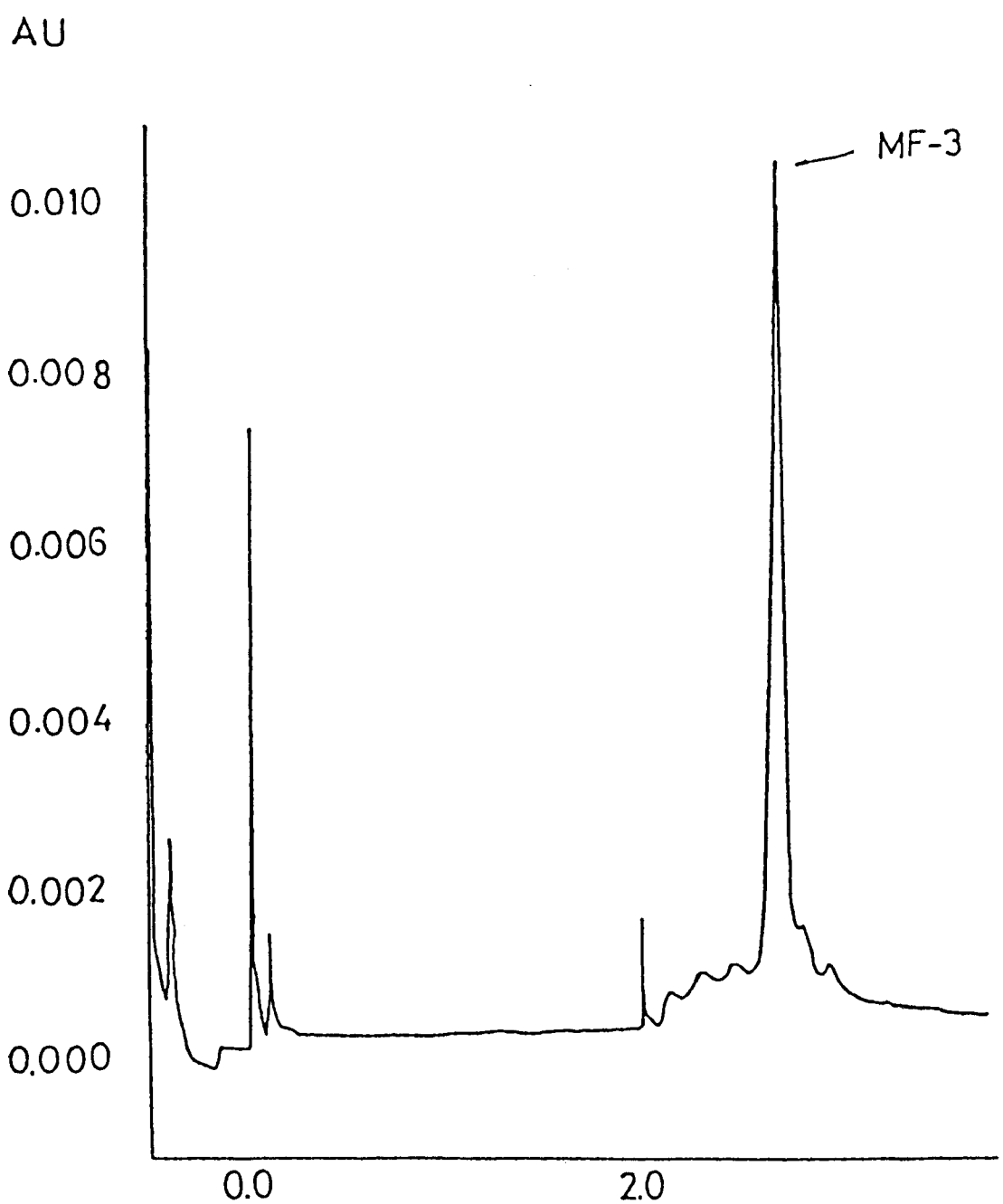
FIG. 7 is a chart showing an MF-3 peak by Mono Q chromatography.
Figure 8:
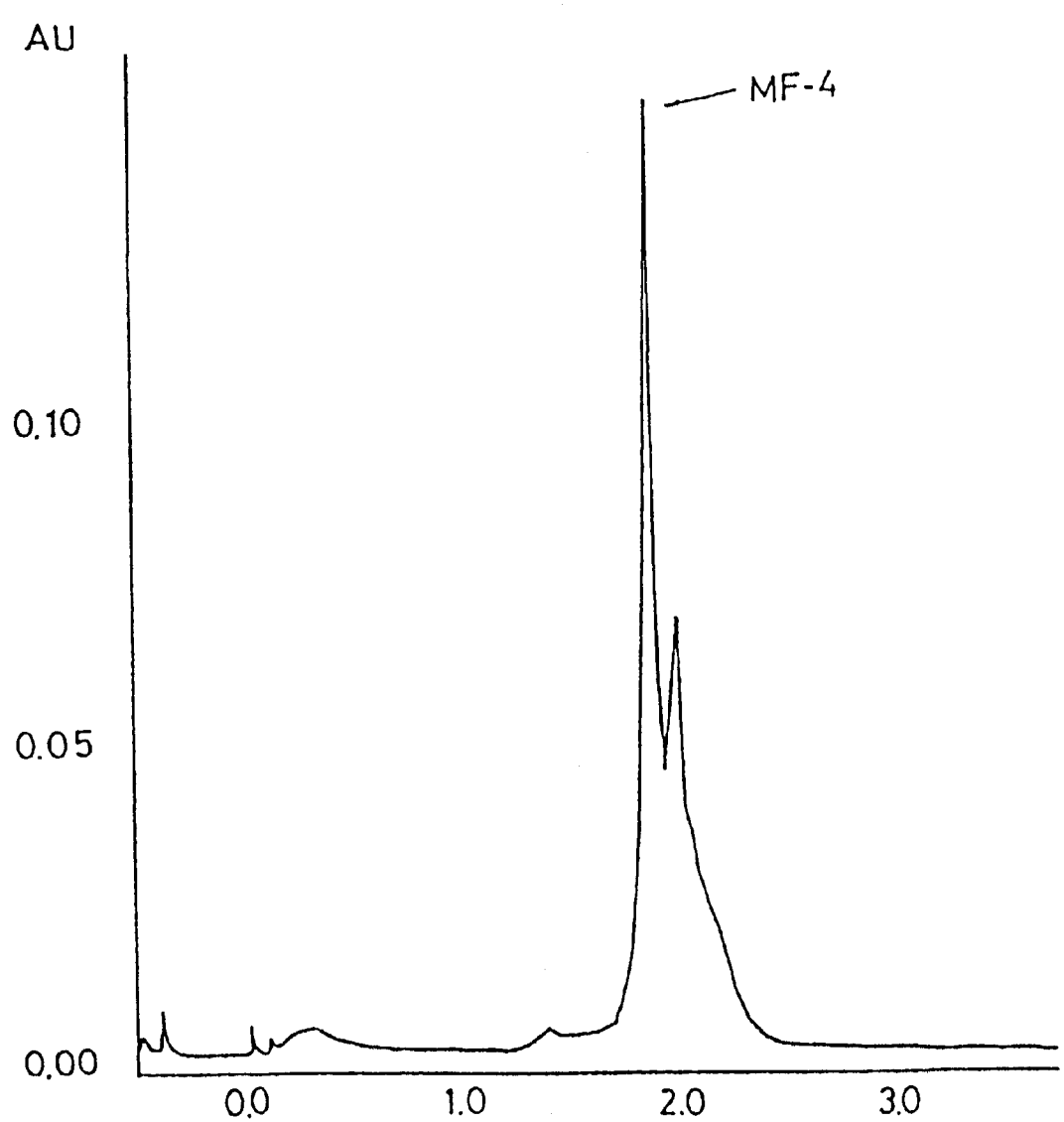
FIG. 8 is a chart showing an MF-4 peak by Mono Q chromatography.
Figure 24:
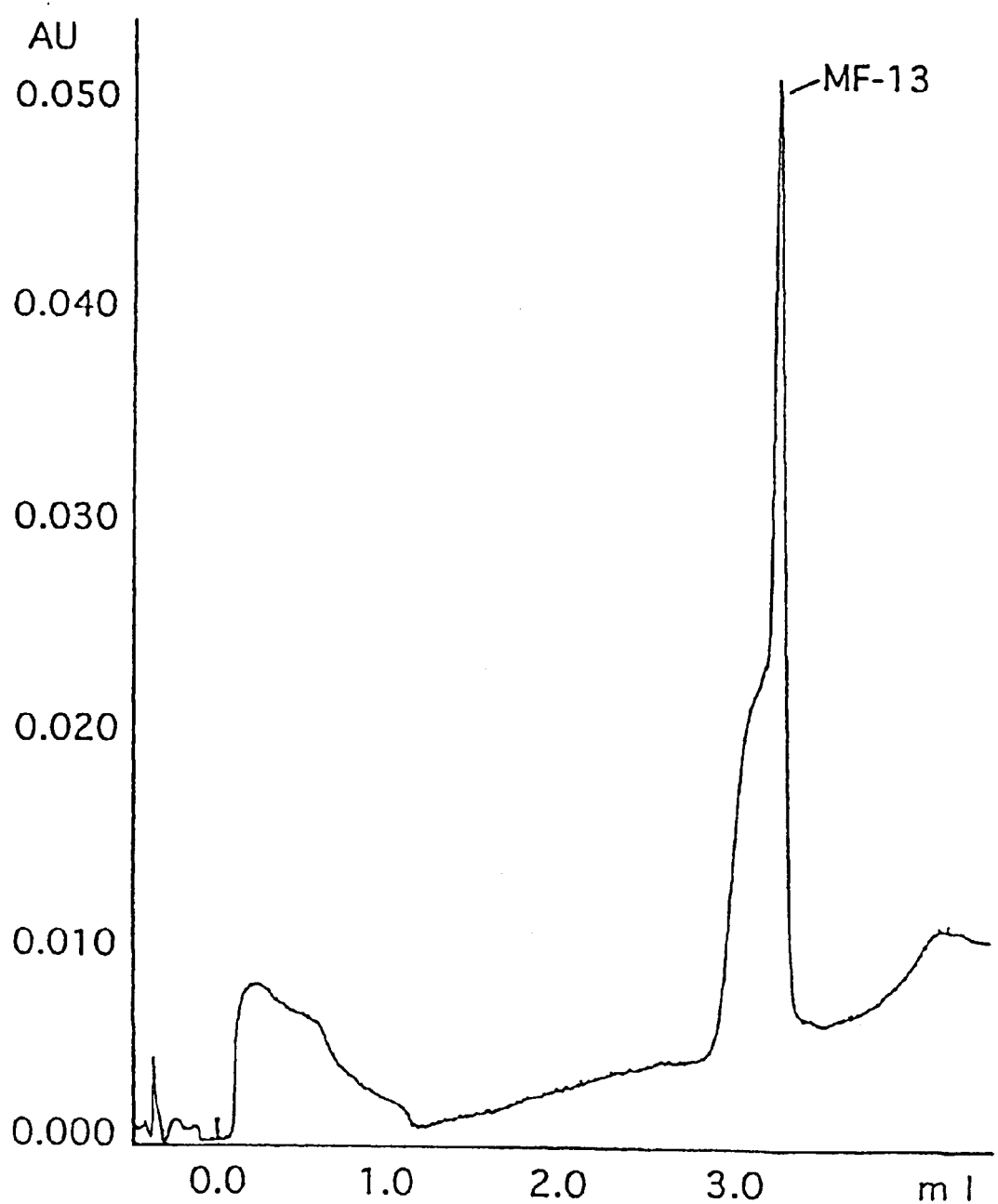
FIG. 24 is a chart showing MF-13 peak obtained by Phenyl Superrose chromatography.

The purification method used is described in detail. Peaks 1 through 4 as separated from Mono Q were each diluted 2 folds with a 0.1 M potassium phosphate buffer (pH 7.0) containing 4 M ammonium sulfate, and thereafter, the dilution was applied to a column of Phenyl Superose PC 1.6/5 (column volume: 0.1 ml, manufactured by Pharmacia), previously equilibrated with a 0.1 M potassium phosphate buffer (pH 7.0) containing 2 M ammonium sulfate, and the elution was carried out with the same 0.1 M buffer on a linear gradient from 2 M to 0 M ammonium sulfate. The antigenic protein-containing fraction obtained was concentrated using an ultrafiltration membrane (MW 10,000), and the resulting concentrate was then subjected to gel filtration chromatography using the Sephadex G-75 Superfine column (1.5×100 cm) to obtain a fraction eluted at a molecular weight of about 40,000. The gel filtration product obtained was further subjected to ion exchange chromatography using a column of Mono Q PC 1.6/5, and elution was carried out in the same manner as above to isolate antigenic proteins. In other words, MF-1 was isolated from Peak 2 (FIG. 5); MF-2 was isolated from Peak 1 (FIG. 6); MF-3 was isolated from Peak 3 (FIG. 7); and MF-4 was isolated from Peak 4 (FIG. 8). Separately, the Mono Q non-adsorbed fraction was applied to the same column of Phenyl Superose PC 1.6/5 (column volume: 0.1 ml, manufactured by Pharmacia), and the elution was carried out with the same 0.1 M buffer on a linear gradient from 2 M to 0 M ammonium sulfate (FIG. 24) to isolate a pure, antigenic protein named MF-13.

1-4) Identification of MF-1 Through MF-4 by Two-Dimensional Electrophoresis and Isolation of Purified, Antigenic Proteins MF-5 Through MF-12

Figure 9:
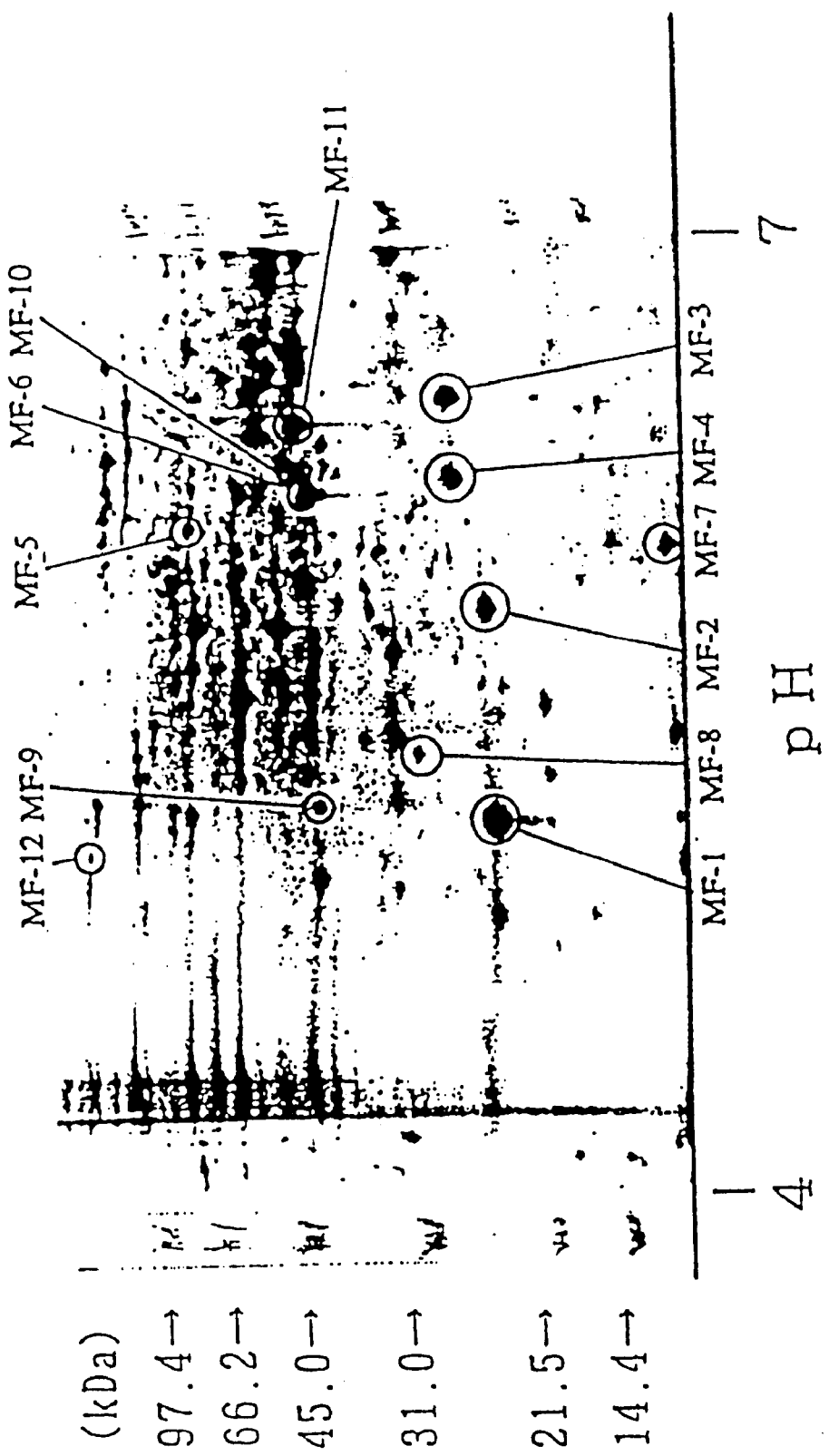
FIG. 9 is a two-dimensional electrophoretic analysis of a crude antigen 2782 of Malassezia. Here, the protein is detected by staining with Coomassie brilliant blue.
Figure 10:
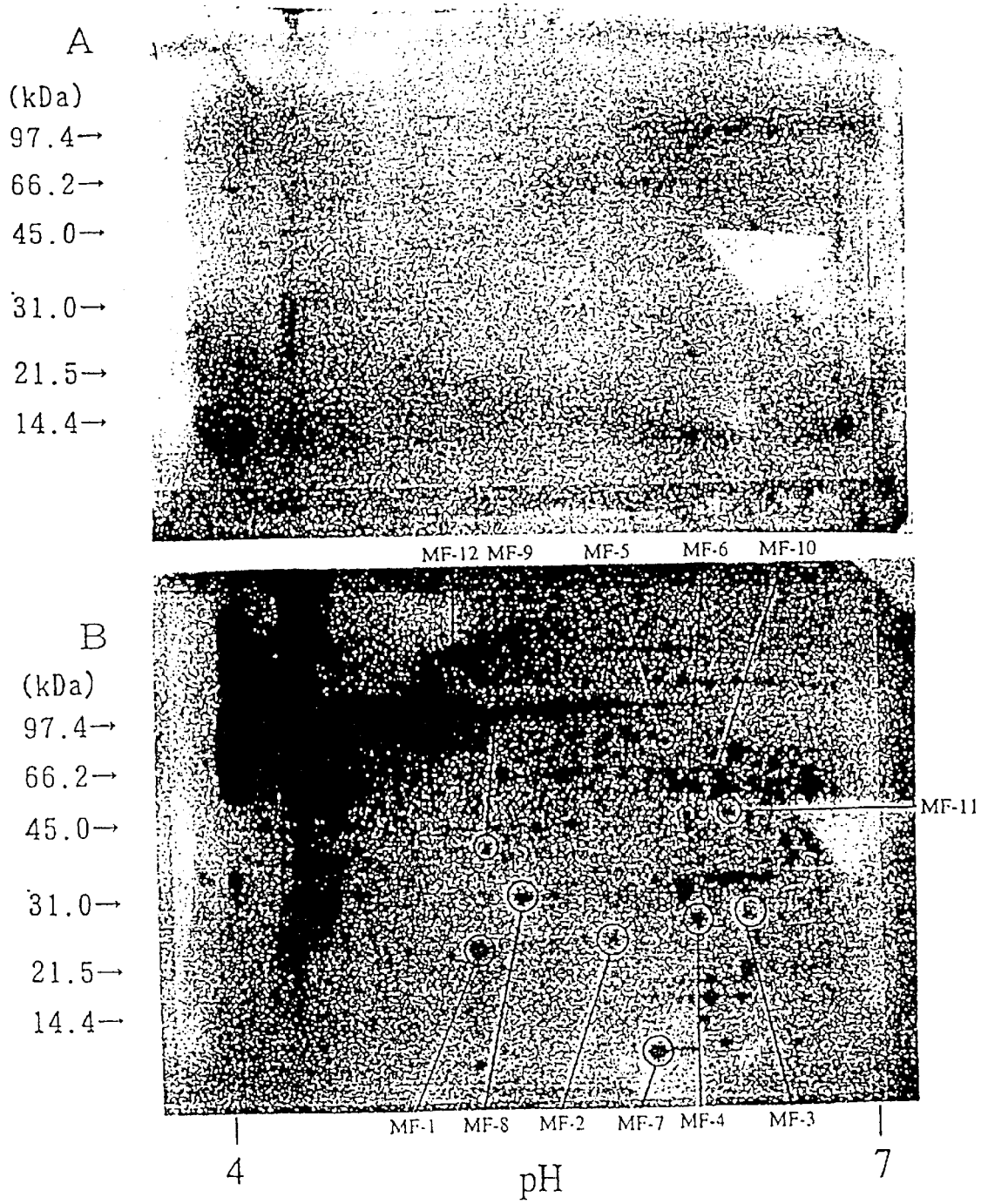
FIG. 10 is a two-dimensional electrophoretic analysis of crude antigen 2782 of Malassezia. Here, spots are detected by immunoblotting method using an IgE antibody (A) of a normal individual and an IgE antibody (B) of an allergic patient.

Further, 150 μg of the above-described Malassezia partially purified crude antigen 2782 was dissolved in a solution containing 8 M urea, 0.5% NP-40, 2% β-mercaptoethanol, 0.8% Pharmalyte (manufactured by Pharmacia), and 0.01% Bromophenol Blue. First-dimensional isoelectric electrophoresis was carried out by a conventional method using the Immobiline DryStrip gel (pH 4–7, manufactured by Pharmacia). Second-dimensional SDS-PAGE was carried out using the ExelGel SDS-Homogeneous (12.5%, manufactured by Pharmacia), followed by protein detection by CBB staining (FIG. 9). After protein transfer onto a PVDF membrane (manufactured by Millipore), immunoblotting was carried out using sera from patients with allergoses (IgE antibodies) with a positive response to the crude antigen in skin test and a high value in RAST method, and normal individual sera (IgE antibodies) to detect positive spots (FIG. 10). Of the positive spots found, those judged to have high positive rate, namely, one having a molecular weight of about 21 kDa and an isoelectric point of about 5.3; one having a molecular weight of about 20 kDa and an isoelectric point of about 5.8; one having a molecular weight of about 27 kDa and an isoelectric point of about 6.5; and one having a molecular weight of about 26 kDa and an isoelectric point of about 6.3 were identified as MF-1, MF-2, MF-3, and MF-4, respectively, based on the results of N-terminal sequencing, and the like. Also detected were proteins having a molecular weight of about 66 kDa and an isoelectric point of about 6.1 (named MF-5); a molecular weight of about 43 kDa and an isoelectric point of about 6.2 (named MF-6); a molecular weight of about 15 kDa and an isoelectric point of about 6.0 (named MF-7); a molecular weight of about 30 kDa and an isoelectric point of about 5.4 (named MF-8); a molecular weight of about 40 kDa and an isoelectric point of about 5.3 (named MF-9); a molecular weight of about 44 kDa and an isoelectric point of about 6.2 (named MF-10); a molecular weight of about 45 kDa and an isoelectric point of about 6.4 (named MF-11); and a molecular weight of about 100 kDa and an isoelectric point of about 5.0 (named MF-12) as proteins binding to the IgE antibodies of the patients with allergoses. These proteins were extracted from the gel and isolated.

1-5) Physicochemical Properties of Purified, Antigenic Proteins MF-1, MF-2, MF-3, MF-4, MF-5, MF-6, MF-7, MF-8, MF-9, MF-10, MF-11, MF-12, and MF-13

Figure 11:
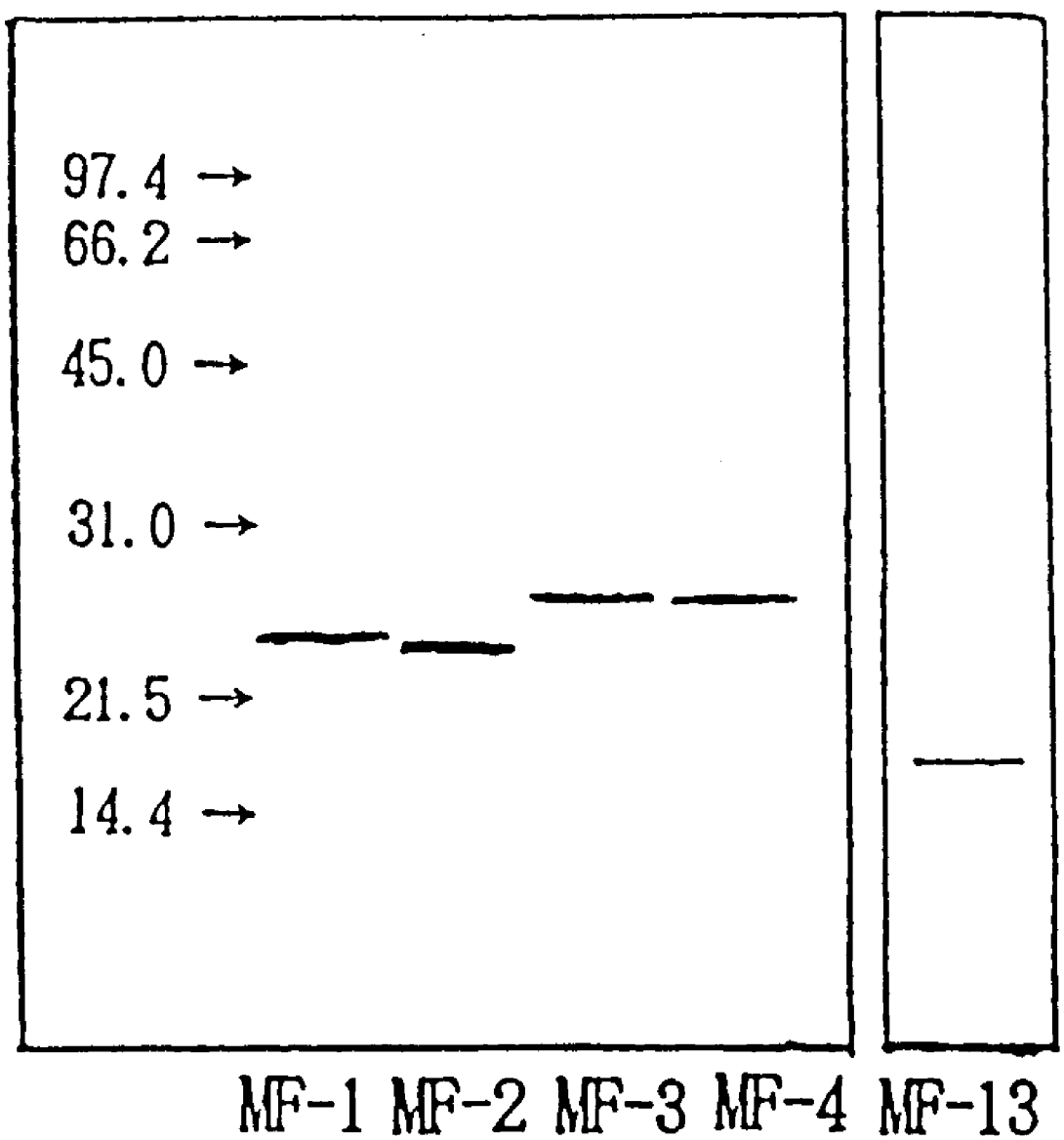
FIG. 11 is an electrophoretic analysis using SDS-PAGE (under reduced conditions) of MF-1, MF-2, MF-3, MF-4, and MF-13.

The isolated MF-1, MF-2, MF-3, MF-4, and MF-13 each showed a single band in SDS-PAGE (FIG. 11). The results of analysis by SDS-PAGE and isoelectric electrophoresis of MF-1 through MF-13 are shown in Table 1. Isoelectric electrophoresis of MF-1 through MF-4 in non-denatured form was carried out by a conventional method using IsoGel Plate at pH 3–10 (manufactured by FMC). The results of analysis of SDS-PAGE and isoelectric electrophoresis of MF-5 through MF-12 were calculated from the results of two-dimensional electrophoresis shown in FIG. 9.

TABLE 1

| | SDS-PAGE (kDa) | | |
|---|---|---|---|
| | Under Reduced Conditions[1] | Under Non-Reduced Conditions | Isoelectric Point[2] |
| MF-1 | 21 | 40 | 4.7 (5.3) |
| MF-2 | 20 | 40 | 4.8 (5.8) |
| MF-3 | 27 | 27 | 5.2 (6.5) |
| MF-4 | 26 | 26 | 5.2 (6.3) |
| MF-5 | 66 | — | — (6.1) |
| MF-6 | 43 | — | — (6.2) |
| MF-7 | 15 | — | — (6.0) |
| MF-8 | 30 | — | — (5.4) |
| MF-9 | 40 | — | — (5.3) |

TABLE 1-continued

|  | SDS-PAGE (kDa) | | Isoelectric Point[2] |
|---|---|---|---|
|  | Under Reduced Conditions[1] | Under Non-Reduced Conditions | |
| MF-10 | 44 | — | — (6.2) |
| MF-11 | 45 | — | — (6.4) |
| MF-12 | 100 | — | — (5.0) |
| MF-13 | 16 | — | 8.1 |

[1] Reduction: Treated with 3% of mercaptoethanol.
[2] Numbers inside brackets each indicate an isoelectric point in a denatured state with 8M urea.

1-6) Preparation of Purified Antigenic Proteins MF-1, MF-2, MF-3, MF-4, and MF-13 in Large Amounts A solution of the above-described Malassezia partially purified crude antigen 2782 in a 0.05 M Tris-HCl buffer (pH 8.0) was adsorbed to a column of DEAE-cellulose, previously equilibrated with the same buffer. The column was washed with the same buffer followed by step-by-step elution with the same buffer containing 0.1 M, 0.2 M, and 0.5 M sodium chloride. The fraction eluted with the buffer containing 0.1 M sodium chloride was concentrated using an ultrafiltration membrane (MW 10,000), and the concentrate was then subjected to column chromatography using a column of Sephacryl S-200HR (1.5×90 cm). The eluted fractions having apparent molecular weights of 30,000 to 50,000 were collected and concentrated using an ultrafiltration membrane (MW 10,000), and the concentrates were then subjected to chromatography using the Sephadex G-75 Superfine column (1.5×100 cm) to give Fraction 2 eluted at a molecular weight of about 40,000. This F2 fraction was dialyzed against a 0.05 M Tris-HCl buffer (pH 8.0) containing 0.5 M sodium chloride, and the dialyzed fraction was then subjected to chromatography using the Chelating Sepharose Fast column (1×15 cm), previously chelated with zinc ions and equilibrated with the same buffer. The column was washed with the same buffer followed by elution at buffers pH decreasing levels of 7.0, 6.0, 5.0, and 4.0. The fraction eluted with the pH 5.0 buffer was collected and concentrated, and the concentrate was then further purified by chromatography using the Sephadex G-75 Superfine column (1.5×100 cm), to thereby isolate MF-2.

The effluent fraction in the zinc chelate chromatography was subsequently purified by copper chelate chromatography. Specifically, the effluent fraction was subjected to chromatography using the Chelating Sepharose Fast column (1×15 cm), previously chelated with copper ions and equilibrated with a 0.05 M Tris-HCl buffer (pH 8.0) containing 0.5 M sodium chloride. The column was washed with the same buffer, followed by elution at buffers of decreasing pH levels of 7.0, 6.0, 5.0, and 4.0. The fraction eluted at pH 4.0 was concentrated using an ultrafiltration membrane (MW 10,000), and the concentrate was then further purified by chromatography using the above-mentioned Sephadex G-75 Superfine column, to give MF-1 fraction eluted at a molecular weight of about 40,000. The resulting effluent fraction was concentrated using an ultrafiltration membrane (MW 10,000), and the concentrate was then purified by chromatography using the above-mentioned Sephadex G-75 Superfine column, to give a fraction eluted at a molecular weight of about 40,000. Thereafter, the eluted fraction was purified by anion exchange column chromatography of Mono Q., to isolate MF-3 and MF-4.

A portion of the above-described Malassezia partially purified antigen 2782 fraction non-adsorbed to a DEAE-cellulose column was applied to a column of HiLoad 16/60 Superdex 75pg (manufactured by Pharmacia), previously equilibrated with 0.05 M NH$_4$HCO$_3$, to collect a fraction having a molecular weight of not more than 20,000. The resulting fraction was adsorbed to HiTrap SP, previously equilibrated with a 0.05 M acetate buffer (pH 5), and elution was carried out with the same buffer supplemented with 0.2 M NaCl. The eluted fraction was applied to a column of HiLoad 16/60 Superdex 75 pg, previously equilibrated with 0.05 M NH$_4$HCO$_3$, to isolate MF-13.

Finally, using about 0.5 g each of the Malassezia partially purified crude antigen 2782 as a starting material, MF-1, MF-2, MF-3, MF-4, and MF-13 were obtained in amounts of 10 mg, 2 mg, 3 mg, 2 mg, and 2 mg, respectively. These antigenic proteins thus prepared in such large amounts gave similar results as those described under Item 1-4) above and Example 10, in terms of SDS electrophoresis, isoelectric electrophoresis, and N-terminal amino acid sequencing analysis.

EXAMPLE 2

Preparation of Monoclonal Antibodies 2-1) Mouse Immunization, Cell Fusion, and Hybridoma Cloning Ten micrograms of each of the purified antigenic proteins MF-1, MF-2, and MF-3 as obtained in Example 1 was suspended in a Freund's complete adjuvant, and each suspension was intraperitoneally administered to male BALB/c mice at 5 weeks of age. Four weeks later, 20 μg of an allergen suspended in a Freund's complete adjuvant was intraperitoneally administered for booster. Additional four weeks later, 20 μg of the same allergen dissolved in a physiological saline was intravenously administered.

Three days after final immunization, cell fusion was carried out by taking out splenocytes and mixing with myeloma cells (P3X63-Ag8.653) in a 4:1 ratio, and then adding 43% polyethylene glycol 2000 thereto. This mixture was sown into 96-well microplate wells at 2×10$^5$ splenocytes/well, and hybridomas were proliferated in an HAT medium selectively. The presence of the desired antibody produced was examined by ELISA using the culture supernatant to select antibody-producing cells. As a result, the 5B4 strain (FERM BP-5608) was obtained as a clone of a hybridoma that produces the M-40 monoclonal antibody against the purified antigenic protein MF-1; the 8G11 strain (FERM BP-5609) was obtained as a clone of a hybridoma that produces the M-3 monoclonal antibody against the purified antigenic protein MF-2; and the 10C1 strain (FERM BP-5610) was obtained as a clone of a hybridoma that produces the M-1 monoclonal antibody against the purified antigenic protein MF-3.

2-2) Preparation of Ascites and Purification of Monoclonal Antibodies

To pristane-pretreated nude mice, 10$^7$ hybridomas were intraperitoneally injected to allow hybridoma proliferation, and after one to two weeks, ascites was collected. From the resulting ascites, the monoclonal antibodies were purified using a protein A column kit (manufactured by Amersham), to give the M-40 monoclonal antibody against MF-1, the M-3 monoclonal antibody against MF-2, and the M-1 monoclonal antibody against MF-3. These monoclonal antibodies were all of the IgG1 isotype.

2-3) Preparation of Monoclonal Antibody-Immobilized Column and Purification of Antigenic Protein MF-3 Using Above Column Fifteen milligrams of the above M-1 monoclonal antibody was dialyzed against a coupling buffer (0.1 M NaHCO$_3$, 0.5 M NaCl, pH 8.3), and the dialyzed monoclonal antibody was then coupled to 1 g of Sepharose 4B (manufactured by Pharmacia) activated with cyanogen bromide by a conventional method to prepare an antibody-immobilized resin.

The resin obtained was transferred into a lesser column of 5 ml capacity. A solution of 40 mg of the Malassezia partially purified crude antigen 2782 in a 0.05 M Tris-HCl buffer (pH 8.0) was applied to the column. After the column was thoroughly washed with a 0.1 M Tris-HCl buffer (pH 8.0), elution of the antibody-bound antigenic protein was carried out with a 0.1 M glycine-HCl buffer (pH 2.5). The eluate was immediately made neutral again by the addition of a 1 M Tris-HCl buffer (pH 8.0), and the neutralized eluate was then concentrated using an ultrafiltration membrane (MW 10,000), followed by gel filtration chromatography using the Sephadex G-75 Superfine column (1.5×100 cm) in the same manner as above, to isolate about 300 µg of MF-3 of high purity.

EXAMPLE 3

Diagnostic Application of Purified Antigenic Proteins 3-1) Determination of Specific IgE Antibodies by RAST Method Paper disc activation with cyanogen bromide and coupling of purified allergens to the paper disc were carried out according to the method of Miyamoto et al. (*Allergy*, 22, 584–594, 1973). One paper disc coupled with the allergen and 50 µl of sera from patients were added to a polystyrene tube, followed by incubation at room temperature for 3 hours. The paper disc was washed three times with a physiological saline containing 0.2% Tween 20, and 50 µl of the $^{125}$I-labeled anti-human IgE antibody of the RAST-RIA kit, manufactured by Pharmacia, was then added, followed by overnight incubation at room temperature. The disc was washed three times again, and radioactivity was then determined using a gamma counter. From a standard curve prepared from a simultaneous radioactivity determination with a reference reagent of the kit, the IgE antibody titer was calculated. For samples that yielded values exceeding the upper limit of the standard curve (>17.5 PRU/ml), the antibody titer was calculated after the samples were diluted 10 folds or 100 folds in equine sera and assayed again.

3-2) Diagnosis Using Purified, Antigenic Proteins MF-1, MF-2, MF-4, and MF-13

A skin test using a Malassezia crude antigen was carried out on patients with atopic dermatitis (hereinafter abbreviated AD) or bronchial asthma (hereinafter abbreviated BA) or both (AD+BA). Positive response was observed in 43 out of 57 AD patients (75%), 108 out of 919 of BA patients (12%), and 47 out of 102 AD+BA patients, demonstrating an extremely high positivity rate in the AD patients. Also, 100%, 59%, and 85%, respectively among these AD, BA, and AD+BA patients with positive skin tests, were positive in IgE antibody determination by RAST method.

On the 76 patients (AD patients: 30, BA patients: 20, AD+BA patients: 26) positive both in the skin test using the Malassezia crude antigen and in RAST method (1 or higher score), IgE antibody titers against three purified antigenic proteins, i.e., MF-1, MF-2, and MF-4, were determined by RAST method (RIA method). IgE antibody titers for antigenic proteins were determined on 12 normal individuals with negative skin tests as well in the same manner as above. As a result, it was made clear from Table 2 that IgE antibodies against the antigenic proteins were present in sera from patients at very high rates. Especially high positivity rates were obtained against MF-1 and MF-2. Further, there were patients with surprisingly very high IgE antibody titers (Table 3), and particularly the mean titer against MF-1 and MF-2 for the AD patients was 100 PRU, and there were some patients with highest values exceeding 1,000 PRU. Also, the sera from all patients positive to the Malassezia crude antigen in RAST method contained the IgE antibody against any one of the purified antigenic proteins MF-1, MF-2, and MF-4.

Also the IgE antibody titer against MF-13 by RAST method for 11 AD patients positive both in the skin test using the Malassezia crude antigen and in RAST method. As a result, nine out of 11 patients were found to be positive in RAST.

TABLE 2

Patients with Allergoses (Rate of RAST Positive)

| | BA (n = 20) | AD + BA (n=26) | AD (n = 30) | Total (n = 76) | normal individuals (n = 12) |
|---|---|---|---|---|---|
| MF-1 | 100 (20/20) | 96 (25/26) | 90 (27/30) | 95 (72/76) | 0 (0/12) |
| MF-2 | 100 (20/20) | 100 (26/26) | 87 (26/30) | 95 (72/76) | 0 (0/12) |
| MF-4 | 75 (15/20) | 88 (23/26) | 87 (26/30) | 84 (64/76) | 0 (0/12) |

BA: Patients with allergic asthmatics.
AD: Patients with atopic dermatitis.
AD + BA: Patients with Atopic dermatitis and allergic asthmatics complications.

TABLE 3

Patients with Allergoses [IgE Antibody Titer (PRU Value)]

| | BA(n = 20) | AD + BA (n = 26) | AD(n = 30) | normal Individuals (n = 12) |
|---|---|---|---|---|
| MF-1 | 1.65 ± 0.66 | 14.73 ± 4.15 | 119.73 ± 56.95 | <0.35 |
| MF-2 | 4.32 ± 2.59 | 16.01 ± 4.45 | 112.84 ± 52.23 | <0.35 |
| MF-4 | 3.54 ± 2.08 | 9.75 ± 2.43 | 94.75 ± 42.43 | <0.35 |

BA: Patients with allergic asthmatics.
AD: Patients with atopic dermatitis.
AD + BA: Patients with Atopic dermatitis and allergic asthmatics complications.

3-3) Immunological Properties of Purified Antigenic Proteins MF-1, MF-2, MF-3, and MF-4

A RAST cross inhibition test using pooled sera from patients was carried out to evaluate cross reactivity among three purified antigenic proteins (MF-1, MF-2, MF-4) (Table 4). As a result, it was shown that they did not mutually cause cross-reactivity, namely that the specific IgE antibodies against the respective purified antigenic proteins are present in the sera from patients.

TABLE 4

| Antigen Immobilized on Solid Phase | Concentration of Various Antigens Required for 50% Inhibition of Binding Antigen Immobilized on Solid Phase and Patient IgE (µg/ml) | | |
|---|---|---|---|
| | MF-1 | MF-2 | MF-4 |
| MF-1 | 0.038 (1) | 8.6 (230) | 52 (1370) |
| MF-2 | >100(>7700) | 0.013 (1) | >100(>7700) |
| MF-4 | 18 (290) | 30 (480) | 0.062 (1) |

Figure 12:
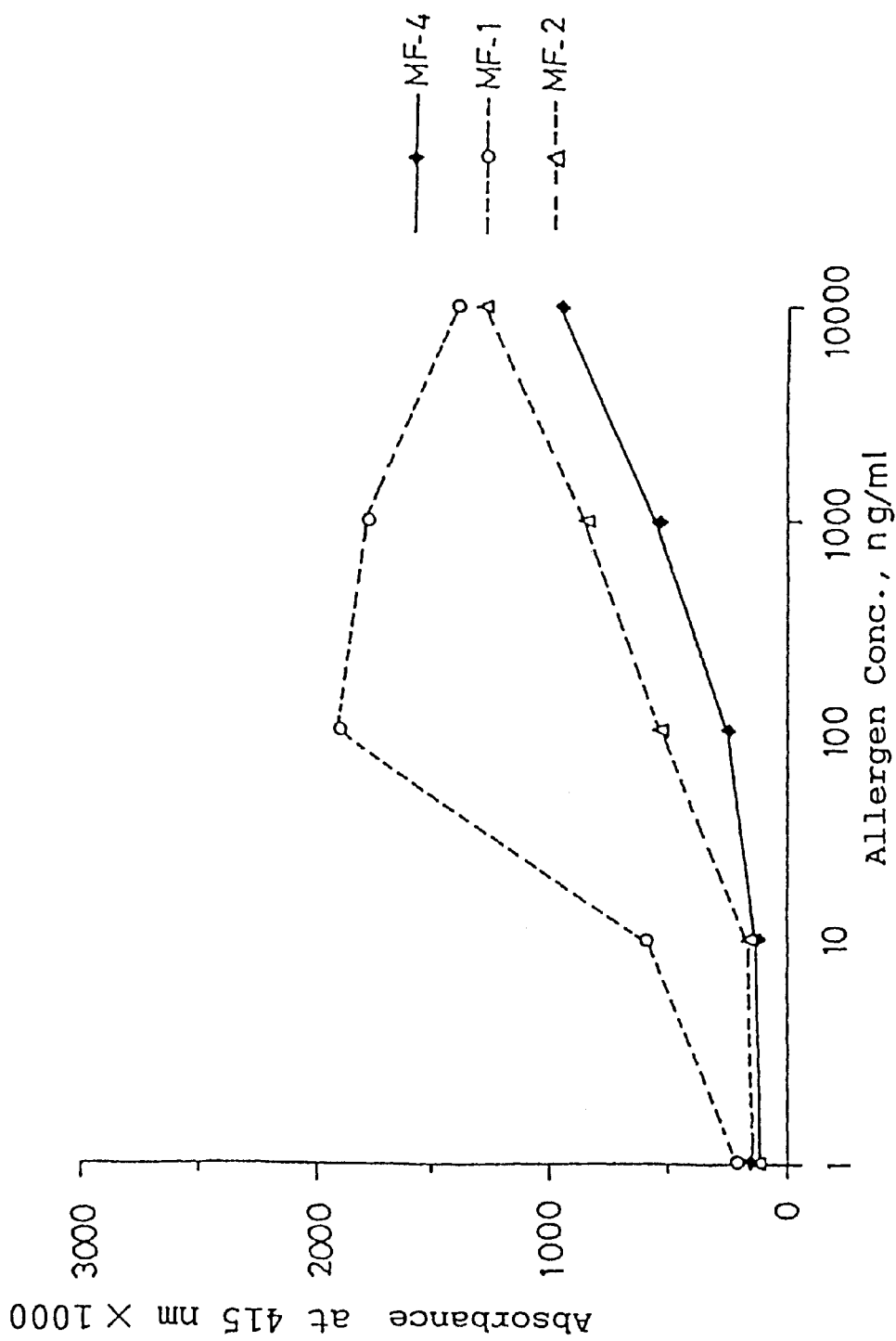
FIG. 12 is a graph showing the concentration dependency of the IgE binding ability of antigenic proteins MF-1, MF-2, and MF-4.

Next, the purified antigenic proteins MF-1, MF-2, and MF-4 were stepwise diluted and their antigen potencies were determined by the Direct RAST EIA method. Specifically, dilutions of the purified, antigenic protein MF-1, MF-2, and MF-4 were each coupled to a cyanogen bromide-activated paper disc and then the coupled purified, antigenic protein was blocked with ethanolamine. Thereafter, 50 µl of a 5-fold dilution of pooled sera was then added to each disc, and the mixture was reacted with a diluted µ-galactosidase-labeled goat anti-human IgE antiserum. Thereafter, an enzyme substrate was added, followed by absorption determination at 415 nm. The results are shown in FIG. 12. It is clear that MF-1 binds to sera from patients IgE at the lowest concentration.

Figure 13:
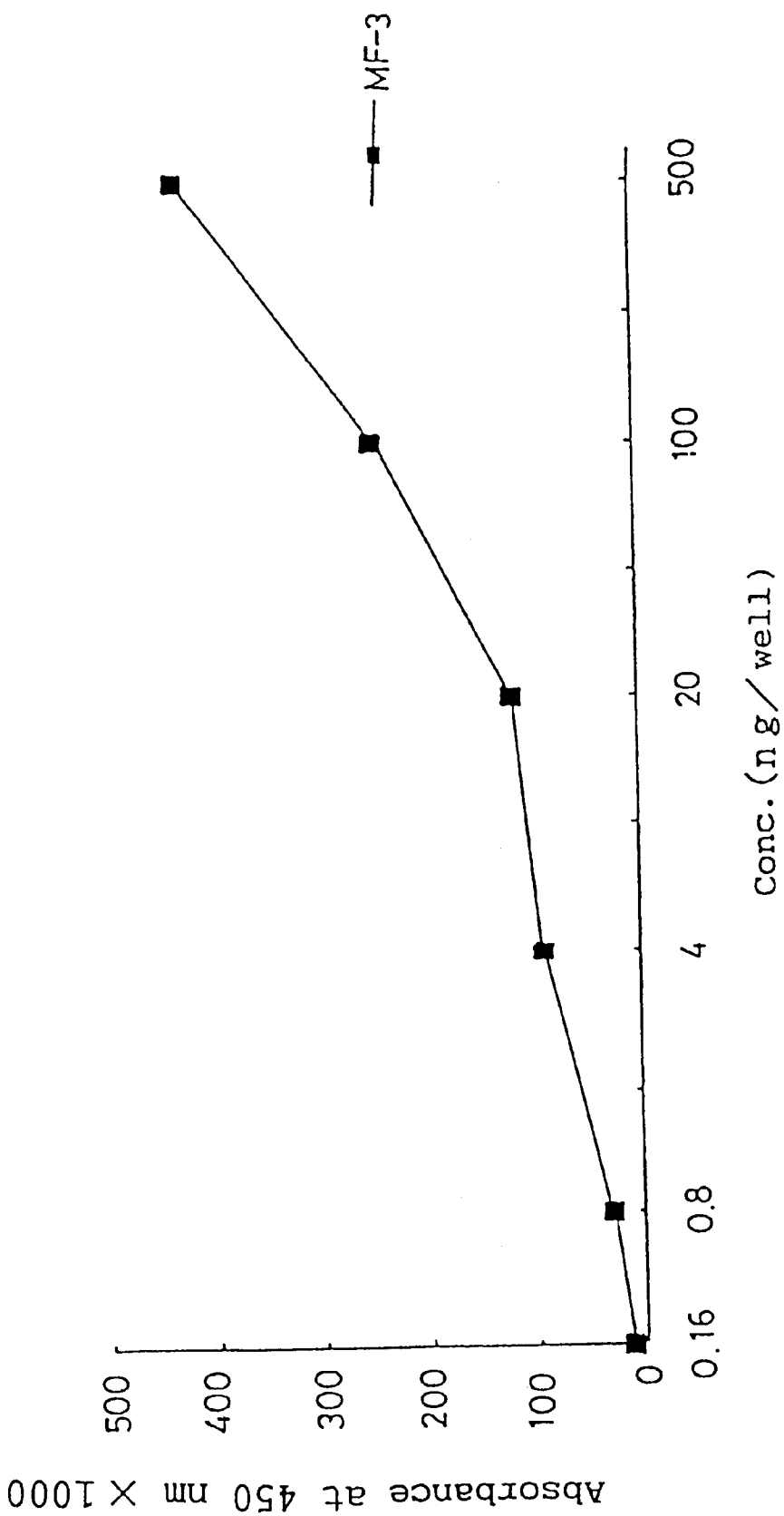
FIG. 13 is a graph showing the concentration dependency of the IgE binding ability of MF-3.

Separately, the purified antigenic protein MF-3 was stepwise diluted, and its antigen potency was determined by ELISA. Specifically, after applying each dilution of the purified antigenic protein MF-3 to a microplate, the microplate was washed with a physiological saline containing 0.01% Tween 20, blocked with PBS containing 3% BSA, washed with a physiological saline containing 0.01% Tween 20, and then pooled sera were added. The microplate was kept standing at 37° C. for 2 hours, and a secondary antibody, a peroxidase-labeled goat anti-human IgE antiserum was added, and subsequently a substrate solution was added; after color development, absorbance at 450 nm was determined. The results are shown in FIG. 13.

EXAMPLE 4

Preparation of Pyridylethylated Derivative of Cysteine Residue of Purified, Antiqenic Protein MF-2

Figure 14:
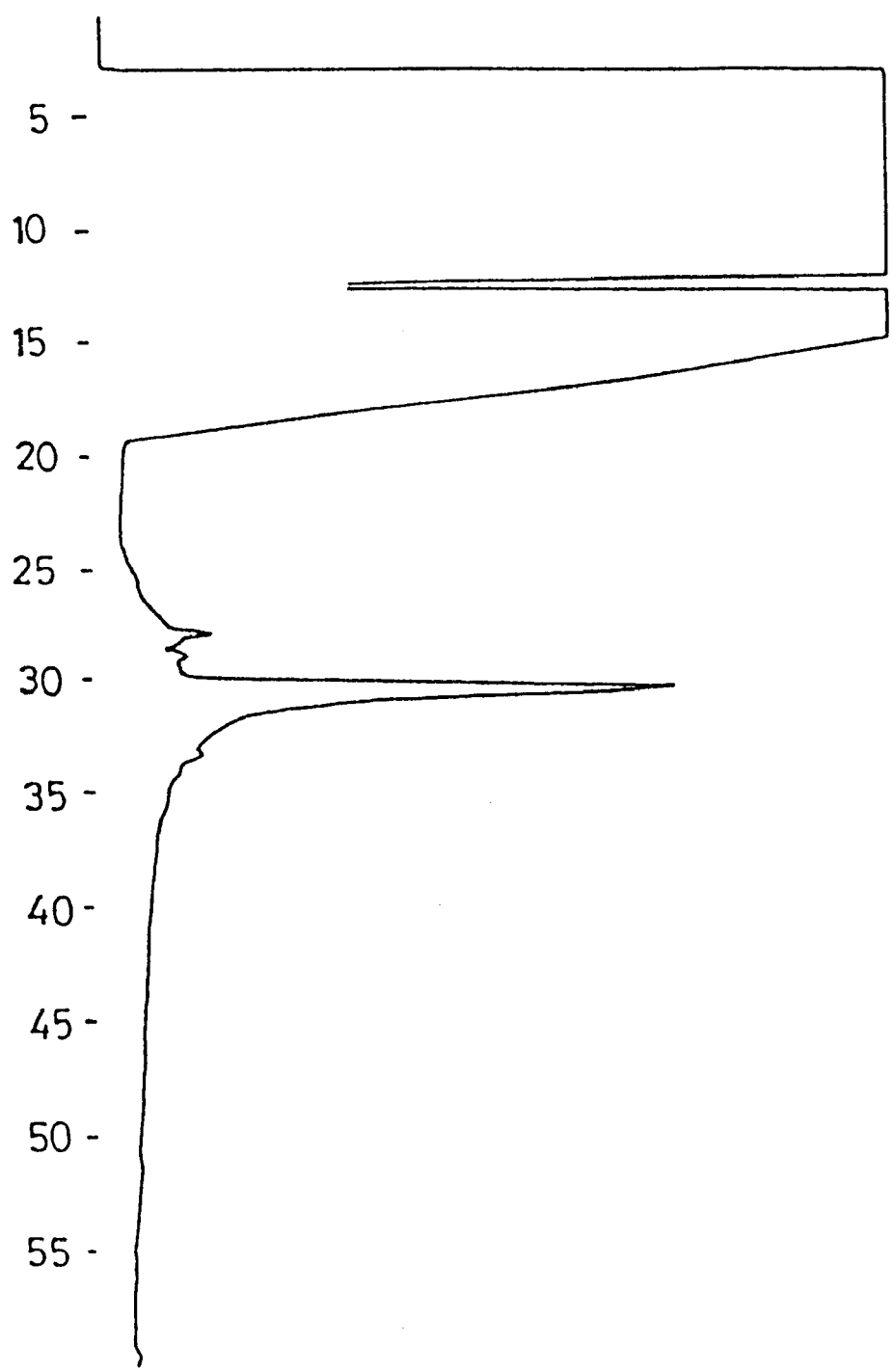
FIG. 14 is a chart showing purification of a pyridylethylated product of MF-3 by HPLC.
Figure 15:
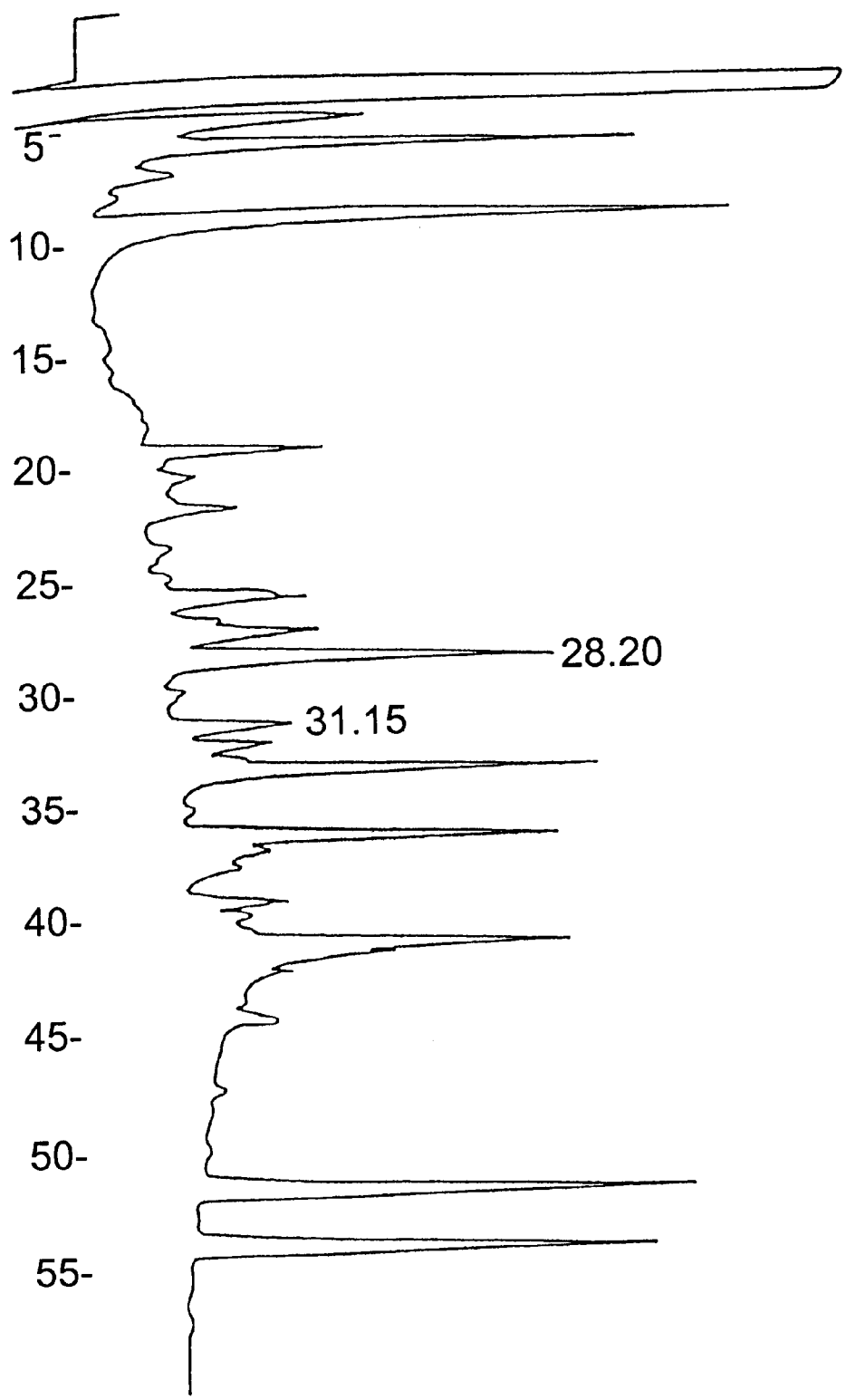
FIG. 15 is an HPLC analytic chart of digested products of lysylendopeptidase of MF-2 (pyridylethylated product).

The purified antigenic protein MF-2 (0.04 mg) was dissolved in 200 µl of a borate-buffered saline (pH 8.0). To this solution were added 800 µl of 5 M guanidine hydrochloride, 1 µl of 4-vinylpyridine, and 2 µl of tributyl phosphine. After replacing the atmosphere with nitrogen gas, reaction was carried out overnight at 37° C., and the resulting mixture was subjected to isolation and purification by HPLC (column: µ-Bondasphere C4-300, 2×150 mm, manufactured by Waters; solvents: washing with 0.05% TFA/water for 15 minutes, followed by linear gradient elution so as to give 80% acetonitrile containing 0.05% TFA after 60 minutes; flow rate: 220 µl/min.; detection: 220 nm; column temp.: 40° C.; FIG. 14). The product obtained was identified as the pyridylethylated product of MF-2, from the fact that its band appeared in the neighborhood of 20 kDa in SDS electrophoresis under non-reduced conditions (in absence of mercaptoethanol), and that the peptide fragments (FIG. 15) which have the N-terminal amino acid sequences as shown by SEQ ID NOs:47 and 48 (eluted at 28.20 and 31.15, respectively), obtained by lysylendopeptidase digestion of the product obtained had a pyridylethylcysteine group. The pyridylethylated MF-2 obtained, which was similar to MF-2, was confirmed to be bound to sera IgE of patients from Malassezia allergoses by immunoblotting after SDS electrophoresis.

EXAMPLE 5

Isolation of Antiqenic Fragment Peptide Derived from Purified Antigenic Protein MF-3

Figure 16:
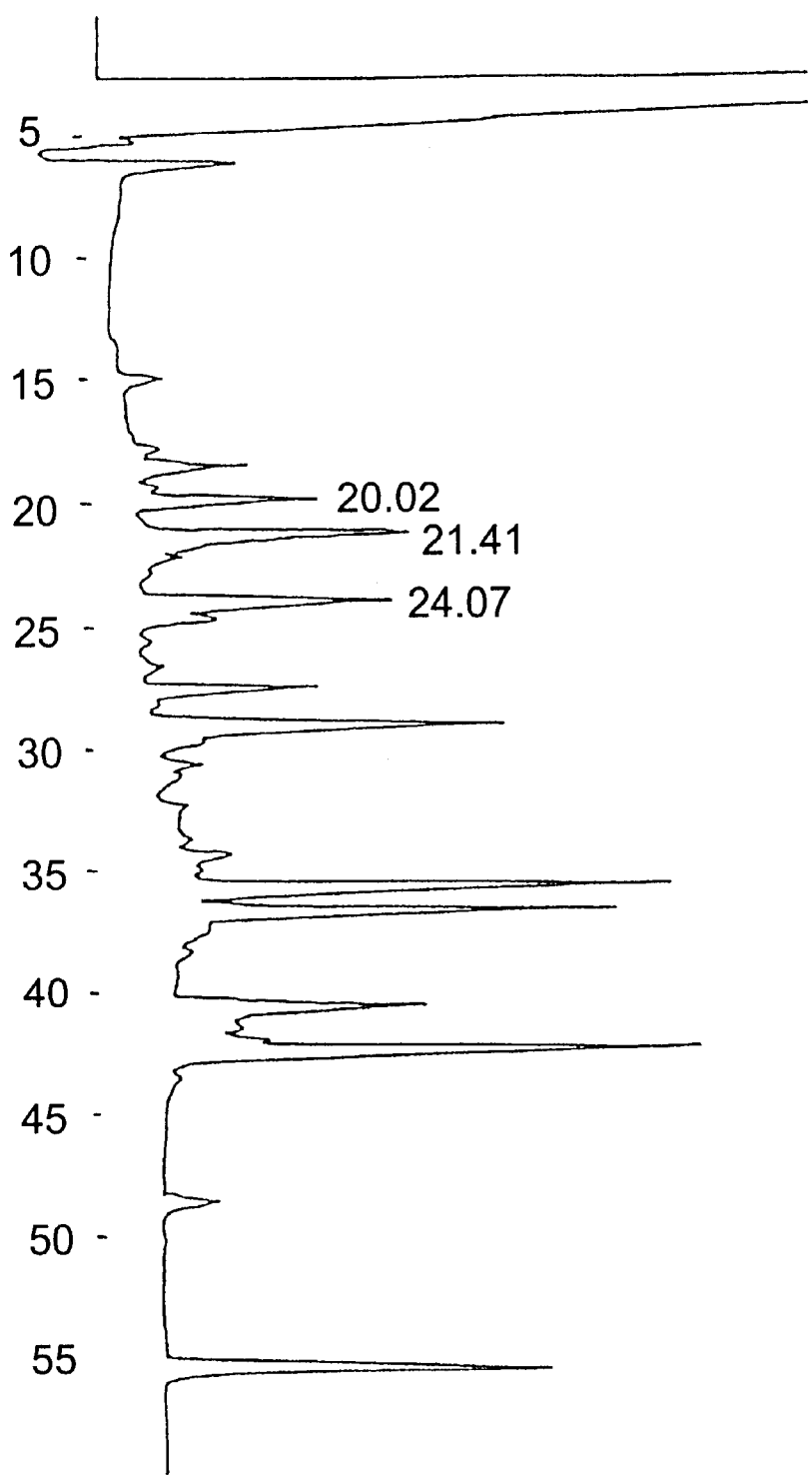
FIG. 16 is an HPLC analytic chart of digested products of lysylendopeptidase of MF-3 (pyridylethylated product).

The purified antigenic protein MF-3 (0.04 mg) was dissolved in 100 µl of a borate-buffered saline (pH 8.0). To this solution were added 900 µl of 5 M guanidine hydrochloride, 1 µl of 4-vinylpyridine, and 2 µl of tributyl phosphine. After replacing the atmosphere with nitrogen gas, reaction was carried out overnight at 37° C., and the resulting mixture was subjected to isolation and purification by HPLC (column: µ-Bondasphere C4-300, 2×150 mm, manufactured by Waters; solvents: washing with 0.05% TFA/water for 15 minutes, followed by linear gradient elution so as to give 80% acetonitrile containing 0.05% TFA after 60 minutes). To the resulting purified, antigenic protein MF-3 treated with guanidine hydrochloride were added, 100 µl of 50 mM N-ethylmorphine-acetic acid (pH 9.0) and lysylendopeptidase (Achromobacter protease I, manufactured by Wako Pure Chemical Industries), followed by reaction carried out overnight at 37° C. Thereafter, the reaction mixture was subjected to HPLC (column: µ-Bondasphere C18-300, 2×150 mm, manufactured by Waters; solvents: linear gradient elution from 0.05% TFA/water eluted so as to give 60% acetonitrile containing 0.05% TFA; flow rate: 200 µl/min.; detection: 214 nm; column temp.: 40° C.; FIG. 16). Each peptide fragment was separately collected and freeze-dried, and thereafter the freeze-dried fragment was assayed for binding to sera IgE of patients from Malassezia allergoses by ELISA as described below.

Specifically, each peptide fragment (about 10 to 100 pmol for each) was spread onto a microplate using a peptide coating kit (manufactured by Takara Shuzo Co., Ltd.) and then washed with a physiological saline containing 0.01% Tween 20. The washed microplate was blocked with 3% BSA, and treated with the sera from patients. Thereafter, each peptide fragment was then reacted with a diluted peroxidase-labeled goat anti-human IgE antibody, and an enzyme substrate was added thereto. After a given period of time, absorbance was determined to detect antigenic fragments. As a result, there appeared to show the antigenic fragments that were bound to patient serum IgE were present in peaks eluted around 20.02, 21.41, and 24.07 minutes. Of these peaks, the 21.41-minute peak was found to contain a peptide having an amino acid sequence consisting of HHQ-TYVNNLNAAXK (SEQ ID NO:58, wherein X is an undetermined amino acid).

EXAMPLE 6

Lymphocyte Blast Formation Test

Heparinized venous blood samples were collected from subjects [eight patients with allergoses (Nos. 1 through 8 in Table 5), two normal individuals (Nos. 9 and 10 in Table 5)], and lymphocytes were separated by the Ficoll gravitational centrifugation method. After preparation with a 10% FCS-supplemented RPMI1640 medium so as to give a cell number of $5\times10^5$ cells/ml, this suspension was poured onto 96-well microplates at 0.2 ml per plate. The above Malassezia partially purified crude antigen 2782 was added so as to have concentrations of 10 and 100 µg/ml, and the purified, antigenic proteins (MF-1, MF-2, and MF-4) were each added so as to have concentrations of 1 and 10 µg/ml, followed by five days of cultivation in the presence of 5% $CO_2$ at 37° C. under high-humidity conditions. In the forth day, 0.5 µCi tritiated (3H)-thymidine was added. After completion of the cultivation, lymphocytes were harvested and assayed for the amount of $^3H$-thymidine uptake using a liquid scintillation counter. Using the mean value for three runs, the ratio of the amount of the $^3H$-thymidine uptake of the antigen-added and non-added groups was expressed as the SI (stimulation index). The results are shown in Table 5. It is clear from Table 5 that the lymphocytes derived from Patient No. 4 proliferated in response to the purified, antigenic proteins MF-1 and MF-2, and that those derived from Patient Nos. 1 and 6 proliferated especially in response to MF-2.

TABLE 5

SI (in case of adding low allergen concentration/in case of adding high allergen concentration) *

|      | 1       | 2       | 3       | 4       | 5       | 6       | 7       | 8       | 9       | 10      |
|------|---------|---------|---------|---------|---------|---------|---------|---------|---------|---------|
| MF-1 | 7.7/2.5 | 4.3/1.4 | 1.0/0.9 | 4.2/3.7 | 2.6/2.0 | 2.1/1.0 | 1.7/1.2 | 2.1/1.7 | 1.1/0.5 | 2.0/0.7 |
| MF-2 | 4.0/2.9 | 1.3/1.5 | 1.9/1.2 | 7.8/4.2 | 2.3/2.3 | 3.1/2.6 | 2.0/1.8 | 1.4/1.7 | 2.0/0.7 | 1.6/1.0 |
| MF-4 | 1.8/1.3 | 1.2/1.1 | 1.0/0.9 | 2.5/1.4 | 1.2/1.8 | 1.9/1.7 | 1.1/0.9 | 1.3/1.3 | 1.9/0.8 | 0.9/0.6 |

Remarks *:
"In case of adding low allergen concentration" refers to a case of adding 1 µg/ml MF-1, MF-2, or MF-4.
"In case of adding high allergen concentration" refers to a case of adding 10 µg/ml MF-1, MF-2, or MF-4.
1–8: Allergic patients.
9–10: Normal individuals.

EXAMPLE 7

Preparation of Diagnostic Reagent for Intracutaneous Reaction and Preparation of Titration Reagent for Diagnosis Against Malassezia Allergy A purified allergen-active component is dried and collected in a powder form to be used as a diagnostic reagent for intracutaneous reaction against Malassezia allergoses and as a titration reagent for the diagnosis of the Malassezia allergy. The diagnostic reagent for intracutaneous reaction is prepared by 200,000-fold dilution of the allergen-active component using a 0.9% physiological saline containing 0.5% phenol as a solvent. The titration reagent for the diagnosis of the Malassezia allergy is prepared by dissolving the allergen-active component in a Hanks' buffer at a concentration of 1 mg/ml, to give a stock solution for a titration reagent for histamine release, using the dilutions of the stock solution.

EXAMPLE 8

Preparation of Antigenic Agent for Hyposensitization Therapy

A purified allergen-active component is dried and collected in a powder form to be used as a hyposensitization therapeutic agent for Malassezia allergoses. The allergen-active component is dissolved in a 0.9% saline containing 0.5% phenol at a concentration of 1 mg/ml to give a stock solution of an antigen for hyposensitization therapy.

EXAMPLE 9

Quantitative Assay of Purified, Antigenic Protein MF-1 in House Dust and Cultivation of Malassezia House dust was collected from rooms, bedclothes, and the like, in houses inhabited by bronchial asthma patients, using a vacuum cleaner under given conditions. MF-1 was subjected to quantitative assay by means of sandwich ELISA using a rabbit polyclonal antibody and the mouse monoclonal antibody (M-40) as obtained in Example 2-2), and a supernatant obtained from 1:10 (w/v) extraction of the dust was used as a sample for quantitative assay of MF-1. In order to cultivate Malassezia, the dust was suspended in sterile water in a 1:10 (w/v) ratio and sown over a plate medium. Also, a sterile tape was once attached to the bedclothes surface, removed, and placed on the plate medium. The media used were PDA, M40YA, or a Dixon agar medium, and the number of colonies was counted after cultivation at 25° C. for one week.

It is possible to subject MF-1 to quantitative assay of the level of not less than 1 ng/g dust by sandwich ELISA method, by which 87.1 to 1.1 ng/g dust of MF-1 was detected in 16 out of 24 dust samples derived from bedclothes. As for the cultivation results for Malassezia on the bedclothes surface, obtained by the tape method, 10 out of the 24 samples were positive. Incidentally, out of the 24 samples, 14 samples (58%, eight being positive, six being negative) gave results in agreement with those of MF-1 detection by sandwich ELISA method and cultivation.

EXAMPLE 10

Determination of Partial Amino Acid Sequences of Purified, Antigenic Proteins MF-1, MF-2, MF-3, MF-4, MF-5, MF-6, MF-7, MF-10, and MF-13

N-terminal amino acid sequence analysis was carried out by a conventional method. As a result, it was made clear that MF-1 has the amino acid sequence:

Pro Gly Asp Pro Thr Ala Thr Ala Lys Gly Asn Glu Ile   (SEQ ID NO:45)
Pro Asp Thr Leu Met Gly Tyr Ile Pro Trp Thr Pro Glu
Leu Asp

As for MF-2, since its N-terminal is blocked, pyridylethylation was followed by lysylendopeptidase digestion. The resulting peptide fragments were analyzed by C18 reversed-phase HPLC. The various peaks obtained were separately collected, some of which were subjected to amino acid sequencing determination. The three peptide fragments eluted at 27.07 minutes, 28.20 minutes, and 31.15 minutes, respectively, were determined to have the following respective N-terminal amino acid sequences:

```
Val Glu Tyr Phe Gly Ile Asp Glu Gly Glu Pro Lys      (SEQ ID NO:46)

Asp Asn Leu Thr Phe Ala Gln Asp Val Asn Cys Glu Phe  (SEQ ID NO:47)

Val Val Ile Val Ala Val Pro Gly Xaa Phe Thr Pro Thr  (SEQ ID NO:48)

Cys Thr Ala Asn His Val Pro Xaa Tyr Xaa Glu
``` wherein Xaa is an undetermined amino acid.

As for MF-3, since its N-terminal is also blocked, pyridyl-ethylation was followed by lysylendopeptidase digestion. The resulting peptide fragments were analyzed by C18 reversed-phase HPLC. The various peaks obtained were separately collected, some of which were subjected to amino acid sequencing determination. The three peptide fragments eluted at 35.68 minutes, 36.68 minutes, and 29.15 minutes, respectively, were determined to have the following respective N-terminal amino acid sequences:

```
Asp Gln Asp Pro Leu Thr Thr His His Pro Val Ile Gly  (SEQ ID NO:49)

Trp Asp Xaa Xaa Glu His Ala
``` wherein Xaa is an undeterrnined amino acid;

```
Ala Trp Trp Asn Val Val Asn Trp Ala Glu Ala Glu Lys  (SEQ ID NO:50)

Phe Xaa Gly Gly Gly His Ile Asn Xaa Ser Leu Phe      (SEQ ID NO:51)
``` wherein Xaa is an undetermined amino acid.

In addition, as a result of N-terminal amino acid sequence analysis, it was made clear that MF-4 had the amino acid sequence:

```
Lys Tyr Thr Leu Pro Pro Leu Pro Tyr Asp Tyr Gly Ala  (SEQ ID NO:52)

Leu Glu Pro Ala Ile Ser Gly Glu Ile Met Glu Thr His

Tyr Glu Lys His
```

In addition, as a result of N-terminal amino acid sequence analysis, it was made clear that MF-5 had the amino acid sequence:

```
Xaa Xaa Xaa Xaa Xaa Glu Pro Tyr Asp Val Ile Val Ile  (SEQ ID NO:53)

Gly Gly Gly Pro Gly Gly Tyr Val Ala Xaa Xaa Lys Xaa

Xaa Gln
``` wherein Xaa is an undetermined amino acid.

In addition, as a result of N-terminal amino acid sequence analysis, it was made clear that MF-6 had the amino acid sequence:

```
Arg Lys Val Ala Val Leu Gly Ala Ser Gly Gly Ile Gly  (SEQ ID NO:54)

Gln Pro Leu Ser Leu Leu Met Lys Leu Asn Pro Lys Val

Thr Glu Leu Arg
```

In addition, as a result of N-terminal amino acid sequence analysis, it was made clear that MF-7 had the amino acid sequence:

Gly Asn Asn Gly Leu Ser Glu Val Val Tyr Lys Pro Asp (SEQ ID NO:55)
Xaa Gln Xaa Thr Xaa Glu Phe Xaa Val Ile wherein Xaa is an undetermined amino acid.

In addition, as a result of N-terminal amino acid sequence analysis, it was made clear that MF-10 had the amino acid sequence:

Val Asp Gln Xaa Tyr Phe Gly Leu Xaa (SEQ ID NO:56)

wherein Xaa is an undetermined amino acid.

In addition, as a result of N-terminal amino acid sequence analysis, it was made clear that MF-13 had the amino acid sequence:

Ser Asn Val Phe Phe Asp Ile Thr Lys Asn Gly Ser Pro (SEQ ID NO:57)
Leu Gly Thr Ile Lys Phe Lys Leu Phe Asp Asp Val

The other antigenic proteins could not be analyzed due to N-terminal blocking, and the like.

As a result of homology searching with known proteins, it was made clear that MF-2 is a protein having the partial amino acid sequence of SEQ ID NO:48 homologous to a peroxisome membrane protein (PMP-20) derived from *Candida boidinii*, and MF-3 is a protein having the above partial amino acid sequence homologous to iron/manganese-superoxide dismutase. In addition, it was made clear that MF-4 is a protein having the above N-terminal amino acid sequence homologous to iron/manganese-superoxide dismutase in the same manner as in MF-3. In addition, it was made clear that MF-5 is a protein having the above N-terminal amino acid sequence homologous to dehydeolipoamide dehydrogenase. In addition, it was made clear that MF-6 is a protein having the above N-terminal amino acid sequence homologous to malate dehydrogenase. In addition, as for MF-7 and MF-10, no homology to known proteins was found from their N-terminal amino acid sequences. In addition, it was made clear that MF-13 is a protein having the above N-terminal amino acid sequence homologous to cyclophilin.

EXAMPLE 11

Cloning of AntiQenic Protein MF-1 Gene from *M. furfur*

11-a) Purification of Total RNA from *M. furfur*

In order to obtain total RNA from cells of the *M. furfur* TIMM2782 strain, the strain was cultured for 72 hours in 300 ml of a YNB medium (0.67% bacto yeast nitrogen DNA, 0.5% Bacto Casiton, 0.1% Tween 60, 2.0% glucose, 5% MEM-vitamin solution), and the cells were then harvested by centrifugation at 3,000 rpm for 15 minutes. The harvested cells were rapidly frozen with liquid nitrogen. The frozen cells were disrupted into a powder form by a mortar, and 1.3 mg of the total RNA was then recovered and purified by an RNA extraction kit (manufactured by Pharmacia).

11-b) Amplification of MF-1 Gene by RT-PCR

The oligonucleotides MF1F1 and MF1F2, deduced from the amino acid sequence for the N-terminal of the MF-1 protein described in Example 10 were synthesized and purified to be used as primers for PCR. The base sequences for MF1F1 and MF1F2 are shown by SEQ ID NOs:15 and 16, respectively, in Sequence Listing. An MF-1 cDNA was amplified by RT-PCR using RNA PCR Kit Ver. 2 (manufactured by Takara Shuzo Co., Ltd.) with 1 μg of the total RNA purified in Example 11-a). Specifically, the cDNA was synthesized from 1 μg of the total RNA by an AMV reverse transcriptase reaction (at 42° C. for 60 minutes) using an oligo(dT)$_{20}$-M4 adaptor primer. PCR reaction was carried out by repeating 40 cycles of the temperature shifts at 94° C. for 1 minute, at 55° C. for 2 minutes, and at 72° C. for 1.5 minutes, using the MF1F1 primer and the M13M4 primer included in the kit together with this cDNA as a template. Second PCR reaction (nested PCR reaction) was carried out using this PCR reaction mixture as a template. The MF1F2 primer and the M13M4 primer were used in this reaction. As a result of the PCR, a cDNA fragment with about 570 bp in length was amplified. This cDNA was cloned into a pUC118 vector (manufactured by Takara Shuzo Co., Ltd.), and its base sequence was then determined. The resulting base sequence is shown by SEQ ID NO:17 in Sequence Listing. The amino acid sequence deduced from SEQ ID NO:17 was identical to the amino acid sequence determined from the MF-1 protein. Therefore, it is clearly demonstrated that this cDNA fragment is an MF-1 gene.

11-c) Preparation of *M. furfur* cDNA library

20 μg of poly(A)$^+$ RNA was purified from 1 mg of the total RNA obtained in Example 11-a) with Oligotex-dT30 <SUPER> (manufactured by Takara Shuzo Co., Ltd.). A cDNA was synthesized by a cDNA synthesis kit (manufactured by Takara Shuzo Co., Ltd.) using 5 μg of the poly(A)$^+$ RNA. A cDNA library was constructed by ligating the synthesized cDNA and the lambda phage vector λSH1ox™ (manufactured by Novagen) together, and carrying out in vitro packaging using Phagemaker System and Phage Pack Extract (manufactured by Novagen).

11-d) Cloning of MF-1 cDNA

The cDNA library obtained in Example 11-c) was infected into a host *Escherichia coli* ER1647 strain and mixed with Top Agarose (an LB medium containing 0.7% bacto agar), and a plaque was then formed by overlaying on an LB plate and culturing at 37° C. overnight. The resulting plaque was transferred onto a nylon membrane ("Hybond-N," manufactured by Amersham) and subjected to plaque hybridization. A cDNA fragment of MF-1 with about 570 bp obtained in Example 11-b) was labeled with [α-$^{32}$P]dCTP using a random primer DNA labeling kit (manufactured by Takara Shuzo Co., Ltd.), and the labeled cDNA fragment was used as a probe for hybridization. 1.6×10$^5$ plaques were screened for, and 10 clones with strong signals out of the positive clones were then subjected to further analysis. Specifically, *E. coli* cells harbouring the plasmid which has a region containing the MF-1 cDNA were obtained from these phages by automatic subcloning in *E. coli*. The plasmids were purified from these *E. coli* cells, and pMF1-7, which contained the longest fragment with about 600 bp cDNA, was selected. The cDNA was subcloned into a pUC118 vector (manufactured by Takara Shuzo Co., Ltd.), and its base sequence was then determined. The base sequence thereof is shown by SEQ ID NO:1 in Sequence Listing, and the MF-1 gene encodes a polypeptide having an amino acid sequence as shown by SEQ ID NO:2 in Sequence Listing.

11-e) Purification of genomic DNA from *M. furfur*

In order to obtain a genomic DNA from cells of the *M. furfur* TIMM2782 strain, the strain was cultured for 72 hours in 200 ml of the YNB medium, and the cells were harvested by centrifugation at 3,000 rpm for 15 minutes. The harvested cells were washed with a washing solution (0.9% NaCl, 0.05% Tween 80) five times, and then with a PK buffer (0.15 M NaCl, 0.1 M Tris-HCl (pH 7.5), 10 mM EDTA) three times. The cells were suspended in 8 ml of the PK buffer, and an equivolume of glass beads (425 to 600 μm in diameter, manufactured by Sigma) was then added thereto, and the cells were disrupted using mini-bead beater (manufactured by Biospace). Protease K and SDS were added to the cell disruption, so as to have final concentrations of 0.15 mg/ml and 1% (w/v), respectively, and the resulting mixture was treated at 50° C. for 3 hours while gently stirring the mixture. The nucleic acid was purified by subjecting the disrupted solution to phenol extraction, phenol/chloroform extraction, and chloroform extraction (each carried out once), and subjected to ethanol precipitation. The nucleic acid obtained by centrifugation at 10,000 rpm for 15 minutes was dissolved in a TE buffer (10 mM Tris-HCl, 1 mM EDTA). RNase A was added to the nucleic acid solution so as to have a final concentration of 40 μg/ml, and the mixture was treated at 37° C. for 40 minutes. The DNA was recovered and purified by subjecting the solution to phenol extraction, phenol/chloroform extraction, and chloroform extraction (each carried out once), and by subjecting to ethanol precipitation.

11-f) Cloning of MF-1 genomic DNA

The genomic DNA obtained in Example 11-e) was completely cleaved with BamHI or PstI, and each of the resulting fragments was then cloned into the pUC118 vector to prepare two kinds of genomic DNA libraries. An MF-1 genomic DNA was screened from the libraries by colony hybridization using the MF-1 cDNA obtained in Example 11-d) as a probe. A clone containing an 8.5 kbp DNA was obtained from the library containing a BamHI fragment, and a clone containing a 4.9 kbp DNA was obtained from the library containing a PstI fragment. Based on the base sequence of the cDNA, the base sequence of the 4.9 kbp PstI fragment was determined. The base sequence of the genomic DNA containing the MF-1 gene is shown by SEQ ID NO:18 in Sequence Listing. According to this base sequence, the MF-1 gene encodes a polypeptide having an amino acid sequence as shown by SEQ ID NO:19 in Sequence Listing.

Further, it is made clear that there are two introns each with 37 bp and 39 bp in the genomic DNA. The relationship between the genomic DNA and the cDNA is shown in FIG. 23.

EXAMPLE 12

Cloning of Antigenic Protein MF-2 Gene from *M. furfur*

12-a) Amplification of MF-2 Gene by RT-PCR

The oligonucleotide MF2F1 deduced from the internal amino acid sequence of the MF-2 protein described in Example 10 was synthesized and purified to be used as a primer for PCR. The base sequence of MF2F1 is shown by SEQ ID NO:20 in Sequence Listing. An MF-2 cDNA fragment was amplified by carrying out RT-PCR according to the method described in Example 11-b) using the MF2F1 and M13M4 primers. As a result of the first PCR reaction, a cDNA fragment with about 280 bp in length was amplified. The base sequence of the cDNA fragment amplified is shown by SEQ ID NO:21 in Sequence Listing. The amino acid sequence deduced from SEQ ID NO:21 was identical to the amino acid sequence determined from the MF-2 protein. Therefore, it is clearly demonstrated that this cDNA fragment is an MF-2 gene.

12-b) Cloning of MF-2 cDNA

Plaque hybridization was carried out using the MF-2 cDNA fragment with about 280 bp as shown by SEQ ID NO:21 obtained in Example 12-a) as a probe according to the method described in Example 11-d). Ten clones with strong signals out of positive clones were subjected to further analysis. Specifically, *E. coli* cells harbouring the plasmid which has a region containing an MF-2 cDNA were obtained from these phages by automatic subcloning in *E. coli*. The plasmids were purified from these *E. coli* cells, and pMF2-2, which contained the longest fragment with about 550 bp cDNA, was selected. The cDNA was subcloned into a pUC118 vector, and its base sequence was then determined. The base sequence is shown by SEQ ID NO:3 in Sequence Listing, and the MF-2 gene encodes a polypeptide having an amino acid sequence as shown by SEQ ID NO:4 in Sequence Listing.

EXAMPLE 13

Cloning of Antigenic Protein MF-3 Gene from *M. furfur*

13-a) Amplification of MF-3 Gene by RT-PCR

The oligonucleotides MF3F1, MF3F2, and MF3F3 deduced from the internal amino acid sequence of the MF-3 protein described in Example 10 were synthesized and purified to be used as primers for PCR. The base sequences of MF3F1, MF3F2, and MF3F3 are shown by SEQ ID NOs,:22 to 24 in Sequence Listing, respectively. An MF-3 cDNA fragment was amplified by carrying out RT-PCR according to the method described in Example 11-b) using MF3F1 and M13M4 primers in the first PCR reaction, and using a combination of MF3F1 and MF3R3 primers and a combination of MF3F2 and M13M4 primers in the second PCR reaction. As a result of the PCR reaction, a cDNA fragment with about 380 bp in length was amplified for the combination of MF3F1 and MF3R3 primers, and a cDNA fragment with about 280 bp in length was amplified for the combination of MF3F2 and M13M4 primers. The base sequences of the cDNA fragment amplified are shown by SEQ ID NOs:25 and 26 in Sequence Listing, respectively. The amino acid sequences deduced from SEQ ID NOs:25 and 26 were identical to the amino acid sequence determined from the MF-3 protein. Therefore, it is clearly demonstrated that this cDNA fragment is an MF-3 gene.

13-b) Cloning of MF-3 cDNA

Plaque hybridization was carried out using the MF-3 cDNA fragment with about 380 bp as shown by SEQ ID NO:25 obtained in Example 13-a) as a probe according to the method described in Example 11-d). Six clones with strong signals out of positive clones were subjected to further analysis. Specifically, *E. coli* cells harbouring the plasmid which has a region containing an MF-3 cDNA were obtained from these phages by automatic subcloning in *E. coli*. The plasmids were purified from these *E. coli* cells, and pMF3-1, which contained the longest fragment with about 750 bp cDNA, was selected, and the base sequence of the cDNA was then determined. The base sequence is shown by SEQ ID NO:5 in Sequence Listing, and the MF-3 gene encodes a polypeptide having an amino acid sequence as shown by SEQ ID NO:6 in Sequence Listing.

EXAMPLE 14

Cloning of Antiaenic Protein MF-4 Gene from *M. furfur*

14-a) Amplification of MF-4 Gene by RT-PCR

The oligonucleotides MF4F1 and MF4F2 deduced from the N-terminal amino acid sequence of the MF-4 protein described in Example 10 were synthesized and purified to be used as primers for PCR. The base sequences of MF4F1 and MF4F2 are shown by SEQ ID NOs:27 and 28 in Sequence Listing, respectively. An MF-4 cDNA fragment was amplified by carrying out RT-PCR according to the method described in Example 11-b). MF4F1 and M13M4 primers were used in the first PCR reaction, and MF4F1 and M13M4 primers were used in the second PCR reaction. As a result of the PCR reaction, a cDNA fragment with about 700 bp in length was amplified. The base sequence of the cDNA fragment amplified is shown by SEQ ID NO:29 in Sequence Listing. The amino acid sequence deduced from SEQ ID NO:29 was identical to the amino acid sequence determined from the MF-4 protein. Therefore, it is clearly demonstrated that this cDNA fragment is an MF-4 gene.

14-b) Cloning of MF-4 cDNA

Plaque hybridization was carried out using the MF-4 cDNA fragment with about 700 bp as shown by SEQ ID NO:29 obtained in Example 14-a) as a probe according to the method described in Example 11-d). Four clones with strong signals out of positive clones were subjected to further analysis. Specifically, *E. coli* cells harbouring the plasmid which has a region containing an MF-4 cDNA were obtained from these phages by automatic subcloning in *E. coli*. The plasmids were purified from these *E. coli* cells, and pMF4-4, which contained the longest fragment with about 820 bp cDNA, was selected, and the base sequence of the cDNA was then determined. The base sequence is shown by SEQ ID NO:7 in Sequence Listing, and the MF-4 gene encodes a polypeptide having an amino acid sequence as shown by SEQ ID NO:8 in Sequence Listing.

EXAMPLE 15

Cloning of Antigenic Protein MF-5 Gene from *M. furfur*

15-a) Amplification of MF-5 Gene by RT-PCR

DNAd on the N-terminal amino acid sequence of the MF-5 protein described in Example 10, since the protein was thought to share homologies with DLDH, the oligonucleotide mixture MF5F1 encoding the amino acid sequence GYVAAIKA DNAd on the above amino acid sequence and the DLDH amino acid sequence of other living organisms, and the oligonucleotide MF5R2 corresponding to a highly homologous region (amino acid sequence MLAHKAEE) when compared with DLDH amino acid sequences between other living organisms were synthesized and purified to be used as primers for PCR. The base sequences of MF5F1 and MF5F2 are shown by SEQ ID NOs:30 and 31 in Sequence Listing, respectively. An MF-5 cDNA fragment was amplified by carrying out RT-PCR according to the method described in Example 11-b). MF5F1 and M13M4 primers were used in the first PCR reaction, and MF5F1 and MF5R2 primers were used in the second PCR reaction. As a result of the PCR reaction, a cDNA fragment with about 900 bp in length was amplified. The base sequence of the cDNA fragment amplified is shown by SEQ ID NO:32 in Sequence Listing. The amino acid sequence deduced from SEQ ID NO:32 was identical to the amino acid sequence determined from the MF-5 protein. Therefore, it is clearly demonstrated that this cDNA fragment is an MF-5 gene.

15-b) Cloning of MF-5 cDNA

Plaque hybridization was carried out using the MF-5 cDNA fragment with about 900 bp as shown by SEQ ID NO:32 obtained in Example 15-a) as a probe according to the method described in Example 11-d). Twelve clones with strong signals out of positive clones were subjected to further analysis. Specifically, *E. coli* cells harbouring the plasmid which has a region containing an MF-5 cDNA were obtained from these phages by automatic subcloning in *E. coli*. The plasmids were purified from these *E. coli* cells, and pMF5-6 and pMF5-7, which contained the longest fragment with about 1.6 kbp cDNA, was selected, and the base sequence of the cDNA was then determined. The base sequences are shown by SEQ ID NOs:5 and 33 in Sequence Listing, and the MF-5 gene encodes a polypeptide having an amino acid sequence as shown by SEQ ID NOs:12 and 34 in Sequence Listing. These two kinds of genes have homology of 92% in the base sequence, and 96% in the amino acid sequence encoding thereof, and were substantially identical to the amino acid sequence determined from the MF-5 protein. Therefore, it is clearly demonstrated that both of the genes are an MF-5 gene.

EXAMPLE 16

Cloning of Antigenic Protein MF-6 Gene from *M. furfur*

16-a) Amplification of MF-6 Gene by RT-PCR

The oligonucleotide mixtures MF6F1 and MF6F2 deduced from the N-terminal amino acid sequence of the MF-6 protein described in Example 10 were synthesized and purified to be used as primers for PCR. The base sequences of MF6F1 and MF6F2 are shown by SEQ ID NOs:35 and 36 in Sequence Listing, respectively. An MF-6 cDNA fragment was amplified by carrying out RT-PCR according to the method described in Example 11-b). MF6F1 and M13M4 primers were used in the first PCR reaction, and MF6F2 and M13M4 primers were used in the second PCR reaction. As a result of the PCR reaction, a cDNA fragment with about 1.0 kbp in length was amplified. The amplified cDNA fragment was cloned into a pUC118 vector, and as a result, two kinds of cDNA having different cleavage patterns of restriction enzymes were detected. The base sequences of these cDNA fragments are shown by SEQ ID NOs:37 and 38 in Sequence Listing. Although these two genes have homology of 90% in the base sequence, and 94% in the amino acid sequence deduced from the base sequence, they are different genes. The amino acid sequences deduced from SEQ ID NOs:37 and 38 were nearly identical to the amino acid sequence determined from the MF-6 protein described in Example 10. Therefore, it is clearly demonstrated that this cDNA fragment is an MF-6 gene.

16-b) Cloning of MF-6 cDNA

Plaque hybridization was carried out using the MF-6 cDNA fragments with about 1.0 kbp as shown by SEQ ID NOs:37 and 38 obtained in Example 16-a) as probes according to the method described in Example 11-d). Ten clones with strong signals out of positive clones were subjected to further analysis. Specifically, *E. coli* cells harbouring the plasmid which has a region containing an MF-6 cDNA were obtained from these phages by automatic subcloning in *E. coli*. The plasmids were purified from these *E. coli* cells, and pMF6-13, which contained the longest fragment with about 1.2 kbp cDNA, was selected, and the base sequence of the cDNA was then determined. The base sequence is shown by SEQ ID NO:4 in Sequence Listing, and the MF-6 gene encodes a polypeptide having an amino acid sequence as shown by SEQ ID NO:12 in Sequence Listing. Although this gene lacks a encoding region of N-terminal amino acid sequence, it was nearly identical to the cDNA fragment of MF-6 obtained in Example 16-a). Therefore, it is clearly demonstrated that this cDNA fragment is an MF-6 gene.

EXAMPLE 17

Cloning of Antigenic Protein MF-7 Gene from *M. furfur*

17-a) Amplification of MF-7 Gene by RT-PCR

The oligonucleotide mixtures MF7F1 and MF7F2 deduced from the N-terminal amino acid sequence of the MF-7 protein described in Example 10 were synthesized and purified to be used as primers for PCR. The base sequences of MF7F1 and MF7F2 are shown by SEQ ID NOs:39 and 40 in Sequence Listing, respectively. An MF-7 cDNA fragment was amplified by carrying out RT-PCR according to the method described in Example 11-b). MF7F1 and M13M4 primers were used in the first PCR reaction, and MF7F2 and M13M4 primers were used in the second PCR reaction. As a result of the PCR reaction, a cDNA fragment with about 0.4 kbp in length was amplified. The amplified cDNA fragment was cloned into a pUC118 vector. The base sequence of the cDNA fragment amplified is shown by SEQ ID NO:41 in Sequence Listing. The amino acid sequence deduced from SEQ ID NO:41 was nearly identical to the amino acid sequence determined from the MF-7 protein described in Example 10. Therefore, it is clearly demonstrated that this cDNA fragment is an MF-7 gene.

17-b) Cloning of MF-7 cDNA

Plaque hybridization was carried out using the MF-7 cDNA fragment with about 0.4 kbp as shown by SEQ ID NO:41 obtained in Example 17-a) as a probe according to the method described in Example 11-d). Five clones with strong signals out of positive clones were subjected to further analysis. Specifically, *E. coli* cells harbouring the plasmid which has a region containing an MF-7 cDNA were obtained from these phages by automatic subcloning in *E. coli*. The plasmids were purified from these *E. coli* cells, and pMF7-1, which contained the longest with about 0.4 kbp cDNA, was selected, and the base sequence of the cDNA was then determined. The base sequence is shown by SEQ ID NO:13 in Sequence Listing, and the MF-7 gene encodes a polypeptide having an amino acid sequence as shown by SEQ ID NO:14 in Sequence Listing.

EXAMPLE 18

Synthesis of MF-1 Overlap Peptides and Deduction of Antigen-Binding Sites 18-a) Synthesis of MF-1 Overlap Peptides MF-1 overlap peptides were synthesized using a peptide synthesizer (PSSM-8, manufactured by Shimadzu Corporation). The entire amino acid sequence was covered by 33 kinds of peptides on the basis of the sequence of MF-1, as shown by SEQ ID NO:2 (FIG. 21), each peptide consisting of 15 (16 or 17 in some cases) amino acid residues, and being overlapped with 10 amino acid residues.

First, a resin (50 mg) previously coupled with the Fmoc form of the C-terminal amino acid of each peptide (0.2 to 0.5 mmol/g resin) was treated with 30% piperidine/DMF (0.5 ml) to remove the Fmoc group. After the resin was washed with DMF (0.6 ml×5 times), the Fmoc form of the desired amino acid activated with PyBOP and HOBt (used in DMF solution containing the Fmoc in excess by 10 times relative to the amount of the C-terminal amino acid content) and an N-methylmorpholine/DMF solution were added, followed by a reaction at room temperature for 30 minutes. The resin was then washed with DMF (0.6 ml×5 times). This series of procedures were repeated in cycles until a peptide having the desired sequence was obtained.

Next, this resin was admixed with a TFA-DNAd mixed solution (94% TFA, 5% anisole, 1% ethanedithiol (EDT)) (0.7 ml) and kept standing at room temperature for 2 hours (for tryptophan-containing peptides, a mixed solution of TFA (94%), anisole (3%), EDT (3%), and 2-methylindole (5 mg) being used; for arginine-containing peptides, a mixed solution of TFA (82%), $H_2O$ (5%), thioanisole (5%), EDT (3%), ethylmethyl sulfide (2%), and phenol (3%) being used; in the case for the arginine-containing peptides, the resin was kept standing at room temperature for 8 hours). The resin was filtered off, and ethyl ether (14 ml) was added to the filtrate to allow crystallization. The precipitated crystals were recovered by centrifugation (3,000 rpm, 10 minutes) and washed with ethyl ether, and they were then centrifuged again to remove the supernatant, and the crystals were dried under reduced pressure. The obtained crystals were assayed for its purity by reversed-phase HPLC. In addition, as occasion demands, the molecular weight was confirmed by LC-MS, and the crystals were purified by reversed-phase HPLC.

18-b) Identification of Binding Peptides to IgE Antibodies in Human Sera

Figure 22:
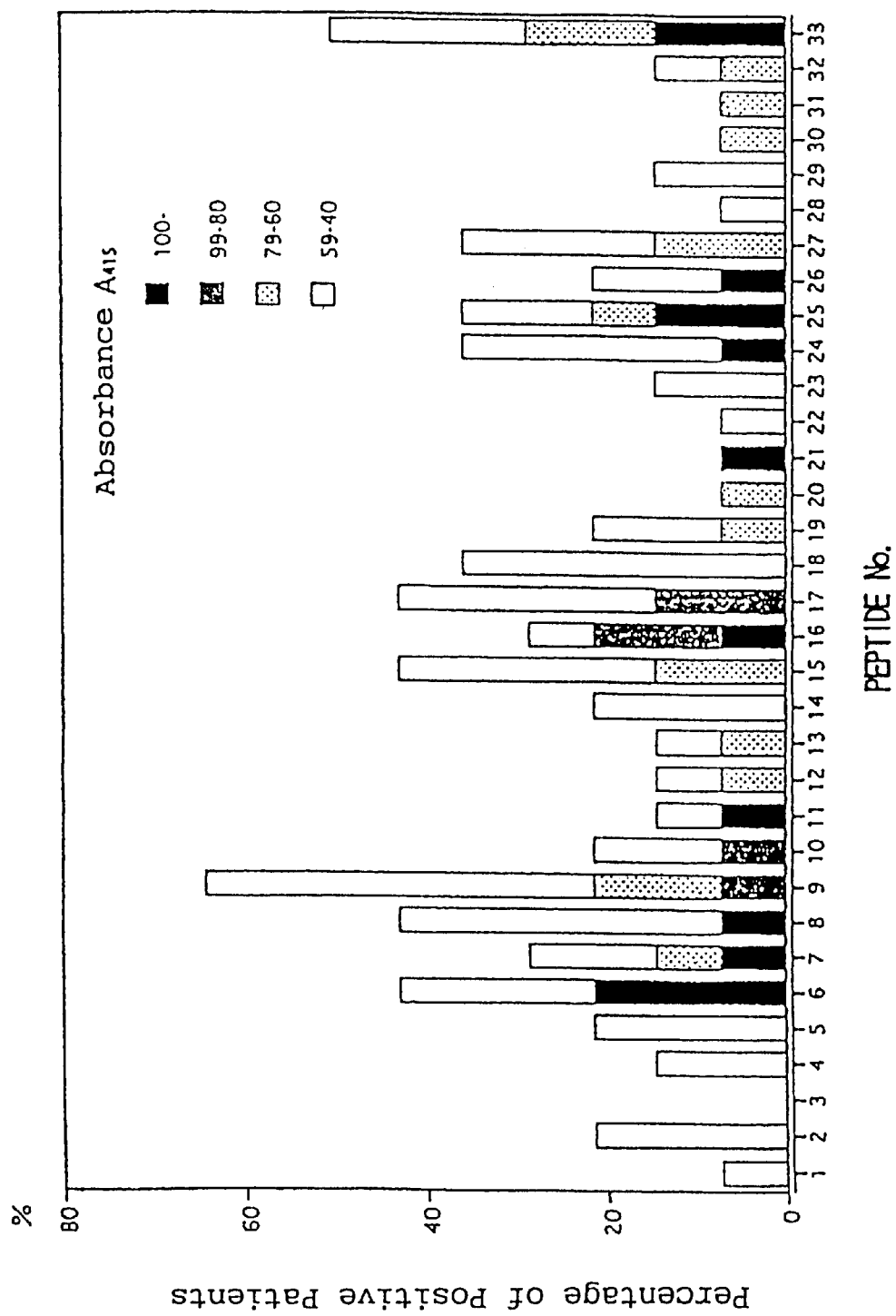
FIG. 22 is a graph showing the reaction between the MF-1 overlapping peptides and RAST positive patient sera of M. furfur.

Each of the peptides shown in FIG. 21 coated on a 96-well microplate at 1 μg/well using a peptide coating kit (manufactured by Takara Shuzo Co., Ltd.). A 2-fold dilution of each of 14 sera in total out of 13 sera from patients with *M. furfur* RAST positive, and 1 pooled serum was added to each well. After the reaction was carried out according to the manual, a β-galactosidase-labeled anti-IgE antibody and then an enzyme substrate were added, followed by absorbance measurement at 415 nm. The absorbance as used sera from normal individuals for 33 peptides was 20 on the average. A positive group was defined as those showing absorbance of not less than 40, which is 2-folds that of the sera from the normal individuals. The positive group having absorbance of not less than 40 was further classified into four ranks, and the results are shown in FIG. 22. The sera of patients with *M. furfur* RAST positive reacted strongly to four to five kinds of peptide fragments.

18-c) Estimation of Epitopes of Mouse Monoclonal Antibodies Against MF-1

After three monoclonal antibodies against MF-1, i.e., M-40, MmAb37, and MAb51, were added to, and reacted with, microplates coated with each of the peptides of FIG. 21 described in Example 18-b), a peroxidase-labeled anti-IgG antibody and then an enzyme substrate were added, followed by absorbance measurement at 450 nm. M-40 and MmAb37 reacted to Peptide 5, while MAb51 reacted to Peptides 25 and 26. In consideration of the above findings in combination with the results of FIG. 22, it was made clear that these peptides contained B cell epitope.

EXAMPLE 19

Application of Recombinant Malassezia Antiqenic Proteins for Diagnosis 19-a) Method for Measuring Specific IgE Antibodies by RAST Method Activation of a paper disc with cyanogen bromide and coupling of the recombinant Malassezia antigenic protein to the paper disc were carried out according to the method of Miyamoto et al. (*Allergy*, 22, 584–594, 1973). One paper disc, previously coupled with the above antigenic protein, and 50 μl of sera from patients were added to a polystyrene tube, followed by incubation at room temperature for 3 hours. The paper disc was washed three times with a physiological saline containing 0.2% Tween 20, and 50 μl of the $^{125}$I-labeled anti-human IgE antibody of the RAST-RIA kit, manufactured by Pharmacia, was added, followed by incubation at room temperature overnight. After the disc was washed three times again, radioactivity was assayed using a gamma counter. The IgE antibody titer was calculated from a standard curve drawn using a reference reagent of the kit at the same time. Specimens yielding values exceeding the upper limit of the standard curve (>17.5 PRU/ml) were diluted 10 folds or 100 folds with equine serum and assayed again, followed by calculation of their antibody titer.

19-b) Diagnosis Using Recombinant Malassezia Antigenic Proteins rMF-1, rMF-2, and rMF-4

A skin test using the above antigenic proteins was performed on patients with atopic dermatitis (hereinafter abbreviated AD) or bronchial asthma (hereinafter abbreviated BA) or both complications (AD+BA). Forty-three out of 57 for the AD patients (75%), 108 out of 919 for the BA patients (12%), and 47 out of 102 for the AD+BA patients (46%) were positive patients, showing a very high ratio for positive in the AD patients. Also, 100%, 59%, and 85% of these AD, BA, and AD+BA patients with positive for skin tests, respectively, were positive in IgE antibody measurement by RAST method.

The IgE antibody titers for three kinds of the recombinant antigenic proteins rMF-1, rMF-2, and rMF-4 were assayed by RAST method (RIA method) on the 76 cases of patients with positive in the skin test using the above antigenic proteins and positive in RAST (1 or higher score) (AD: 30 patients, BA: 20 patients, AD+BA: 26 patients) as an object for measurement. The IgE antibody titers for the above antigenic proteins were assayed in the same manner on 12 negative individuals in the skin tests (normal individuals). As a result, it was made obvious that the IgE antibodies against antigenic proteins were present in the sera from patients at very high ratios. Especially, it was found that ratios of positive for rMF-1 and rMF-2 were high. In addition, surprisingly, the IgE antibody titers were very high. And especially in the case of the AD patients, the IgE antibody titers were 100 PRU on average, with values exceeding 1,000 PRU in some patients. Also, the IgE antibody against any one of the recombinant antigenic proteins rMF-1, rMF-2, and rMF-4 was present in the sera from all patients with RAST-positive for the Malassezia antigens.

INDUSTRIAL APPLICABILITY

According to the present invention, there can be provided an isolated and purified antigenic protein having high purity from Malassezia, antigenic fragments thereof, and a specific antibody against those antigenic protein or fragments thereof. In addition, there can be provided a diagnostic agent, a therapeutic agent, or a prophylactic drug for Malassezia allergoses, wherein the agent includes, as an active ingredient, the antigenic protein or fragments thereof.

Further, according to the present invention, there can be provided a novel recombinant Malassezia antigenic protein, genes encoding the antigenic protein, and an epitope of the antigenic protein.

What is claimed is:

1. An isolated and purified antigenic protein from fungi of the genus Malassezia, wherein said antigenic protein has a molecular weight selected from the group consisting of 30 kDa, 40 kDa, 45 kDa, and 100 kDa as determined by SDS-PAGE under reduced conditions and an isoelectric point selected from the group consisting of 5.4, 5.3, 6.4, and 5.0, respectively, in a denatured state as determined by isoelectric electrophoresis with 8 M urea, and wherein the antigenic protein has a binding affinity to IgE antibodies from patients with allergies.

2. The antigenic protein according to claim 1, wherein said antigenic protein is a major allergen from Malassezia and is reactive to patients with allergies showing a positive reaction in a skin test to a crude antigen of Malassezia.

3. The antigenic protein according to claim 1, wherein said antigenic protein is extracted from fungal cells of the genus Malassezia.

4. The antigenic protein from Malassezia according to claim 1, wherein said antigenic protein has a molecular weight of about 30 kDa as determined by SDS-PAGE under reduced conditions, and an isoelectric point of about 5.4 in a denatured state with 8 M urea, and that the N-terminus of said protein is blocked.

5. The antigenic protein from Malassezia according to claim 1, wherein said antigenic protein has a molecular weight of about 40 kDa as determined by SDS-PAGE under reduced conditions, and an isoelectric point of about 5.3 in a denatured state with 8 M urea.

6. The antigenic protein from Malassezia according to claim 1, wherein said antigenic protein has a molecular weight of about 45 kDa as determined by SDS-PAGE under reduced conditions, and an isoelectric point of about 6.4 in a denatured state with 8 M urea, and that the N-terminus of said protein is blocked.

7. The antigenic protein from Malassezia according to claim 1, wherein said antigenic protein has a molecular weight of about 100 kDa as determined by SDS-PAGE under reduced conditions, and an isoelectric point of about 5.0 in a denatured state with 8 M urea.

8. A recombinant Malassezia antigenic protein, wherein said recombinant antigenic protein has a molecular weight selected from the group consisting of 30 kDa, 40 kDa, 45 kDa, and 100 kDa as determined by SDS-PAGE under reduced conditions and an isoelectric point selected from the group consisting of 5.4, 5.3, 6.4, and 5.0, respectively, in a denatured state as determined by isoelectric electrophoresis wish 8 M urea, wherein said antigenic protein has a binding affinity to IgE antibodies from patients with allergies.

9. The recombinant Malassezia antigenic protein according to claim 8, wherein said antigenic protein is a peptide having an entire sequence of the amino acid sequence as shown by SEQ ID NO:2.

10. The recombinant Malassezia antigenic protein according to claim 8, wherein said antigenic protein comprises SEQ ID NO: 2, wherein said antigenic protein has a binding affinity to IgE antibodies from patients with allergies.

11. A diagnostic agent for Malassezia allergies or Malassezia infectious diseases, wherein said diagnostic agent includes, as a biologically active ingredient, the antigenic protein according to claim 1 or the recombinant Malassezia antigenic protein according to claim 8.

12. A therapeutic agent for Malassezia allergies or Malassezia infectious diseases, wherein said therapeutic agent includes, as a biologically active ingredient, the antigenic protein according to claim 1, or the recombinant Malassezia antigenic protein according to claim 8.

13. A method for quantifying the amount of Malassezia allergen in a sample comprising patient sera, comprising the steps of contacting the sample with antibodies against the antigenic protein according to claim 1 or the recombinant Malassezia antigenic protein according to claim 8 in an Enzyme-Linked Immunosorbent Assay (ELISA); and quatifying the amount of Malassezia allergen by standard immunological means of measuring an ELISA.

* * * * *

SEQUENCE LISTING (1) GENERAL INFORMATION:

(iii) NUMBER OF SEQUENCES: 58

(2) INFORMATION FOR SEQ ID NO:1:

(i) SEQUENCE CHARACTERISTICS:
        (A) LENGTH: 618 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 2..529

(xi) SEQUENCE DESCRIPTION: SEQ ID NO:1:

```
G CCT GGT GAT CCT ACT GCT ACT GCC AAG GGT AAC GAG ATC CCC GAC        46
  Pro Gly Asp Pro Thr Ala Thr Ala Lys Gly Asn Glu Ile Pro Asp
  1               5                  10                  15

ACC CTC ATG GGC TAC ATC CCC TGG ACC CCG GAG CTC GAC TCG GGT GAG      94
Thr Leu Met Gly Tyr Ile Pro Trp Thr Pro Glu Leu Asp Ser Gly Glu
                20                  25                  30

GTG TGT GGT ATC CCC ACC ACC TTC AAG ACC CGC GAC GAG TGG AAG GGC      142
Val Cys Gly Ile Pro Thr Thr Phe Lys Thr Arg Asp Glu Trp Lys Gly
                35                  40                  45
```

```
AAG AAG GTT GTG ATT GTC TCG ATC CCG GGT GCC TAC ACC CCC ATC TGC      190
Lys Lys Val Val Ile Val Ser Ile Pro Gly Ala Tyr Thr Pro Ile Cys
         50                  55                  60

CAC CAG CAG CAC ATC CCC CCG CTT GTG AAG CGT GTG GAT GAG CTC AAG      238
His Gln Gln His Ile Pro Pro Leu Val Lys Arg Val Asp Glu Leu Lys
 65                  70                  75

GCC AAG GGT GTC GAC GCC GTG TAC GTC ATT GCG TCG AAC GAC CCC TTC      286
Ala Lys Gly Val Asp Ala Val Tyr Val Ile Ala Ser Asn Asp Pro Phe
 80                  85                  90                  95

GTC ATG GCT GCC TGG GGC AAC TTC AAC AAC GCC AAG GAC AAG GTC GTC      334
Val Met Ala Ala Trp Gly Asn Phe Asn Asn Ala Lys Asp Lys Val Val
                 100                 105                 110

TTT GCC ACC GAC ATT GAC CTG GCC TTC TCC AAG GCT CTC GGC GCG ACG      382
Phe Ala Thr Asp Ile Asp Leu Ala Phe Ser Lys Ala Leu Gly Ala Thr
                 115                 120                 125

ATC GAC CTG AGC GCC AAG CAC TTT GGT GAG CGC ACG GCC CGC TAC GCT      430
Ile Asp Leu Ser Ala Lys His Phe Gly Glu Arg Thr Ala Arg Tyr Ala
        130                 135                 140

CTG ATC ATT GAC GAC AAC AAG ATT GTC GAC TTT GCT TCG GAC GAG GGC      478
Leu Ile Ile Asp Asp Asn Lys Ile Val Asp Phe Ala Ser Asp Glu Gly
        145                 150                 155

GAC ACT GGC AAG CTC CAG AAC GCG TCG ATC GAC ACG ATC CTC ACC AAG      526
Asp Thr Gly Lys Leu Gln Asn Ala Ser Ile Asp Thr Ile Leu Thr Lys
160                 165                 170                 175

GTC TAAAATGGCG CATGTGCGTT GTGTGACCAC TACCTAAAGG GTCCGTAGAG           579
Val

TTCCAAGTCA AGTCGTATAT TTTTTTTTTA AAAAAAAAA                           618
```

(2) INFORMATION FOR SEQ ID NO:2:

(i) SEQUENCE CHARACTERISTICS:
        (A) LENGTH: 176 amino acids
        (B) TYPE: amino acid
        (D) TOPOLOGY: linear (ii) MOLECULE TYPE: protein (xi) SEQUENCE DESCRIPTION: SEQ ID NO:2:

```
Pro Gly Asp Pro Thr Ala Thr Ala Lys Gly Asn Glu Ile Pro Asp Thr
 1               5                  10                  15

Leu Met Gly Tyr Ile Pro Trp Thr Pro Glu Leu Asp Ser Gly Glu Val
                 20                  25                  30

Cys Gly Ile Pro Thr Thr Phe Lys Thr Arg Asp Glu Trp Lys Gly Lys
         35                  40                  45

Lys Val Val Ile Val Ser Ile Pro Gly Ala Tyr Thr Pro Ile Cys His
 50                  55                  60

Gln Gln His Ile Pro Pro Leu Val Lys Arg Val Asp Glu Leu Lys Ala
 65                  70                  75                  80

Lys Gly Val Asp Ala Val Tyr Val Ile Ala Ser Asn Asp Pro Phe Val
                 85                  90                  95

Met Ala Ala Trp Gly Asn Phe Asn Asn Ala Lys Asp Lys Val Val Phe
                 100                 105                 110

Ala Thr Asp Ile Asp Leu Ala Phe Ser Lys Ala Leu Gly Ala Thr Ile
        115                 120                 125

Asp Leu Ser Ala Lys His Phe Gly Glu Arg Thr Ala Arg Tyr Ala Leu
        130                 135                 140

Ile Ile Asp Asp Asn Lys Ile Val Asp Phe Ala Ser Asp Glu Gly Asp
145                 150                 155                 160
```

```
        Thr Gly Lys Leu Gln Asn Ala Ser Ile Asp Thr Ile Leu Thr Lys Val
                    165                 170                 175
```

(2) INFORMATION FOR SEQ ID NO:3:

(i) SEQUENCE CHARACTERISTICS:
        (A) LENGTH: 551 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 3..500

(xi) SEQUENCE DESCRIPTION: SEQ ID NO:3:

```
CG GAA ATT GGC TCG ACG ATC CCC AAC GCT ACG TTT GCA TAC GTG CCG        47
   Glu Ile Gly Ser Thr Ile Pro Asn Ala Thr Phe Ala Tyr Val Pro
     1               5                  10                  15

TAC AGC CCC GAG CTC GAG GAC CAC AAA GTG TGT GGC ATG CCG ACG AGC       95
Tyr Ser Pro Glu Leu Glu Asp His Lys Val Cys Gly Met Pro Thr Ser
                20                  25                  30

TTC CAG AGC CAC GAG CGC TGG AAG GGC AAG AAG GTG GTG ATT GTC GCG      143
Phe Gln Ser His Glu Arg Trp Lys Gly Lys Lys Val Val Ile Val Ala
            35                  40                  45

GTG CCC GGT GCG TTC ACG CCG ACG TGC ACC GCG AAC CAT GTG CCG CCG      191
Val Pro Gly Ala Phe Thr Pro Thr Cys Thr Ala Asn His Val Pro Pro
        50                  55                  60

TAC GTG GAA AAG ATC CAG GAG CTC AAG AGC AAG GGC GTC GAC GAG GTC      239
Tyr Val Glu Lys Ile Gln Glu Leu Lys Ser Lys Gly Val Asp Glu Val
    65                  70                  75

GTG GTG ATC TCG GCG AAC GAC CCG TTC GTG CTG AGC GCA TGG GGC ATC      287
Val Val Ile Ser Ala Asn Asp Pro Phe Val Leu Ser Ala Trp Gly Ile
 80                  85                  90                  95

ACC GAG CAC GCC AAG GAC AAC CTG ACG TTT GCG CAG GAC GTC AAC TGC      335
Thr Glu His Ala Lys Asp Asn Leu Thr Phe Ala Gln Asp Val Asn Cys
                100                 105                 110

GAG TTC TCC AAG CAC TTT AAC GCG ACG CTG GAC CTG TCG TCG AAG GGC      383
Glu Phe Ser Lys His Phe Asn Ala Thr Leu Asp Leu Ser Ser Lys Gly
            115                 120                 125

ATG GGC CTG CGC ACC GCG CGC TAC GCG CTG ATC GCG AAC GAC CTC AAG      431
Met Gly Leu Arg Thr Ala Arg Tyr Ala Leu Ile Ala Asn Asp Leu Lys
        130                 135                 140

GTC GAG TAC TTT GGC ATC GAC GAG GGC GAG CCG AAG CAG TCG TCG GCC      479
Val Glu Tyr Phe Gly Ile Asp Glu Gly Glu Pro Lys Gln Ser Ser Ala
145                 150                 155

GCG ACG GTG CTG AGC AAG CTG TAGTGCCGTT CTACTTAGTC AAACAATCGG         530
Ala Thr Val Leu Ser Lys Leu
160                 165

GTATAGTCGC GTAAAAAAAA A                                              551
```

(2) INFORMATION FOR SEQ ID NO:4:

(i) SEQUENCE CHARACTERISTICS:
        (A) LENGTH: 166 amino acids
        (B) TYPE: amino acid
        (D) TOPOLOGY: linear (ii) MOLECULE TYPE: protein (xi) SEQUENCE DESCRIPTION: SEQ ID NO:4:

```
Glu Ile Gly Ser Thr Ile Pro Asn Ala Thr Phe Ala Tyr Val Pro Tyr
1               5                   10                  15

Ser Pro Glu Leu Glu Asp His Lys Val Cys Gly Met Pro Thr Ser Phe
            20                  25                  30

Gln Ser His Glu Arg Trp Lys Gly Lys Lys Val Val Ile Val Ala Val
        35                  40                  45

Pro Gly Ala Phe Thr Pro Thr Cys Thr Ala Asn His Val Pro Pro Tyr
    50                  55                  60

Val Glu Lys Ile Gln Glu Leu Lys Ser Lys Gly Val Asp Glu Val Val
65                  70                  75                  80

Val Ile Ser Ala Asn Asp Pro Phe Val Leu Ser Ala Trp Gly Ile Thr
                85                  90                  95

Glu His Ala Lys Asp Asn Leu Thr Phe Ala Gln Asp Val Asn Cys Glu
                    100                 105                 110

Phe Ser Lys His Phe Asn Ala Thr Leu Asp Leu Ser Ser Lys Gly Met
                115                 120                 125

Gly Leu Arg Thr Ala Arg Tyr Ala Leu Ile Ala Asn Asp Leu Lys Val
        130                 135                 140

Glu Tyr Phe Gly Ile Asp Glu Gly Pro Lys Gln Ser Ser Ala Ala
145                 150                 155                 160

Thr Val Leu Ser Lys Leu
                165
```

(2) INFORMATION FOR SEQ ID NO:5:

(i) SEQUENCE CHARACTERISTICS:
        (A) LENGTH: 728 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..618

(xi) SEQUENCE DESCRIPTION: SEQ ID NO:5:

```
GGG AAC GTC ATG ACT GAG TAC ACT CTC CCT CCT CTG CCC TAC GCC TAC     48
Gly Asn Val Met Thr Glu Tyr Thr Leu Pro Pro Leu Pro Tyr Ala Tyr
1               5                   10                  15

GAT GCG CTG GAG CCG TTT ATC TCT AAG GAG ATC ATG ACG GTC CAC CAC     96
Asp Ala Leu Glu Pro Phe Ile Ser Lys Glu Ile Met Thr Val His His
            20                  25                  30

GAC AAG CAC CAC CAG ACC TAC GTG AAC AAC CTC AAC GCC GCC GAG AAG    144
Asp Lys His His Gln Thr Tyr Val Asn Asn Leu Asn Ala Ala Glu Lys
        35                  40                  45

GCG TAC GCT GAG GCG ACG GCC GCG AAC GAC GTG CTT AAG CAG ATC CAG    192
Ala Tyr Ala Glu Ala Thr Ala Ala Asn Asp Val Leu Lys Gln Ile Gln
    50                  55                  60

CTG CAG AGT GCG ATC AAG TTC AAC GGC GGT GGC CAC ATC AAC CAC TCG    240
Leu Gln Ser Ala Ile Lys Phe Asn Gly Gly Gly His Ile Asn His Ser
65                  70                  75                  80

CTG TTC TGG AAG AAC CTG GCC CCC CAG AGC GAG GGT GGT GGC CAA CTG    288
Leu Phe Trp Lys Asn Leu Ala Pro Gln Ser Glu Gly Gly Gly Gln Leu
                85                  90                  95

AAC GAT GGC CCT CTC AAG CAG GCC ATC GAG CAG GAG TTC GGC GAC TTT    336
Asn Asp Gly Pro Leu Lys Gln Ala Ile Glu Gln Glu Phe Gly Asp Phe
                    100                 105                 110
```

```
GAG AAG TTC AAG ACG ACC TTC AAC ACG AAG GCG GCC GGC ATC CAG GGT    384
Glu Lys Phe Lys Thr Thr Phe Asn Thr Lys Ala Ala Gly Ile Gln Gly
            115                 120                 125

TCG GGC TGG CTG TGG CTC GGT GTT GCC CCG ACG GGC AAC CTC GAC CTG    432
Ser Gly Trp Leu Trp Leu Gly Val Ala Pro Thr Gly Asn Leu Asp Leu
130                 135                 140

GTC GTT GCC AAG GAC CAG GAC CCG CTC ACG ACG CAC CAC CCC GTC ATT    480
Val Val Ala Lys Asp Gln Asp Pro Leu Thr Thr His His Pro Val Ile
145                 150                 155                 160

GGC TGG GAT GGC TGG GAG CAC GCC TGG TAC CTG CAG TAC AAG AAC GAC    528
Gly Trp Asp Gly Trp Glu His Ala Trp Tyr Leu Gln Tyr Lys Asn Asp
            165                 170                 175

AAG GCT TCC TAC CTT AAG GCC TGG TGG AAC GTG GTG AAC TGG GCC GAG    576
Lys Ala Ser Tyr Leu Lys Ala Trp Trp Asn Val Val Asn Trp Ala Glu
180                 185                 190

GCC GAG AAG CGC TTC CTC GAG GGT AAG AAG AAG GCC CAG CTG             618
Ala Glu Lys Arg Phe Leu Glu Gly Lys Lys Lys Ala Gln Leu
            195                 200                 205

TAATGGCACG TTTGTAGATG ATGAACGACA CACGATTTTA GGTCGCACGG CCGAGGCTAC   678

TAAAAAAAAA AAAAAAAAA AAAAAAAAAA AAAAAAAAAA AAAAAAAAAA               728

(2) INFORMATION FOR SEQ ID NO:6:

(i) SEQUENCE CHARACTERISTICS:
        (A) LENGTH: 206 amino acids
        (B) TYPE: amino acid
        (D) TOPOLOGY: linear (ii) MOLECULE TYPE: protein (xi) SEQUENCE DESCRIPTION: SEQ ID NO:6:

Gly Asn Val Met Thr Glu Tyr Thr Leu Pro Pro Leu Pro Tyr Ala Tyr
1               5                   10                  15

Asp Ala Leu Glu Pro Phe Ile Ser Lys Glu Ile Met Thr Val His His
            20                  25                  30

Asp Lys His His Gln Thr Tyr Val Asn Asn Leu Asn Ala Ala Glu Lys
        35                  40                  45

Ala Tyr Ala Glu Ala Thr Ala Ala Asn Asp Val Leu Lys Gln Ile Gln
    50                  55                  60

Leu Gln Ser Ala Ile Lys Phe Asn Gly Gly Gly His Ile Asn His Ser
65                  70                  75                  80

Leu Phe Trp Lys Asn Leu Ala Pro Gln Ser Glu Gly Gly Gly Gln Leu
                85                  90                  95

Asn Asp Gly Pro Leu Lys Gln Ala Ile Glu Gln Glu Phe Gly Asp Phe
            100                 105                 110

Glu Lys Phe Lys Thr Thr Phe Asn Thr Lys Ala Ala Gly Ile Gln Gly
        115                 120                 125

Ser Gly Trp Leu Trp Leu Gly Val Ala Pro Thr Gly Asn Leu Asp Leu
    130                 135                 140

Val Val Ala Lys Asp Gln Asp Pro Leu Thr Thr His His Pro Val Ile
145                 150                 155                 160

Gly Trp Asp Gly Trp Glu His Ala Trp Tyr Leu Gln Tyr Lys Asn Asp
                165                 170                 175

Lys Ala Ser Tyr Leu Lys Ala Trp Trp Asn Val Val Asn Trp Ala Glu
            180                 185                 190

Ala Glu Lys Arg Phe Leu Glu Gly Lys Lys Lys Ala Gln Leu
        195                 200                 205
```

(2) INFORMATION FOR SEQ ID NO:7:

(i) SEQUENCE CHARACTERISTICS:
        (A) LENGTH: 812 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 2..673

(xi) SEQUENCE DESCRIPTION: SEQ ID NO:7:

```
G ATG TTC ACG CTT GCT ACG CGC CGC GCT GCT GCC GCC CCC CTC GCG           46
  Met Phe Thr Leu Ala Thr Arg Arg Ala Ala Ala Ala Pro Leu Ala
  1               5                  10                  15

AAC GCC GCC CAG ATG GGT GTG CGC ACC AAG TAC ACG CTG CCG CCG CTG         94
Asn Ala Ala Gln Met Gly Val Arg Thr Lys Tyr Thr Leu Pro Pro Leu
                20                  25                  30

CCG TAC GAC TAC GGC GCG CTC GAG CCG GCG ATC TCG GGC GAG ATC ATG        142
Pro Tyr Asp Tyr Gly Ala Leu Glu Pro Ala Ile Ser Gly Glu Ile Met
            35                  40                  45

GAG ACG CAC TAC GAG AAG CAC CAC CGC ACC TAC GTC AAC AAC CTG AAC        190
Glu Thr His Tyr Glu Lys His His Arg Thr Tyr Val Asn Asn Leu Asn
        50                  55                  60

GCC GCG GAG GAC AAG CTG ATC GAC GCG CTC CCG CAG CAG AGC CCG CTC        238
Ala Ala Glu Asp Lys Leu Ile Asp Ala Leu Pro Gln Gln Ser Pro Leu
    65                  70                  75

GGC GAG ATT GCG CAG CTG AAC GCG ATC AAG TTC AAC GGC GGT GGC CAC        286
Gly Glu Ile Ala Gln Leu Asn Ala Ile Lys Phe Asn Gly Gly Gly His
80                  85                  90                  95

ATC AAC CAC TCG CTC TTC TGG AAG AAC CTC GCG CCG ACG AAC AAG GGC        334
Ile Asn His Ser Leu Phe Trp Lys Asn Leu Ala Pro Thr Asn Lys Gly
                100                 105                 110

GGC GGC GAG CTC GAC TCG GGC GAG CTG CGC TCC GCG ATC GAC CGC GAC        382
Gly Gly Glu Leu Asp Ser Gly Glu Leu Arg Ser Ala Ile Asp Arg Asp
            115                 120                 125

TTT GGC TCG GTC GAC GCC ATG AAG GAG AAG TTC AAC GCG GCG CTC GCG        430
Phe Gly Ser Val Asp Ala Met Lys Glu Lys Phe Asn Ala Ala Leu Ala
        130                 135                 140

GGC ATC CAG GGC AGC GGC TGG GGC TGG CTC GGC CTG AAC CCC ACG ACG        478
Gly Ile Gln Gly Ser Gly Trp Gly Trp Leu Gly Leu Asn Pro Thr Thr
    145                 150                 155

CAG AAG CTC GAC ATC ATC ACG ACC GCG AAC CAG GAC CCG CTC CTG TCG        526
Gln Lys Leu Asp Ile Ile Thr Thr Ala Asn Gln Asp Pro Leu Leu Ser
160                 165                 170                 175

CAC AAG CCG CTG ATT GGC ATC GAT GCG TGG GAG CAC GCG TTC TAC CTG        574
His Lys Pro Leu Ile Gly Ile Asp Ala Trp Glu His Ala Phe Tyr Leu
                180                 185                 190

CAG TAC AAG AAC GTC AAG GCC GAC TAC TTC AAG GCG ATC TGG ACC GTG        622
Gln Tyr Lys Asn Val Lys Ala Asp Tyr Phe Lys Ala Ile Trp Thr Val
            195                 200                 205

ATC AAC TTT GAG GAG GCC GAG AAG CGT CTC AAG GAG GCG CTC GCC AAG        670
Ile Asn Phe Glu Glu Ala Glu Lys Arg Leu Lys Glu Ala Leu Ala Lys
        210                 215                 220

AAC TAGACACGTT CGGTTTTTTT TTTCTCCGTA GCTTCGCAAT GACCTGCCCA             723
Asn

CGCTAAAAAA AAAAAAAAAA AAAAAAAAAA AAAAAAAAAA AAAAAAAAAA AAAAAAAAAA      783

AAAAAAAAAA AAAAAAAAAA AAAAAAAA                                         812
```

(2) INFORMATION FOR SEQ ID NO:8:

(i) SEQUENCE CHARACTERISTICS:
        (A) LENGTH: 224 amino acids
        (B) TYPE: amino acid
        (D) TOPOLOGY: linear (ii) MOLECULE TYPE: protein (xi) SEQUENCE DESCRIPTION: SEQ ID NO:8:

```
Met Phe Thr Leu Ala Thr Arg Arg Ala Ala Ala Ala Pro Leu Ala Asn
  1               5                  10                  15

Ala Ala Gln Met Gly Val Arg Thr Lys Tyr Thr Leu Pro Pro Leu Pro
             20                  25                  30

Tyr Asp Tyr Gly Ala Leu Glu Pro Ala Ile Ser Gly Glu Ile Met Glu
         35                  40                  45

Thr His Tyr Glu Lys His His Arg Thr Tyr Val Asn Asn Leu Asn Ala
     50                  55                  60

Ala Glu Asp Lys Leu Ile Asp Ala Leu Pro Gln Gln Ser Pro Leu Gly
 65                  70                  75                  80

Glu Ile Ala Gln Leu Asn Ala Ile Lys Phe Asn Gly Gly His Ile
                 85                  90                  95

Asn His Ser Leu Phe Trp Lys Asn Leu Ala Pro Thr Asn Lys Gly Gly
                100                 105                 110

Gly Glu Leu Asp Ser Gly Glu Leu Arg Ser Ala Ile Asp Arg Asp Phe
            115                 120                 125

Gly Ser Val Asp Ala Met Lys Glu Lys Phe Asn Ala Ala Leu Ala Gly
        130                 135                 140

Ile Gln Gly Ser Gly Trp Gly Trp Leu Gly Leu Asn Pro Thr Thr Gln
145                 150                 155                 160

Lys Leu Asp Ile Ile Thr Thr Ala Asn Gln Asp Pro Leu Leu Ser His
                165                 170                 175

Lys Pro Leu Ile Gly Ile Asp Ala Trp Glu His Ala Phe Tyr Leu Gln
            180                 185                 190

Tyr Lys Asn Val Lys Ala Asp Tyr Phe Lys Ala Ile Trp Thr Val Ile
        195                 200                 205

Asn Phe Glu Glu Ala Glu Lys Arg Leu Lys Glu Ala Leu Ala Lys Asn
210                 215                 220
```

(2) INFORMATION FOR SEQ ID NO:9:

(i) SEQUENCE CHARACTERISTICS:
        (A) LENGTH: 1607 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 2..1522

(xi) SEQUENCE DESCRIPTION: SEQ ID NO:9:

```
G TTG AGC TCT GTG CTG AAG CGC TCG CCG CAG CTC TCT ACT AAG GCT        46
  Leu Ser Ser Val Leu Lys Arg Ser Pro Gln Leu Ser Thr Lys Ala
    1               5                  10                  15

CTG AAG CAG CCG CTT ACG CTC CCG CGT CTG CTC CCC ATT GGC GCT ACG      94
Leu Lys Gln Pro Leu Thr Leu Pro Arg Leu Leu Pro Ile Gly Ala Thr
             20                  25                  30
```

```
CCG CTG GCT CGT GGC TAC GCC TCG AGC TCG GAG CCG TAC GAT GTC ATT      142
Pro Leu Ala Arg Gly Tyr Ala Ser Ser Ser Glu Pro Tyr Asp Val Ile
             35                  40                  45

GTG ATC GGC GGT GGC CCC GGT GGC TAC GTG GCC GCC ATC AAG GCC GCA      190
Val Ile Gly Gly Gly Pro Gly Gly Tyr Val Ala Ala Ile Lys Ala Ala
         50                  55                  60

CAG GGT GGT CTG AAG ACT GCG TGT GTT GAG AAG CGT GGT GCC CTT GGC      238
Gln Gly Gly Leu Lys Thr Ala Cys Val Glu Lys Arg Gly Ala Leu Gly
     65                  70                  75

GGT ACG TGC TTG AAC GTG GGC TGT ATC CCG TCC AAG TCG TTG CTC AAC      286
Gly Thr Cys Leu Asn Val Gly Cys Ile Pro Ser Lys Ser Leu Leu Asn
 80                  85                  90                  95

AAC TCG CAC ATC TAC CAC CAG ACG CAG CAT GAC CTC AAG AAC CGC GGT      334
Asn Ser His Ile Tyr His Gln Thr Gln His Asp Leu Lys Asn Arg Gly
                100                 105                 110

ATT GAC GTC GGC GAC ATT AAG CTG AAC CTG CCG CAG ATG CTC AAG GCG      382
Ile Asp Val Gly Asp Ile Lys Leu Asn Leu Pro Gln Met Leu Lys Ala
            115                 120                 125

AAG GAG AGC TCG GTT ACT GCA CTC ACC AAG GGT GTC GAG GGT CTG TTC      430
Lys Glu Ser Ser Val Thr Ala Leu Thr Lys Gly Val Glu Gly Leu Phe
        130                 135                 140

AAG AAG AAC AAG GTC GAC TAC ATC AAG GGC ACT GCC AGC TTT GCC AGC      478
Lys Lys Asn Lys Val Asp Tyr Ile Lys Gly Thr Ala Ser Phe Ala Ser
    145                 150                 155

CCC ACG ACG GTG GAC GTG AAG CTG AAC GAT GGT GGT GAG CAG CAG ATC      526
Pro Thr Thr Val Asp Val Lys Leu Asn Asp Gly Gly Glu Gln Gln Ile
160                 165                 170                 175

GAG GGC AAG AAC ATC ATC ATT GCA ACC GGC TCT GAG GTG ACG CCC TTC      574
Glu Gly Lys Asn Ile Ile Ile Ala Thr Gly Ser Glu Val Thr Pro Phe
                180                 185                 190

CCG GGT GTT GAA ATC GAC GAG GAG CAG ATC ATC AGC TCG ACG GGT GCG      622
Pro Gly Val Glu Ile Asp Glu Glu Gln Ile Ile Ser Ser Thr Gly Ala
            195                 200                 205

CTC TCG CTC AAG GAG GTG CCC GAG AAG ATG GTC GTG ATC GGT GGT GGT      670
Leu Ser Leu Lys Glu Val Pro Glu Lys Met Val Val Ile Gly Gly Gly
        210                 215                 220

GTG ATC GGT CTT GAG CTT GGC AGC GTG TGG ACC CGT CTG GGT GCC AAG      718
Val Ile Gly Leu Glu Leu Gly Ser Val Trp Thr Arg Leu Gly Ala Lys
    225                 230                 235

GTG ACC GTG GTC GAG TTC CAG GAG GCG ATC GGT GGT CCC GGT CTG GAC      766
Val Thr Val Val Glu Phe Gln Glu Ala Ile Gly Gly Pro Gly Leu Asp
240                 245                 250                 255

AGC GAG GTG AGC CAA CAG TTC AAG AAG CTG CTC GAG AAG CAG GGC ATC      814
Ser Glu Val Ser Gln Gln Phe Lys Lys Leu Leu Glu Lys Gln Gly Ile
                260                 265                 270

CAC TTC AAG CTC GGC ACC AAG GTC AAC GGC ATT GAG AAG GAG AAC GGC      862
His Phe Lys Leu Gly Thr Lys Val Asn Gly Ile Glu Lys Glu Asn Gly
            275                 280                 285

AAG GTG ACT GTC CGC ACT GAG GGT AAG GAT GGC AAG GAG CAG GAC TAC      910
Lys Val Thr Val Arg Thr Glu Gly Lys Asp Gly Lys Glu Gln Asp Tyr
        290                 295                 300

GAT GCC AAT GTT GTG CTC GTG TCC ATT GGC CGT CGC CCG GTG ACC AAG      958
Asp Ala Asn Val Val Leu Val Ser Ile Gly Arg Arg Pro Val Thr Lys
    305                 310                 315

GGC CTC AAC CTC GAG GCG ATC GGG GTC GAG CTC GAC AAG AAG GGC CGC     1006
Gly Leu Asn Leu Glu Ala Ile Gly Val Glu Leu Asp Lys Lys Gly Arg
320                 325                 330                 335

GTG GTG GTG GAC GAC GAG TTC AAC ACG ACG TGC AAG GGT GTC AAG TGC     1054
Val Val Val Asp Asp Glu Phe Asn Thr Thr Cys Lys Gly Val Lys Cys
                340                 345                 350
```

```
ATT GGT GAC GCG ACG TTC GGC CCC ATG CTT GCG CAC AAG GCC GAG GAC      1102
Ile Gly Asp Ala Thr Phe Gly Pro Met Leu Ala His Lys Ala Glu Asp
            355                 360                 365

GAG GGT ATT GCC GTC GCC GAG ATG CTT GCG ACC GGT TAT GGC CAC GTC      1150
Glu Gly Ile Ala Val Ala Glu Met Leu Ala Thr Gly Tyr Gly His Val
        370                 375                 380

AAC TAC GAC GTG ATC CCT GCG GTG ATC TAC ACG CAC CCT GAG ATC GCG      1198
Asn Tyr Asp Val Ile Pro Ala Val Ile Tyr Thr His Pro Glu Ile Ala
385                 390                 395

TGG GTC GGC AAG TCG GAG CAG GAG CTC AAG AAC GAG GGC GTC CAG TAC      1246
Trp Val Gly Lys Ser Glu Gln Glu Leu Lys Asn Glu Gly Val Gln Tyr
400                 405                 410                 415

AAG GTG GGC AAG TTC CCC TTC CTG GCC AAC TCG CGT GCC AAG ACC AAC      1294
Lys Val Gly Lys Phe Pro Phe Leu Ala Asn Ser Arg Ala Lys Thr Asn
                420                 425                 430

GTC GAC ACC GAC GGC TTC GTC AAG TTC CTC GTG GAG AAG GAG ACC GAC      1342
Val Asp Thr Asp Gly Phe Val Lys Phe Leu Val Glu Lys Glu Thr Asp
            435                 440                 445

AAG ATT CTC GGC GTG TTC ATT ATC GGC CCG AAC GCT GGC GAG ATG ATC      1390
Lys Ile Leu Gly Val Phe Ile Ile Gly Pro Asn Ala Gly Glu Met Ile
        450                 455                 460

GCC GAG GCT GGC CTG GCT ATG GAG TAC GGC GCG AGT GCT GAG GAT GTT      1438
Ala Glu Ala Gly Leu Ala Met Glu Tyr Gly Ala Ser Ala Glu Asp Val
465                 470                 475

GCG CGC ACC TGC CAC GCG CAC CCG ACG CTC TCC GAG GCG TTC AAG GAG      1486
Ala Arg Thr Cys His Ala His Pro Thr Leu Ser Glu Ala Phe Lys Glu
480                 485                 490                 495

GGT GCG ATG GCC GCC TAC TCG AAG CCC ATC CAC TTT TGATTTCGTA           1532
Gly Ala Met Ala Ala Tyr Ser Lys Pro Ile His Phe
                500                 505

GGCTACCCCC GATAGGCGCC CGATACGTTT TCTCTCCAAA AAAAAAAAAA AAAAAAAAAA    1592

AAAAAAAAAA AAAAA                                                     1607

(2) INFORMATION FOR SEQ ID NO:10:

(i) SEQUENCE CHARACTERISTICS:
        (A) LENGTH: 507 amino acids
        (B) TYPE: amino acid
        (D) TOPOLOGY: linear (ii) MOLECULE TYPE: protein (xi) SEQUENCE DESCRIPTION: SEQ ID NO:10:

Leu Ser Ser Val Leu Lys Arg Ser Pro Gln Leu Ser Thr Lys Ala Leu
 1               5                  10                  15

Lys Gln Pro Leu Thr Leu Pro Arg Leu Leu Pro Ile Gly Ala Thr Pro
            20                  25                  30

Leu Ala Arg Gly Tyr Ala Ser Ser Glu Pro Tyr Asp Val Ile Val
        35                  40                  45

Ile Gly Gly Gly Pro Gly Gly Tyr Val Ala Ala Ile Lys Ala Ala Gln
 50                  55                  60

Gly Gly Leu Lys Thr Ala Cys Val Glu Arg Gly Ala Leu Gly Gly
 65                  70                  75                  80

Thr Cys Leu Asn Val Gly Cys Ile Pro Ser Lys Ser Leu Leu Asn Asn
                85                  90                  95

Ser His Ile Tyr His Gln Thr Gln His Asp Leu Lys Asn Arg Gly Ile
            100                 105                 110

Asp Val Gly Asp Ile Lys Leu Asn Leu Pro Gln Met Leu Lys Ala Lys
        115                 120                 125
```

```
Glu Ser Ser Val Thr Ala Leu Thr Lys Gly Val Glu Gly Leu Phe Lys
    130                 135                 140

Lys Asn Lys Val Asp Tyr Ile Lys Gly Thr Ala Ser Phe Ala Ser Pro
145                 150                 155                 160

Thr Thr Val Asp Val Lys Leu Asn Asp Gly Glu Gln Gln Ile Glu
                165                 170                 175

Gly Lys Asn Ile Ile Ile Ala Thr Gly Ser Glu Val Thr Pro Phe Pro
            180                 185                 190

Gly Val Glu Ile Asp Glu Glu Gln Ile Ile Ser Ser Thr Gly Ala Leu
        195                 200                 205

Ser Leu Lys Glu Val Pro Glu Lys Met Val Val Ile Gly Gly Val
    210                 215                 220

Ile Gly Leu Glu Leu Gly Ser Val Trp Thr Arg Leu Gly Ala Lys Val
225                 230                 235                 240

Thr Val Val Glu Phe Gln Glu Ala Ile Gly Gly Pro Gly Leu Asp Ser
                245                 250                 255

Glu Val Ser Gln Gln Phe Lys Lys Leu Leu Glu Lys Gln Gly Ile His
            260                 265                 270

Phe Lys Leu Gly Thr Lys Val Asn Gly Ile Glu Lys Glu Asn Gly Lys
        275                 280                 285

Val Thr Val Arg Thr Glu Gly Lys Asp Gly Lys Glu Gln Asp Tyr Asp
    290                 295                 300

Ala Asn Val Val Leu Val Ser Ile Gly Arg Arg Pro Val Thr Lys Gly
305                 310                 315                 320

Leu Asn Leu Glu Ala Ile Gly Val Glu Leu Asp Lys Lys Gly Arg Val
                325                 330                 335

Val Val Asp Asp Glu Phe Asn Thr Thr Cys Lys Gly Val Lys Cys Ile
            340                 345                 350

Gly Asp Ala Thr Phe Gly Pro Met Leu Ala His Lys Ala Glu Asp Glu
        355                 360                 365

Gly Ile Ala Val Ala Glu Met Leu Ala Thr Gly Tyr Gly His Val Asn
    370                 375                 380

Tyr Asp Val Ile Pro Ala Val Ile Tyr Thr His Pro Glu Ile Ala Trp
385                 390                 395                 400

Val Gly Lys Ser Glu Gln Glu Leu Lys Asn Glu Gly Val Gln Tyr Lys
                405                 410                 415

Val Gly Lys Phe Pro Phe Leu Ala Asn Ser Arg Ala Lys Thr Asn Val
            420                 425                 430

Asp Thr Asp Gly Phe Val Lys Phe Leu Val Glu Lys Glu Thr Asp Lys
        435                 440                 445

Ile Leu Gly Val Phe Ile Ile Gly Pro Asn Ala Gly Glu Met Ile Ala
    450                 455                 460

Glu Ala Gly Leu Ala Met Glu Tyr Gly Ala Ser Ala Glu Asp Val Ala
465                 470                 475                 480

Arg Thr Cys His Ala His Pro Thr Leu Ser Glu Ala Phe Lys Glu Gly
                485                 490                 495

Ala Met Ala Ala Tyr Ser Lys Pro Ile His Phe
            500                 505
```

(2) INFORMATION FOR SEQ ID NO:11:

(i) SEQUENCE CHARACTERISTICS:
        (A) LENGTH: 940 base pairs
        (B) TYPE: nucleic acid

```
            (C) STRANDEDNESS: double
            (D) TOPOLOGY: linear (ii) MOLECULE TYPE: cDNA to mRNA (ix) FEATURE:
            (A) NAME/KEY: CDS
            (B) LOCATION: 3..821

(xi) SEQUENCE DESCRIPTION: SEQ ID NO:11:

CG GAT CTC TCG CAC ATC AAC ACC CCC GCG GTG ACT TCG GGC TAC GCC          47
   Asp Leu Ser His Ile Asn Thr Pro Ala Val Thr Ser Gly Tyr Ala
    1               5                  10                  15

CAG GAC GAC CTC GAG GGT GCC GTC GAC GGT GCG GAG ATT GTG CTG ATC         95
Gln Asp Asp Leu Glu Gly Ala Val Asp Gly Ala Glu Ile Val Leu Ile
                 20                  25                  30

CCC GCC GGT ATG CCG CGC AAG CCC GGC ATG ACC CGT GAC GAC CTG TTC        143
Pro Ala Gly Met Pro Arg Lys Pro Gly Met Thr Arg Asp Asp Leu Phe
             35                  40                  45

AAC TCG AAC GCC TCG ATT GTC CGT GAC CTC GCC AAG GTC GTG GCT AAG        191
Asn Ser Asn Ala Ser Ile Val Arg Asp Leu Ala Lys Val Val Ala Lys
         50                  55                  60

GTC GCC CCA AAG GCT TAC ATC GGC GTC ATC TCG AAC CCC GTC AAC TCG        239
Val Ala Pro Lys Ala Tyr Ile Gly Val Ile Ser Asn Pro Val Asn Ser
     65                  70                  75

ACG GTG CCG ATC GTC GCT GAG GTG TTC AAG AAG GCC GGT GTG TAC GAC        287
Thr Val Pro Ile Val Ala Glu Val Phe Lys Lys Ala Gly Val Tyr Asp
 80                  85                  90                  95

CCC AAG CGC CTC TTC GGT GTG ACC ACG CTC GAC ACC ACG CGC GCG GCC        335
Pro Lys Arg Leu Phe Gly Val Thr Thr Leu Asp Thr Thr Arg Ala Ala
                100                 105                 110

ACC TTC CTG TCG GGC ATT GCT GGC TCG GAC CCG CAG ACC ACC AAC GTC        383
Thr Phe Leu Ser Gly Ile Ala Gly Ser Asp Pro Gln Thr Thr Asn Val
            115                 120                 125

CCC GTC ATT GGT GGC CAC TCG GGT GTG ACC ATT GTG CCC CTG ATC TCG        431
Pro Val Ile Gly Gly His Ser Gly Val Thr Ile Val Pro Leu Ile Ser
        130                 135                 140

CAG GCC GCC CAG GGT GAC AAG GTG CAG GCT GGC GAG CAG TAC GAC AAG        479
Gln Ala Ala Gln Gly Asp Lys Val Gln Ala Gly Glu Gln Tyr Asp Lys
    145                 150                 155

CTT GTG CAC CGC ATC CAG TTC GGT GGT GAC GAG GTC GTC AAG GCC AAG        527
Leu Val His Arg Ile Gln Phe Gly Gly Asp Glu Val Val Lys Ala Lys
160                 165                 170                 175

GAC GGT GCC GGC TCG GCG ACG CTC TCG ATG GCC TAC GCC GCC GCT GTC        575
Asp Gly Ala Gly Ser Ala Thr Leu Ser Met Ala Tyr Ala Ala Ala Val
                180                 185                 190

TTC ACC GAG GGC CTG CTC AAG GGT CTC GAC GGT GAG GCG GTG ACG CAG        623
Phe Thr Glu Gly Leu Leu Lys Gly Leu Asp Gly Glu Ala Val Thr Gln
            195                 200                 205

TGC ACC TTC GTC GAG AGC CCC CTG TTC AAG GAC CAG GTC GAC TTC TTC        671
Cys Thr Phe Val Glu Ser Pro Leu Phe Lys Asp Gln Val Asp Phe Phe
        210                 215                 220

GCC TCG CCC GTC GAG TTC GGC CCC GAG GGT GTG AAG AAC ATC CCT GCT        719
Ala Ser Pro Val Glu Phe Gly Pro Glu Gly Val Lys Asn Ile Pro Ala
    225                 230                 235

CTG CCG AAG CTC ACC GCC GAG GAG CAG AAG CTG CTC GAC GCC TGC CTG        767
Leu Pro Lys Leu Thr Ala Glu Glu Gln Lys Leu Leu Asp Ala Cys Leu
240                 245                 250                 255

CCC GAC CTT GCC AAG AAC ATC AAG AAG GGC GTT GCG TGG GCC GCC GAG        815
Pro Asp Leu Ala Lys Asn Ile Lys Lys Gly Val Ala Trp Ala Ala Glu
                260                 265                 270
```

```
AAC CCG TAAATGCGCA AAGCAATCTT TTACGGAGCT TGCGCGAAGG AAAGGAAATG     871
Asn Pro

TACGTTTCTA TAGAACGTAG ATCTGTCCCT TTCCACCTAA AAAAAAAAAA AAAAAAAAAA  931

AAAAAAAAA                                                          940
```

(2) INFORMATION FOR SEQ ID NO:12:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:12:

```
Asp Leu Ser His Ile Asn Thr Pro Ala Val Thr Ser Gly Tyr Ala Gln
 1               5                  10                  15

Asp Asp Leu Glu Gly Ala Val Asp Gly Ala Glu Ile Val Leu Ile Pro
                20                  25                  30

Ala Gly Met Pro Arg Lys Pro Gly Met Thr Arg Asp Asp Leu Phe Asn
            35                  40                  45

Ser Asn Ala Ser Ile Val Arg Asp Leu Ala Lys Val Val Ala Lys Val
        50                  55                  60

Ala Pro Lys Ala Tyr Ile Gly Val Ile Ser Asn Pro Val Asn Ser Thr
65                  70                  75                  80

Val Pro Ile Val Ala Glu Val Phe Lys Lys Ala Gly Val Tyr Asp Pro
                85                  90                  95

Lys Arg Leu Phe Gly Val Thr Thr Leu Asp Thr Thr Arg Ala Ala Thr
               100                 105                 110

Phe Leu Ser Gly Ile Ala Gly Ser Asp Pro Gln Thr Thr Asn Val Pro
               115                 120                 125

Val Ile Gly Gly His Ser Gly Val Thr Ile Val Pro Leu Ile Ser Gln
           130                 135                 140

Ala Ala Gln Gly Asp Lys Val Gln Ala Gly Glu Gln Tyr Asp Lys Leu
145                 150                 155                 160

Val His Arg Ile Gln Phe Gly Gly Asp Glu Val Val Lys Ala Lys Asp
                165                 170                 175

Gly Ala Gly Ser Ala Thr Leu Ser Met Ala Tyr Ala Ala Ala Val Phe
                180                 185                 190

Thr Glu Gly Leu Leu Lys Gly Leu Asp Gly Glu Ala Val Thr Gln Cys
            195                 200                 205

Thr Phe Val Glu Ser Pro Leu Phe Lys Asp Gln Val Asp Phe Phe Ala
210                 215                 220

Ser Pro Val Glu Phe Gly Pro Glu Gly Val Lys Asn Ile Pro Ala Leu
225                 230                 235                 240

Pro Lys Leu Thr Ala Glu Glu Gln Lys Leu Leu Asp Ala Cys Leu Pro
                245                 250                 255

Asp Leu Ala Lys Asn Ile Lys Lys Gly Val Ala Trp Ala Ala Glu Asn
            260                 265                 270

Pro
```

(2) INFORMATION FOR SEQ ID NO:13:

(i) SEQUENCE CHARACTERISTICS:
        (A) LENGTH: 306 base pairs
        (B) TYPE: nucleic acid

```
            (C) STRANDEDNESS: double
            (D) TOPOLOGY: linear (ii) MOLECULE TYPE: cDNA to mRNA (ix) FEATURE:
            (A) NAME/KEY: CDS
            (B) LOCATION: 1..306

(xi) SEQUENCE DESCRIPTION: SEQ ID NO:13:

GAA GTG GTG TAC AAG CCG GAC TCG CAG TCC ACG GAC GAG TTC ATC GTC        48
Glu Val Val Tyr Lys Pro Asp Ser Gln Ser Thr Asp Glu Phe Ile Val
 1               5                  10                  15

ATC GTC AAC CCC GAC TCG TAC CAG TCG TGG CGC TCG GGC AAC CGC ACC        96
Ile Val Asn Pro Asp Ser Tyr Gln Ser Trp Arg Ser Gly Asn Arg Thr
             20                  25                  30

ATC CCG CTC GCG GAT GTC GTC GAC TCC TTC CAC ATC TAC CAC TCG GGC       144
Ile Pro Leu Ala Asp Val Val Asp Ser Phe His Ile Tyr His Ser Gly
         35                  40                  45

CAG GGC AGC CAG GGC ATC CTC GGC CAG GTG TCG AAG CAG CAG CTC GAC       192
Gln Gly Ser Gln Gly Ile Leu Gly Gln Val Ser Lys Gln Gln Leu Asp
 50                  55                  60

TCC GTG TTC GGT ACC GCG AAG GAG GAC GAG GCG GTG ATC CTC ATC CTC       240
Ser Val Phe Gly Thr Ala Lys Glu Asp Glu Ala Val Ile Leu Ile Leu
 65                  70                  75                  80

GAG CGC GGC CAC CTC CAG CAC GGC AAA ATG CGT GGC CAC GAC AAG TCG       288
Glu Arg Gly His Leu Gln His Gly Lys Met Arg Gly His Asp Lys Ser
                 85                  90                  95

GGC CGC AAC AGC TCG CGC                                                306
Gly Arg Asn Ser Ser Arg
                100

(2) INFORMATION FOR SEQ ID NO:14:

(i) SEQUENCE CHARACTERISTICS:
            (A) LENGTH: 102 amino acids
            (B) TYPE: amino acid
            (D) TOPOLOGY: linear (ii) MOLECULE TYPE: protein (xi) SEQUENCE DESCRIPTION: SEQ ID NO:14:

Glu Val Val Tyr Lys Pro Asp Ser Gln Ser Thr Asp Glu Phe Ile Val
 1               5                  10                  15

Ile Val Asn Pro Asp Ser Tyr Gln Ser Trp Arg Ser Gly Asn Arg Thr
             20                  25                  30

Ile Pro Leu Ala Asp Val Val Asp Ser Phe His Ile Tyr His Ser Gly
         35                  40                  45

Gln Gly Ser Gln Gly Ile Leu Gly Gln Val Ser Lys Gln Gln Leu Asp
 50                  55                  60

Ser Val Phe Gly Thr Ala Lys Glu Asp Glu Ala Val Ile Leu Ile Leu
 65                  70                  75                  80

Glu Arg Gly His Leu Gln His Gly Lys Met Arg Gly His Asp Lys Ser
                 85                  90                  95

Gly Arg Asn Ser Ser Arg
                100

(2) INFORMATION FOR SEQ ID NO:15:

(i) SEQUENCE CHARACTERISTICS:
            (A) LENGTH: 23 base pairs
            (B) TYPE: nucleic acid
```

(C) STRANDEDNESS: single
            (D) TOPOLOGY: linear (ii) MOLECULE TYPE: other nucleic acid
            (A) DESCRIPTION: /desc = "Synthetic DNA"

(xi) SEQUENCE DESCRIPTION: SEQ ID NO:15:

CCNGGNGAYC CNACNGCNAC NGC                                              23

(2) INFORMATION FOR SEQ ID NO:16:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic DNA"

(xi) SEQUENCE DESCRIPTION: SEQ ID NO:16:

ACNYTNATGG GNTAYATHCC NTGGAC                                           26

(2) INFORMATION FOR SEQ ID NO:17:

(i) SEQUENCE CHARACTERISTICS:
            (A) LENGTH: 599 base pairs
            (B) TYPE: nucleic acid
            (C) STRANDEDNESS: double
            (D) TOPOLOGY: linear (ii) MOLECULE TYPE: cDNA to mRNA (xi) SEQUENCE DESCRIPTION: SEQ ID NO:17:

ACACTGATGG GATACATTCC CTGGACCCCG GAGCTCGACT CGGGTGAGGT GTGTGGTATC       60

CCCCACCACC TTCCAAGACC CGCGACGAGT GGAAGGGCAA GAAGGTTGTG ATTGTCTCGA     120

TCCCGGGTGC CTACACCCCC ATCTGTCCAC CAGCAGAACA TCCCCCCGCT TTGTGAAGCG     180

TGTGGATGAG CTCAAGGCCA AGGGTGTCCC GACGCCGTGT ACGTCATTGC GTCGAACGAC     240

CCCTTCGTCA TGGCTGCCTG GGGCCAACTT CAACAACGCC AAGGACAAGG TCGTCTTTGG     300

CACCGACATT GACCTGGCCT TCTCCCAAGG CTCTCGGCGC GACGATCCGA CCTGAGCGCC     360

AAGCACTTTG GTGAGCGCAC GGCCCGCTAC GCTCTGATCA TTGACGACAA CAAGATTGTC     420

GACTTTGGTT CGGACGAGGG CGACACTGGC AAGCTCCAGA ACGCGTCGAT CGACACGATC     480

CTCACCAAGG TCTTAAAATT GGCGCATGTG CGTTGTGGTG ACCACTACCT AAAGGGTCCG     540

TAGAGTTCCA AGTCAAGTCG TATATTTTTA ATTTAAAAAA AAAAAAAAAA AAAAAAAA      599

(2) INFORMATION FOR SEQ ID NO:18:

(i) SEQUENCE CHARACTERISTICS:
            (A) LENGTH: 991 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: CDS
            (B) LOCATION: 260..269

(ix) FEATURE:
            (A) NAME/KEY: intron
            (B) LOCATION: 269..305

(ix) FEATURE:
    (A) NAME/KEY: CDS
    (B) LOCATION: 306..590

(ix) FEATURE:
    (A) NAME/KEY: intron
    (B) LOCATION: 591..629

(ix) FEATURE:
    (A) NAME/KEY: CDS
    (B) LOCATION: 630..869

(xi) SEQUENCE DESCRIPTION: SEQ ID NO:18:

```
AGACAGCAGG GACATGGTTT AGAAGCACAA TTCGCGGTAG CTGGCGCTGA AGCGATACTC      60

GCTGAGAAAT TCACTTTCCC CCCGCTGACG GCCAGACCCC CGAACTGTCC CGAATTACCA     120

AGCAAATGCA CGTGACGTTT GTGGAGGCTC GGGGATTATC AGGCCACGTA TCAGTGAGCC     180

GAGCACCGCG TGGCTTCGGC TGGCTGCATA TAAAGCCGGG TGGGCCGTGC TCACAGCTTC     240

ATCTTCCACG ACAATCATT ATG CCT GGT G TAGGTACCGC GAAGTGACAC             289
                     Met Pro Gly
                      1

GCATGCTGAC CATCAG GAT CCT ACT GCT ACT GCC AAG GGT AAC GAG ATC         338
              Asp Pro Thr Ala Thr Ala Lys Gly Asn Glu Ile
               1               5                  10

CCC GAC ACC CTC ATG GGC TAC ATC CCC TGG ACC CCG GAG CTC GAC TCG       386
Pro Asp Thr Leu Met Gly Tyr Ile Pro Trp Thr Pro Glu Leu Asp Ser
             15                  20                  25

GGT GAG GTG TGT GGT ATC CCC ACC ACC TTC AAG ACC CGC GAC GAG TGG       434
Gly Glu Val Cys Gly Ile Pro Thr Thr Phe Lys Thr Arg Asp Glu Trp
         30                  35                  40

AAG GGC AAG AAG GTT GTG ATT GTC TCG ATC CCG GGT GCC TAC ACC CCC       482
Lys Gly Lys Lys Val Val Ile Val Ser Ile Pro Gly Ala Tyr Thr Pro
     45                  50                  55

ATC TGC CAC CAG CAG CAC ATC CCC CCG CTT GTG AAG CGT GTG GAT GAG       530
Ile Cys His Gln Gln His Ile Pro Pro Leu Val Lys Arg Val Asp Glu
 60                  65                  70                  75

CTC AAG GCC AAG GGT GTC GAC GCC GTG TAC GTC ATT GCG TCG AAC GAC       578
Leu Lys Ala Lys Gly Val Asp Ala Val Tyr Val Ile Ala Ser Asn Asp
             80                  85                  90

CCC TTC GTC ATG GGTATGTACT GCTCTGTCAT TTCTTTATGC TAACCGACA GCT        632
Pro Phe Val Met                                                  Ala
             95                                                   1

GCC TGG GGC AAC TTC AAC AAC GCC AAG GAC AAG GTC GTC TTT GCC ACC       680
Ala Trp Gly Asn Phe Asn Asn Ala Lys Asp Lys Val Val Phe Ala Thr
              5                  10                  15

GAC ATT GAC CTG GCC TTC TCC AAG GCT CTC GGC GCG ACG ATC GAC CTG       728
Asp Ile Asp Leu Ala Phe Ser Lys Ala Leu Gly Ala Thr Ile Asp Leu
             20                  25                  30

AGC GCC AAG CAC TTT GGT GAG CGC ACG GCC CGC TAC GCT CTG ATC ATT       776
Ser Ala Lys His Phe Gly Glu Arg Thr Ala Arg Tyr Ala Leu Ile Ile
         35                  40                  45

GAC GAC AAC AAG ATT GTC GAC TTT GCT TCG GAC GAG GGC GAC ACT GGC       824
Asp Asp Asn Lys Ile Val Asp Phe Ala Ser Asp Glu Gly Asp Thr Gly
 50                  55                  60                  65

AAG CTC CAG AAC GCG TCG ATC GAC ACG ATC CTC ACC AAG GTC TAA           869
Lys Leu Gln Asn Ala Ser Ile Asp Thr Ile Leu Thr Lys Val   *
             70                  75                  80

AATGGCGCAT GTGCGTTGTG TGACCACTAC CTAAAGGGTC CGTAGAGTTC CAAGTCAAGT     929

CGTATATTTT TTTTTTACAG GATGGTGTGT ACTGCCACCT GCCTTTGAGC AAGGCGTGCC     989

AG                                                                   991
```

(2) INFORMATION FOR SEQ ID NO:19:

(i) SEQUENCE CHARACTERISTICS:
        (A) LENGTH: 177 amino acids
        (B) TYPE: amino acid
        (D) TOPOLOGY: linear (ii) MOLECULE TYPE: peptide (xi) SEQUENCE DESCRIPTION: SEQ ID NO:19:

```
Met Pro Gly Asp Pro Thr Ala Thr Ala Lys Gly Asn Glu Ile Pro Asp
 1               5                  10                  15

Thr Leu Met Gly Tyr Ile Pro Trp Thr Pro Glu Leu Asp Ser Gly Glu
             20                  25                  30

Val Cys Gly Ile Pro Thr Thr Phe Lys Thr Arg Asp Glu Trp Lys Gly
         35                  40                  45

Lys Lys Val Val Ile Val Ser Ile Pro Gly Ala Tyr Thr Pro Ile Cys
     50                  55                  60

His Gln Gln His Ile Pro Pro Leu Val Lys Arg Val Asp Glu Leu Lys
 65                  70                  75                  80

Ala Lys Gly Val Asp Ala Val Tyr Val Ile Ala Ser Asn Asp Pro Phe
                 85                  90                  95

Val Met Ala Ala Trp Gly Asn Phe Asn Asn Ala Lys Asp Lys Val Val
            100                 105                 110

Phe Ala Thr Asp Ile Asp Leu Ala Phe Ser Lys Ala Leu Gly Ala Thr
        115                 120                 125

Ile Asp Leu Ser Ala Lys His Phe Gly Glu Arg Thr Ala Arg Tyr Ala
130                 135                 140

Leu Ile Ile Asp Asp Asn Lys Ile Val Asp Phe Ala Ser Asp Glu Gly
145                 150                 155                 160

Asp Thr Gly Lys Leu Gln Asn Ala Ser Ile Asp Thr Ile Leu Thr Lys
                165                 170                 175

Val *
```

(2) INFORMATION FOR SEQ ID NO:20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:20:

```
ACNTTYGCNC ARGAYGTNAA YTGYG                                  25
```

(2) INFORMATION FOR SEQ ID NO:21:

(i) SEQUENCE CHARACTERISTICS:
        (A) LENGTH: 261 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:21:

```
ACCTTTGCAC AGGACGTCAA TTGCGAGTTC TCCAAGCACT TTAACGCGAC GCTGGACCTG    60

TCGTCGAAGG GCATGGGCCT GCGCACCGCG CGCTACGCGC TGATCGCGAA CGACCTCAAG   120
```

```
GTCGAGTACT TTGGCATCGA CGAGGGCGAG CCGAAGCAGT CGTCGGCCGC GACGGTGCTG      180

AGCAAGCTGT AGTGCCGTTC TACTTAGTCA AACAATCGGG TATAGTCGCG TTGGAAAAAA      240

AAAAAAAAAA AAAAAAAAAA A                                                261
```

(2) INFORMATION FOR SEQ ID NO:22:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:22:

```
CARACNTAYG TNAAYAAYYT NAAYGC                                           26
```

(2) INFORMATION FOR SEQ ID NO:23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:23:

```
ACNCAYCAYC CNGTNATHGG NTGGG                                            25
```

(2) INFORMATION FOR SEQ ID NO:24:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:24:

```
ATNACNGGRT GRTGNGTNGT NARNGG                                           26
```

(2) INFORMATION FOR SEQ ID NO:25:

(i) SEQUENCE CHARACTERISTICS:
        (A) LENGTH: 371 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:25:

```
CAGACCTATG TCAACAACCT GAACGCCGCC GAGAAGGCGT ACGCTGAGGC GACGGCCGCG      60

AACGACGTGC TTAAGCAGAT CCAGCTGCAG AGTGCGATCA AGTTCAACGG CGGTGGCCAC      120

ATCAACCACT CGCTGTTCTG GAAGAACCTG GCCCCCAGA GCGAGGGTGG TGGCCAACTG       180

AACGATGGCC CTCTCAAGCA GGCCATCGAG CAGGAGTTCG GCGACTTTGA GAAATTCAAG      240

ACGACCTTCA ACACGAAGGC GGCCGGCATC CAGGGTTCGG GCTGGCTGTG GCTCGGTGTT      300
```

| | |
|---|---|
| GCCCCGACGG GCAACCTCGA CCTGGTCGTT GCCAAGGACC AGGACCCGCT GACCACCCAT | 360 |
| CACCCCGTGA T | 371 |

(2) INFORMATION FOR SEQ ID NO:26:

(i) SEQUENCE CHARACTERISTICS:
        (A) LENGTH: 263 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:26:

| | |
|---|---|
| ACGCATCATC CCGTGATTGG CTGGGATGGC TGGGAGCACG CCTGGTACCT GCAGTACAAG | 60 |
| NACGACAAGG CTTCCTACCT TAAGGCCTGG TGGAACGTGG TGAACTGGGC CGAGGCCGAG | 120 |
| AAGCGCTTCC TCGAGGGTAA GAAGAAGGCC CAGCTGTAAT GGCACGTTTG TAGATGATGA | 180 |
| ACGACACACG ATTTTAGGTC GCCAAAAAAA AAAAAAAAAA AAAAAAAAAA AAAAAAAAAA | 240 |
| AAAAAAAAAA AAAAAAAAA AAA | 263 |

(2) INFORMATION FOR SEQ ID NO:27:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:27:

| | |
|---|---|
| CCNCCNYTNC CNTAYGAYTA YGGNGC | 26 |

(2) INFORMATION FOR SEQ ID NO:28:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:28:

| | |
|---|---|
| GARCCNGCNA THWSNGGNGA RATHATGG | 28 |

(2) INFORMATION FOR SEQ ID NO:29:

(i) SEQUENCE CHARACTERISTICS:
        (A) LENGTH: 630 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:29:

| | |
|---|---|
| GAACCTGCTT TCTGGGGGA GATAATGGAG ACGCACTACG AGAAGCACCA CCGCACCTAC | 60 |
| GTCAACAACC TGAACGCCGC GGAGGACAAG CTGATCGACG CGCTCCCGCA GCAGAGCCCG | 120 |
| CTCGGCGAGA TTGCGCAGCT GAACGCGATC AANTTCATCG GCGGTGGCCA CATCAACCAC | 180 |
| TCGCTCTTCT GGAAGAACCT CGCGCCGACG AACAAGGGCG GCGGCGAGCT CGACTCGGGC | 240 |

```
GAGCTGCGCT CCGCGATCGA CCGCGACTTT GGCTCGGTCG ACGCCATGAA GGAGAAGTTC      300

AACGCGGCGC TCGCGGGCAT CCAGGGTATC GGCTGGGGCT GGCTCGGCCT GAACCCCACG      360

ACGCAGAAGC TCGACATCAT CACGACCGCG AACCAGGACC CGCTCCTGTC GCACAAGCCG      420

CTGATTGGCA TCGATGCGTG GGAGCACGCG TACTACCTGC AGTACAAGAA CGTCAAGGCC      480

GACTACTTCA AGGCGATCTG GACCGTGATC AACTTTGAGG AGGCCGAGAA GCGTCTCANG      540

GAGGCGCTCG CCAAGAACTA GACACGTTCG GTTTTTTTTT TATCACTAGC TTAGCAATGA      600

CCTGCCCACG CTAAAAAAAA AAAAAAAAAA                                       630
```

(2) INFORMATION FOR SEQ ID NO:30:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 15
        (D) OTHER INFORMATION: /mod_base= i (xi) SEQUENCE DESCRIPTION: SEQ ID NO:30:

```
GGNTAYGTNG CNGCNATHAA RGC                                               23
```

(2) INFORMATION FOR SEQ ID NO:31:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 15
        (D) OTHER INFORMATION: /mod_base= i (ix) FEATURE:
        (A) NAME/KEY: modified_base
        (B) LOCATION: 18
        (D) OTHER INFORMATION: /mod_base= i (xi) SEQUENCE DESCRIPTION: SEQ ID NO:31:

TCYTCNGCYT TRTGNGCNAR CAT                                              23

(2) INFORMATION FOR SEQ ID NO:32:

(i) SEQUENCE CHARACTERISTICS:
        (A) LENGTH: 938 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:32:

GGGTNCGTGG CGGCGATAAA GGCCGCGCAG GGTGGTCTGA AGACTGCATG TGTTGAGAAG        60

CGCGGTGCGC TTGGTGGTAC CTGCTTGAAC GTGGGCTGTA TCCCTTCCAA GTCGTTGGTG       120

AACAACTCGC ACATCTTCCA CCAGACGCAG CACGACCTCA AGAACCGCGG TATTGACGTC       180

AGCGAGGTCA AGTTGANCCT GCCGCAGATG CTCAAGGCGA AGGAGAGCTC GGTCACTGCG       240

CTCACCAAGG GTGTCGAGGG CCTGTTCAAG AAGAACAAGG TCGCCTACCT CAAGGGGACA       300

GACAGATTCG CGAGCCCTAC GACGGTGGAC GTGAAGCTGA GCGATGGCGG TGAACAGNAG       360

ATTGAGGGCA GAACATTAT CATTGCGACT GGCTCTGAGG TGACGCCTTN CCCTGGTGTG        420

GAGATCGCCG AGGAGCAGAT TATCAGCTCG ACGGGTGCGC TCTCGCTCAA GGAGGTGCCT       480

NAGAAGATGG TCGTGATCGG TGGTGGTGTG ANCGCTCTTG AGCTCGNTAG CGTGTGGAGC       540

CGTCTGGNCC CCAAGGTGAC CGTGGNTGAG TTCCAGGACG CGATTGTTGC CCCCGGTCTG       600

GACAGCGAGG TGACCCAGCA GTTCAAGAAG CTGCTCGAGA AGCAGGGCAT CCAGTTCAAG       660

CTTGCCACTA AGGTGAACGG GATTGAGAAG CAGGATGCCA AAGTGATGGT CCGCACCGAG       720

GGCAAGGACG GCAAGGAGCA GGACNACGAC GCCAACGTTG TGCTCGTGTC CATCGGTCNC       780

CNCCCGGTGA CGAAGGGCTT GAACCTCGAG GCGATCGGCG TTGAGCTTGA TAAGAAGGCC       840

CGCGTGGTGG TGGACGATGA GTTCAACACG ACGTGCAAGG GTGTCAAGTG CATTGGTGAC       900

GCGACGTTCG GCCCTATGCT CGCCCACAAG GCCGAAGA                              938

(2) INFORMATION FOR SEQ ID NO:33:

(i) SEQUENCE CHARACTERISTICS:
        (A) LENGTH: 1600 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 2..1523

(xi) SEQUENCE DESCRIPTION: SEQ ID NO:33:

```
G TTG AGC TCT GTG CTG AAG CGC TCG CCG CAG CTC TCT ACT AAG GCT        46
  Leu Ser Ser Val Leu Lys Arg Ser Pro Gln Leu Ser Thr Lys Ala
  1               5                   10                  15

CTG AAG CAG CCG CTT ACG CTC CCG CGT CTG CTG CCC ATT GGT GCT GCG     94
Leu Lys Gln Pro Leu Thr Leu Pro Arg Leu Leu Pro Ile Gly Ala Ala
                20                  25                  30

CCG CTG GCT CGT GGC TAT GCC TCG AGC TCG GAG CCA TAC GAT GTC ATT    142
Pro Leu Ala Arg Gly Tyr Ala Ser Ser Ser Glu Pro Tyr Asp Val Ile
            35                  40                  45
```

```
GTG ATT GGT GGT GGC CCC GGT GGC TAC GTG GCC GCG ATC AAG GCC GCG      190
Val Ile Gly Gly Gly Pro Gly Gly Tyr Val Ala Ala Ile Lys Ala Ala
         50                  55                  60

CAG GGT GGT CTG AAG ACT GCA TGT GTT GAG AAG CGC GGT GCG CTT GGT      238
Gln Gly Gly Leu Lys Thr Ala Cys Val Glu Lys Arg Gly Ala Leu Gly
 65                  70                  75

GGT ACC TGC TTG AAC GTG GGC TGT ATC CCT TCC AAG TCG TTG CTG AAC      286
Gly Thr Cys Leu Asn Val Gly Cys Ile Pro Ser Lys Ser Leu Leu Asn
 80                  85                  90                  95

AAC TCG CAC ATC TTC CAC CAG ACG CAG CAC GAC CTC AAG AAC CGC GGT      334
Asn Ser His Ile Phe His Gln Thr Gln His Asp Leu Lys Asn Arg Gly
                100                 105                 110

ATT GAC GTC AGC GAG GTC AAG TTG AAC CTG CCG CAG ATG CTC AAG GCG      382
Ile Asp Val Ser Glu Val Lys Leu Asn Leu Pro Gln Met Leu Lys Ala
            115                 120                 125

AAG GAG AGC TCG GTC ACT GCG CTC ACC AAG GGT GTC GAG GGC CTG TTC      430
Lys Glu Ser Ser Val Thr Ala Leu Thr Lys Gly Val Glu Gly Leu Phe
        130                 135                 140

AAG AAG AAC AAG GTC GAC TAC CTC AAG GGC ACA GCC AGC TTC GCG AGC      478
Lys Lys Asn Lys Val Asp Tyr Leu Lys Gly Thr Ala Ser Phe Ala Ser
145                 150                 155

CCT ACG ACG GTG GAC GTG AAG CTG AAC GAT GGC GGT GAA CAG CAG ATT      526
Pro Thr Thr Val Asp Val Lys Leu Asn Asp Gly Gly Glu Gln Gln Ile
160                 165                 170                 175

GAG GGC AAG AAC ATT ATC ATT GCG ACT GGC TCT GAG GTG ACG CCC TTC      574
Glu Gly Lys Asn Ile Ile Ile Ala Thr Gly Ser Glu Val Thr Pro Phe
                180                 185                 190

CCT GGT GTG GAG ATC GAC GAG GAG CAG ATT ATC AGC TCG ACG GGT GCG      622
Pro Gly Val Glu Ile Asp Glu Glu Gln Ile Ile Ser Ser Thr Gly Ala
            195                 200                 205

CTC TCG CTC AAG GAG GTG CCT GAG AAG ATG GTC GTG ATC GGT GGT GGT      670
Leu Ser Leu Lys Glu Val Pro Glu Lys Met Val Val Ile Gly Gly Gly
        210                 215                 220

GTG ATC GGT CTG GAG CTC GGT AGC GTG TGG AGC CGT CTG GGC GCC AAG      718
Val Ile Gly Leu Glu Leu Gly Ser Val Trp Ser Arg Leu Gly Ala Lys
        225                 230                 235

GTG ACC GTG GTT GAG TTC CAG GAC GCG ATT GGT GGC CCC GGT CTG GAC      766
Val Thr Val Val Glu Phe Gln Asp Ala Ile Gly Gly Pro Gly Leu Asp
240                 245                 250                 255

AGC GAG GTG AGC CAG CAG TTC AAG AAG CTG CTC GAG AAG CAG GGC ATC      814
Ser Glu Val Ser Gln Gln Phe Lys Lys Leu Leu Glu Lys Gln Gly Ile
                260                 265                 270

CAG TTC AAG CTT GGC ACT AAG GTG AAC GGG ATT GAG AAG CAG GAT GGC      862
Gln Phe Lys Leu Gly Thr Lys Val Asn Gly Ile Glu Lys Gln Asp Gly
            275                 280                 285

AAA GTG ATG GTC CGC ACC GAG GGC AAA GAC GGC AAG GAG CAG GAC TAC      910
Lys Val Met Val Arg Thr Glu Gly Lys Asp Gly Lys Glu Gln Asp Tyr
        290                 295                 300

GAC GCC AAC GTT GTG CTC GTG TCC ATC GGT CGC CGC CCG GTG ACG AAG      958
Asp Ala Asn Val Val Leu Val Ser Ile Gly Arg Arg Pro Val Thr Lys
305                 310                 315

GGC TTG AAC CTC GAG GCG ATC GGC GTT GAG CTT GAT AAG AAG GGC CGC     1006
Gly Leu Asn Leu Glu Ala Ile Gly Val Glu Leu Asp Lys Lys Gly Arg
                320                 325                 330                 335

GTG GTG GTG GAC GAT GAG TTC AAC ACG ACG TGC AAG GGT GTC AAG TGC     1054
Val Val Val Asp Asp Glu Phe Asn Thr Thr Cys Lys Gly Val Lys Cys
            340                 345                 350

ATT GGT GAC GCG ACG TTC GGC CCT ATG CTT GCG CAC AAG GCC GAG GAC     1102
Ile Gly Asp Ala Thr Phe Gly Pro Met Leu Ala His Lys Ala Glu Asp
        355                 360                 365
```

```
GAG GGT ATC GCC GTT GCT GAG ATG CTC GCG ACC GGC TAC GGC CAC GTC      1150
Glu Gly Ile Ala Val Ala Glu Met Leu Ala Thr Gly Tyr Gly His Val
        370                 375                 380

AAC TAC GAC GTG ATC CCT GCG GTG ATC TAC ACG CAC CCC GAG ATT GCG      1198
Asn Tyr Asp Val Ile Pro Ala Val Ile Tyr Thr His Pro Glu Ile Ala
385                 390                 395

TGG GTC GGC AAG TCG GAG CAG GAG CTC AAG AAC GAT GGC GTG CAG TAC      1246
Trp Val Gly Lys Ser Glu Gln Glu Leu Lys Asn Asp Gly Val Gln Tyr
400                 405                 410                 415

AAG GTG GGC AAG TTC CCC TTC CTG GCC AAC TCG CGT GCT AAG ACC AAC      1294
Lys Val Gly Lys Phe Pro Phe Leu Ala Asn Ser Arg Ala Lys Thr Asn
                420                 425                 430

GTC GAC ACC GAC GGT TTT GTC AAG TTC CTC GTG GAG AAG GAC ACC GAC      1342
Val Asp Thr Asp Gly Phe Val Lys Phe Leu Val Glu Lys Asp Thr Asp
                435                 440                 445

AAG ATT CTC GGC GTG TTC ATC ATC GGT CCG AAC GCC GGC GAG ATG ATT      1390
Lys Ile Leu Gly Val Phe Ile Ile Gly Pro Asn Ala Gly Glu Met Ile
            450                 455                 460

GCC GAG GCT GGC CTG GCT ATG GAG TAC GGT GCG AGT GCA GAG GAT GTC      1438
Ala Glu Ala Gly Leu Ala Met Glu Tyr Gly Ala Ser Ala Glu Asp Val
465                 470                 475

GCG CGC ACC TGC CAC GCG CAC CCG ACG CTC TCG GAG GCC TTC AAG GAG      1486
Ala Arg Thr Cys His Ala His Pro Thr Leu Ser Glu Ala Phe Lys Glu
480                 485                 490                 495

GGT GCG ATG GCC GCC TAC TCG AAG CCG ATT CAC TTT T GATTTCGTAG         1533
Gly Ala Met Ala Ala Tyr Ser Lys Pro Ile His Phe
                500                 505

GTTTCCCCCG ATAGGCGCCC GATACGTCTT CCTCAAAAAA AAAAAAAAAA AAAAAAAAA     1593

AAAAAAA                                                              1600

(2) INFORMATION FOR SEQ ID NO:34:

(i) SEQUENCE CHARACTERISTICS:
        (A) LENGTH: 507 amino acids
        (B) TYPE: amino acid
        (D) TOPOLOGY: linear (ii) MOLECULE TYPE: protein (xi) SEQUENCE DESCRIPTION: SEQ ID NO:34:

Leu Ser Ser Val Leu Lys Arg Ser Pro Gln Leu Ser Thr Lys Ala Leu
1               5                   10                  15

Lys Gln Pro Leu Thr Leu Pro Arg Leu Leu Pro Ile Gly Ala Ala Pro
                20                  25                  30

Leu Ala Arg Gly Tyr Ala Ser Ser Glu Pro Tyr Asp Val Ile Val
        35                  40                  45

Ile Gly Gly Gly Pro Gly Gly Tyr Val Ala Ala Ile Lys Ala Ala Gln
    50                  55                  60

Gly Gly Leu Lys Thr Ala Cys Val Glu Lys Arg Gly Ala Leu Gly Gly
65                  70                  75                  80

Thr Cys Leu Asn Val Gly Cys Ile Pro Ser Lys Ser Leu Leu Asn Asn
                85                  90                  95

Ser His Ile Phe His Gln Thr Gln His Asp Leu Lys Asn Arg Gly Ile
            100                 105                 110

Asp Val Ser Glu Val Lys Leu Asn Leu Pro Gln Met Leu Lys Ala Lys
            115                 120                 125

Glu Ser Ser Val Thr Ala Leu Thr Lys Gly Val Glu Gly Leu Phe Lys
            130                 135                 140
```

```
Lys Asn Lys Val Asp Tyr Leu Lys Gly Thr Ala Ser Phe Ala Ser Pro
145                 150                 155                 160

Thr Thr Val Asp Val Lys Leu Asn Asp Gly Glu Gln Gln Ile Glu
            165                 170                 175

Gly Lys Asn Ile Ile Ile Ala Thr Gly Ser Glu Val Thr Pro Phe Pro
                180                 185                 190

Gly Val Glu Ile Asp Glu Glu Gln Ile Ile Ser Ser Thr Gly Ala Leu
            195                 200                 205

Ser Leu Lys Glu Val Pro Glu Lys Met Val Val Ile Gly Gly Gly Val
            210                 215                 220

Ile Gly Leu Glu Leu Gly Ser Val Trp Ser Arg Leu Gly Ala Lys Val
225                 230                 235                 240

Thr Val Val Glu Phe Gln Asp Ala Ile Gly Pro Gly Leu Asp Ser
                245                 250                 255

Glu Val Ser Gln Gln Phe Lys Lys Leu Leu Glu Lys Gln Gly Ile Gln
            260                 265                 270

Phe Lys Leu Gly Thr Lys Val Asn Gly Ile Glu Lys Gln Asp Gly Lys
            275                 280                 285

Val Met Val Arg Thr Glu Gly Lys Asp Gly Lys Glu Gln Asp Tyr Asp
    290                 295                 300

Ala Asn Val Val Leu Val Ser Ile Gly Arg Arg Pro Val Thr Lys Gly
305                 310                 315                 320

Leu Asn Leu Glu Ala Ile Gly Val Glu Leu Asp Lys Lys Gly Arg Val
                325                 330                 335

Val Val Asp Asp Glu Phe Asn Thr Thr Cys Lys Gly Val Lys Cys Ile
                340                 345                 350

Gly Asp Ala Thr Phe Gly Pro Met Leu Ala His Lys Ala Glu Asp Glu
            355                 360                 365

Gly Ile Ala Val Ala Glu Met Leu Ala Thr Gly Tyr Gly His Val Asn
            370                 375                 380

Tyr Asp Val Ile Pro Ala Val Ile Tyr Thr His Pro Glu Ile Ala Trp
385                 390                 395                 400

Val Gly Lys Ser Glu Gln Glu Leu Lys Asn Asp Gly Val Gln Tyr Lys
                405                 410                 415

Val Gly Lys Phe Pro Phe Leu Ala Asn Ser Arg Ala Lys Thr Asn Val
                420                 425                 430

Asp Thr Asp Gly Phe Val Lys Phe Leu Val Glu Lys Asp Thr Asp Lys
            435                 440                 445

Ile Leu Gly Val Phe Ile Ile Gly Pro Asn Ala Gly Glu Met Ile Ala
            450                 455                 460

Glu Ala Gly Leu Ala Met Glu Tyr Gly Ala Ser Ala Glu Asp Val Ala
465                 470                 475                 480

Arg Thr Cys His Ala His Pro Thr Leu Ser Glu Ala Phe Lys Glu Gly
                485                 490                 495

Ala Met Ala Ala Tyr Ser Lys Pro Ile His Phe
                500                 505
```

(2) INFORMATION FOR SEQ ID NO:35:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
    (A) DESCRIPTION: /desc = "Synthetic DNA"

(xi) SEQUENCE DESCRIPTION: SEQ ID NO:35:

AARGTNGCNG TNYTNGGNGC NWSNGG                                26

(2) INFORMATION FOR SEQ ID NO:36:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(xi) SEQUENCE DESCRIPTION: SEQ ID NO:36:

YTNWSNYTNY TNATGAARYT NAAYCC                                26

(2) INFORMATION FOR SEQ ID NO:37:

(i) SEQUENCE CHARACTERISTICS:
        (A) LENGTH: 1009 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:37:

TTCTCTCTGT TGATGAAGCT CAACCCCAAG GTCACCGAGC TGCGCCTGTA CGACATCCGT    60

CTTGCTCCGG GTGTTGCTGC GGACCTCTCG CACATCAACA CGCCTGCGGT GACCTCGGGC   120

TACGCCCAGG ACNATCTTGA GGGTGCCGTT GACGGCGCAA AGATTGTCCT GATCCCCGCC   180

GGTATGCCGC GCAAGCCCGG CATGACCCGT GACGATCTGT TCAACTCGAA CGCCTCGATC   240

GTCCGTGACC TCGCCAAGAC CGTGGCCAAG GTTGCCCCCA AGGCCTACAT TGGTATCATC   300

TCGAACCCCG TCAACTCGAC GGTGCCGATC GTCGCCGAGG TGTTCAAGAA GGCGGGTGTG   360

TACGACCCCA AGCGCCTCTT CGGTGTGACC ACGCTCGACA CCACGCGTGC GGCCACCTTC   420

CTGTCGGGCA TCACTGGCTC GGAACCGCAG ACCACCAATG TCCCGGTCAT TGGTGGTCAC   480

TCGGGTGTGA CCATCGTGCC TCTGGTCTCG CAGGCCCCCC AGGGTGACAA GGTGCAGGCC   540

GGCGAGCAGT ACGACAAGCT CGTCCACCGC ATTCAGTTCG GTGGTGACGA GGTCGTTAAG   600

GCCAAGGACG GTGCGGGTTC GGCGACGCTG TCGATGGCCT ACGCCGCCGC TGTCTTCACT   660

GAGGGCCTGC TCAAGGGTCT TGACGGTGAG GCGGTGACGC AGTGCACCTT CGTTGAGAGC   720

CCCCTGTTCA AGGACCAGGT TGACTTCTTC GCTTCGCCCG TCGAGTTCGG CCCCGAGGGC   780

GTGAAGAACA TCCCTGCCCT GCCCAAGCTC ACCGCTGAGG AGCAGAAGCT GNTNGACGCC   840

TGCCTGCCCG ACCTTGCCAA GAACATCAAG AAGGGTGTTG CGTGGGTTGC CGAGAACCCC   900

TAAATGCGCA GAACCAGCTT CCACGGAGCT TGCGCCAAGG AAAGGAAACG CACATTTNTA   960

TAGAGCGTAG CTTTGTCCCT TTCCATTTAA AAAAAAAAA AAAAAAAA                1009

(2) INFORMATION FOR SEQ ID NO:38:

(i) SEQUENCE CHARACTERISTICS:
        (A) LENGTH: 1008 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:38:

| | | | | | |
|---|---|---|---|---|---|
| CTAAGATTCT | TGATGAAGCT | GAACCCCAAG | GTTACCGAGC | TCCGCCTGTA | CGACATCCGC | 60
| CTCGCTCCGG | GTGTTGCTGC | GGATCTCTCG | CACATCAACA | CCCCCGCGGT | GACTTCGGGC | 120
| TACGCCCAGG | ACGACCTCGA | GGGTGCCGTC | GACGGTGCGG | AGATTGTGCT | GATCCCCGCC | 180
| GGTATGCCGC | GCAAGCCCGG | CATGACCCGT | GACGACCTGT | TCAACTCGAA | CGCCTCGATT | 240
| GTCCGTGACC | TCGCCAAGGT | CGTGGCTAAG | GTCGCCCCAA | AGGCTTACAT | CGGCGTCATC | 300
| TCGAACCCCG | TCAACTCGAC | GGTGCCGATC | GTCGCTGAGG | TGTTAAAGAA | GGCCGGTGTG | 360
| TACGACCCCA | AGCGCCTCTT | CGGTGTGACC | ACGCTCGACA | CCACGCGCGC | GGCCACCTTC | 420
| CTGTCGGGCA | TTGCTGGCTC | GGAACCGCAG | ACCACCAACG | TCCCCGTCAT | TGGTGGCCAC | 480
| TCGGGTGTGA | CCATTGTGCC | CCTGATCTCG | CAGGCCGCCC | AGGGTGACAA | GGTGCAGGCT | 540
| GGCGAGCAGT | ACGACAAGCT | TGTGCACCGC | ATCCAGTTCG | GTGGTGACGA | GGTCGTCAAG | 600
| GCCAAGGACG | GTGCCGGTTC | GGCGACGCTC | TCGATGGCCT | ACGCCGCCGC | TGTTTTCACC | 660
| GAGGGCCTGC | CCAAGGGTCT | CGACGGTGAG | GCGGTGACGC | AGTGCACCTT | CGTCGAGAGC | 720
| CCCCTGTTCA | AGGACCAGGT | CGANTTCTTC | GCTTCGCCCG | TCGAGTTCGG | CCCCGAGGGT | 780
| GTGAAGAACA | TCCCTGNTCT | GCCGAAGCTC | ACCGCCGAGG | AGCAGAAGCT | GNTNGACGCC | 840
| TGCCTGCCCG | ACCTTGCCAA | GAACATCAAG | AAGGGCGTTG | CGTGGGCCGC | CGAGAACCCG | 900
| TAAATGCGCA | AAGCAATNTT | TTACGGAGCT | TGCGCGAAGG | AAAGGAAATG | TACGTTTNTA | 960
| TAGAACGTAG | ATCTGTCCCT | TTCCACCTAA | AAAAAAAAAA | AAAAAAAA | | 1008

(2) INFORMATION FOR SEQ ID NO:39:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 15
        (D) OTHER INFORMATION: /mod_base= i (ix) FEATURE:
        (A) NAME/KEY: modified_base
        (B) LOCATION: 18
        (D) OTHER INFORMATION: /mod_base= i (xi) SEQUENCE DESCRIPTION: SEQ ID NO:39:

GGNAAYAAYG GNYTNWSNGA RGT                                               23

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 18
        (D) OTHER INFORMATION: /mod_base= i (xi) SEQUENCE DESCRIPTION: SEQ ID NO:40:

```
GARGTNGTNT AYAARCCNGA                                            20
```

(2) INFORMATION FOR SEQ ID NO:41:

(i) SEQUENCE CHARACTERISTICS:
        (A) LENGTH: 427 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:41:

```
GAAGTGGTGT ACAAGCCGGA CTCGCAGTCC ACGGACGAGT TCATCGTCAT CGTCAACCCC    60

GACTCGTACC AGTCGTGGCG CTCGGGCAAC CGCACCATCC CGCTCGCGGA TGTCGTCGAC   120

TCCTTCCACA TCTACCACTC GGGCCAGGGC AGCCAGGGCA TCCTCGGCCA GGTGTCGAAG   180

CAGCAGCTCG ACTCCGTGTT CGGTACCGCG AAGGAGGACG AGGCGGTGAT CCTCATCCTC   240

GAGCGCGGCC ACCTCCAGCA CGGCAAAATG CGTGGCCACG ACAAGTCGGG CCGCAACAGC   300

TCGCGCTAAG CCATAGTGGT ACAGTAGGTA CCGGGCCCCC AAGGCCCGAT GCGGGCGCTG   360

CCGCCTGCTA TCCAACATGA TTGTACCTAC GTAAAAAAAA AAAAAAAAA AAAAAAAAA    420

AAAAAAA                                                           427
```

(2) INFORMATION FOR SEQ ID NO:42:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:42:

```
Ile Pro Trp Thr Pro Glu Leu Asp Ser Gly Glu Val Cys Gly Ile
 1               5                  10                  15
```

(2) INFORMATION FOR SEQ ID NO:43:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:43:

Ser Lys Ala Leu Gly Ala Thr Ile Asp Leu Ser Ala Lys His Phe
 1               5                  10                  15

(2) INFORMATION FOR SEQ ID NO:44:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:44:

Ala Thr Ile Asp Leu Ser Ala Lys His Phe Gly Glu Arg Thr Ala
 1               5                  10                  15

(2) INFORMATION FOR SEQ ID NO:45:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:45:

Pro Gly Asp Pro Thr Ala Thr Ala Lys Gly Asn Glu Ile Pro Asp
 1               5                  10                  15

Thr Leu Met Gly Tyr Ile Pro Trp Thr Pro Glu Leu Asp
                20                  25

(2) INFORMATION FOR SEQ ID NO:46:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:46:

Val Glu Tyr Phe Gly Ile Asp Glu Gly Glu Pro Lys
 1               5                  10

(2) INFORMATION FOR SEQ ID NO:47:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:47:

Asp Asn Leu Thr Phe Ala Gln Asp Val Asn Cys Glu Phe
 1               5                  10

```
(2) INFORMATION FOR SEQ ID NO:48:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:48:

Val Val Ile Val Ala Val Pro Gly Xaa Phe Thr Pro Thr Cys Thr
  1               5                  10                  15

Ala Asn His Val Pro Xaa Tyr Xaa Glu
                20

(2) INFORMATION FOR SEQ ID NO:49:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:49:

Asp Gln Asp Pro Leu Thr Thr His His Pro Val Ile Gly Trp Asp
  1               5                  10                  15

Xaa Xaa Glu His Ala
                20

(2) INFORMATION FOR SEQ ID NO:50:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:50:

Ala Trp Trp Asn Val Val Asn Trp Ala Glu Ala Glu Lys
  1               5                  10

(2) INFORMATION FOR SEQ ID NO:51:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:51:

Phe Xaa Gly Gly Gly His Ile Asn Xaa Ser Leu Phe
  1               5                  10

(2) INFORMATION FOR SEQ ID NO:52:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:52:

Lys Tyr Thr Leu Pro Pro Leu Pro Tyr Asp Tyr Gly Ala Leu Glu
  1               5                  10                  15
```

```
Pro Ala Ile Ser Gly Glu Ile Met Glu Thr His Tyr Gly Lys His
            20                  25                  30
```

(2) INFORMATION FOR SEQ ID NO:53:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:53:

```
Xaa Xaa Xaa Xaa Xaa Glu Pro Tyr Asp Val Ile Val Ile Gly Gly
 1               5                  10                  15
Gly Pro Gly Gly Tyr Val Ala Xaa Xaa Lys Xaa Xaa Gln
            20                  25
```

(2) INFORMATION FOR SEQ ID NO:54:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:54:

```
Arg Lys Val Ala Val Leu Gly Ala Ser Gly Gly Ile Gly Gln Pro
 1               5                  10                  15
Leu Ser Leu Leu Met Lys Leu Asn Pro Lys Val Thr Glu Leu Arg
            20                  25                  30
```

(2) INFORMATION FOR SEQ ID NO:55:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:55:

```
Gly Asn Asn Gly Leu Ser Glu Val Val Tyr Lys Pro Asp Xaa Gln
 1               5                  10                  15
Xaa Thr Xaa Glu Phe Xaa Val Ile
            20
```

(2) INFORMATION FOR SEQ ID NO:56:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:56:

```
Val Asp Gln Xaa Tyr Phe Gly Leu Xaa
 1               5
```

(2) INFORMATION FOR SEQ ID NO:57:

(i) SEQUENCE CHARACTERISTICS:
        (A) LENGTH: 25 amino acids
        (B) TYPE: amino acid
        (D) TOPOLOGY: linear -continued

```
    (ii) MOLECULE TYPE: peptide (xi) SEQUENCE DESCRIPTION: SEQ ID NO:57:

Ser Asn Val Phe Phe Asp Ile Thr Lys Asn Gly Ser Pro Leu Gly
  1               5                  10                  15

Thr Ile Lys Phe Lys Leu Phe Asp Asp Val
                20                  25

(2) INFORMATION FOR SEQ ID NO:58:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:58:

His His Gln Thr Tyr Val Asn Asn Leu Asn Ala Ala Xaa Lys
  1               5                  10
```